United States Patent
Parham et al.

(10) Patent No.: US 7,742,564 B2
(45) Date of Patent: Jun. 22, 2010

(54) SYSTEMS AND METHODS FOR DETECTING AN IMAGE OF AN OBJECT BY USE OF AN X-RAY BEAM HAVING A POLYCHROMATIC DISTRIBUTION

(75) Inventors: Christopher Parham, Raleigh, NC (US); Zhong Zhong, Stony Brook, NY (US); Etta Pisano, Chapel Hill, NC (US); Dean Connor, Shirley, NY (US); Leroy D. Chapman, Saskatoon (CA)

(73) Assignees: The University of North Carolina at Chapel Hill, Chapel Hill, NC (US); Brookhaven Science Associates, Upton, NY (US); The University of Saskatchewan, Saskatoon, Saskatchewan (CA)

( * ) Notice: Subject to any disclaimer, the term of this patent is extended or adjusted under 35 U.S.C. 154(b) by 116 days.

(21) Appl. No.: 11/657,391

(22) Filed: Jan. 24, 2007

(65) Prior Publication Data
US 2007/0291896 A1    Dec. 20, 2007

Related U.S. Application Data

(60) Provisional application No. 60/761,796, filed on Jan. 24, 2006, provisional application No. 60/761,797, filed on Jan. 24, 2006, provisional application No. 60/819,019, filed on Jul. 6, 2006.

(51) Int. Cl.
*G01N 23/20*    (2006.01)
*G01N 23/201*    (2006.01)
*G01N 23/207*    (2006.01)

(52) U.S. Cl. .............................. 378/71; 378/70; 378/84; 378/85; 378/86; 378/87; 378/88; 378/89

(58) Field of Classification Search ............... 378/70, 378/71, 73, 76, 82, 84, 85, 86, 87, 88, 89, 378/90
See application file for complete search history.

(56) References Cited

U.S. PATENT DOCUMENTS

| | | |
|---|---|---|
| 3,598,471 A | 8/1971 | Baldwin et al. |
| 3,639,039 A | 2/1972 | Rhodes, Jr. |

(Continued)

FOREIGN PATENT DOCUMENTS

WO    WO 02/12871 A1 *    2/2002

OTHER PUBLICATIONS

B. D. Cullity and S. R. Stock. Elements of X-Ray Diffraction, third edition (Upper Saddle River, New Jersey: Prentice Hall, 2001), p. 4-28 and 641-643.*

(Continued)

*Primary Examiner*—Allen C. Ho
(74) *Attorney, Agent, or Firm*—Jenkins, Wilson, Taylor & Hunt, P.A.

(57) ABSTRACT

Systems and methods for detecting an image of an object using an X-ray beam having a polychromatic energy distribution are disclosed. According to one aspect, a method can include detecting an image of an object. The method can include generating a first X-ray beam having a polychromatic energy distribution. Further, the method can include positioning a single monochromator crystal in a predetermined position to directly intercept the first X-ray beam such that a second X-ray beam having a predetermined energy level is produced. Further, an object can be positioned in the path of the second X-ray beam for transmission of the second X-ray beam through the object and emission from the object as a transmitted X-ray beam. The transmitted X-ray beam can be directed at an angle of incidence upon a crystal analyzer. Further, an image of the object can be detected from a beam diffracted from the analyzer crystal.

140 Claims, 62 Drawing Sheets

U.S. PATENT DOCUMENTS

| | | | |
|---|---|---|---|
| 3,801,785 | A | 4/1974 | Barrett |
| 3,882,310 | A | 5/1975 | Barrett |
| 3,993,398 | A | 11/1976 | Noguchi et al. |
| 4,284,844 | A | 8/1981 | Belles |
| 4,310,227 | A | 1/1982 | Zinchuk |
| 4,517,599 | A | 5/1985 | Zwirn et al. |
| 4,532,548 | A | 7/1985 | Zwirn et al. |
| 4,647,154 | A | 3/1987 | Birhbach et al. |
| 4,882,619 | A | 11/1989 | Hasegawn et al. |
| 5,319,694 | A * | 6/1994 | Ingal et al. ............ 378/84 |
| 5,339,305 | A | 8/1994 | Curtis et al. |
| 5,347,400 | A | 9/1994 | Hunter |
| 5,430,807 | A | 7/1995 | Gravely |
| 5,532,814 | A | 7/1996 | Cha |
| 5,535,291 | A | 7/1996 | Spencer et al. |
| 5,541,026 | A | 7/1996 | Matsumoto |
| 5,596,620 | A | 1/1997 | Canistraro et al. |
| 5,634,669 | A | 6/1997 | Colgate, Jr. |
| 5,635,720 | A | 6/1997 | Mooney et al. |
| 5,667,736 | A | 9/1997 | Chien |
| 5,801,889 | A | 9/1998 | Meyers et al. |
| 5,802,137 | A | 9/1998 | Wilkins |
| 5,805,342 | A | 9/1998 | Gravely |
| 5,867,264 | A | 2/1999 | Hinnrichs |
| 5,933,277 | A | 8/1999 | Troxell et al. |
| 5,953,161 | A | 9/1999 | Troxell et al. |
| 5,969,864 | A | 10/1999 | Chen et al. |
| 5,974,211 | A | 10/1999 | Slater |
| 5,987,095 | A * | 11/1999 | Chapman et al. ............ 378/70 |
| 6,041,098 | A * | 3/2000 | Touryanski et al. ........... 378/70 |
| 6,086,708 | A | 7/2000 | Colgate, Jr. |
| 6,088,425 | A | 7/2000 | Ono |
| 6,100,978 | A | 8/2000 | Naulleau et al. |
| 6,163,593 | A * | 12/2000 | Koller et al. ............ 378/144 |
| 6,221,579 | B1 | 4/2001 | Everhart et al. |
| 6,226,349 | B1 * | 5/2001 | Schuster et al. ............ 378/84 |
| 6,320,648 | B1 | 11/2001 | Brueck et al. |
| 6,349,004 | B1 | 2/2002 | Fisher et al. |
| 6,385,289 | B1 * | 5/2002 | Kikuchi ............ 378/79 |
| 6,399,295 | B1 | 6/2002 | Kaylor et al. |
| 6,411,367 | B1 | 6/2002 | Baker et al. |
| 6,517,490 | B1 | 2/2003 | Garlick |
| 6,525,806 | B1 | 2/2003 | Smith |
| 6,573,040 | B2 | 6/2003 | Everhart et al. |
| 6,577,708 | B2 * | 6/2003 | Chapman et al. ............ 378/82 |
| 6,685,641 | B2 | 2/2004 | Liu |
| 6,754,307 | B2 * | 6/2004 | Brendler et al. ............ 378/108 |
| 6,757,104 | B2 | 6/2004 | Nakai |
| 6,760,399 | B2 | 7/2004 | Malamud |
| 6,836,530 | B2 * | 12/2004 | Singer et al. ............ 378/34 |
| 6,870,896 | B2 * | 3/2005 | Protopopov ............ 378/36 |
| 6,927,748 | B2 | 8/2005 | Hughes et al. |
| 6,947,521 | B2 * | 9/2005 | Wernick et al. ............ 378/70 |
| 6,953,643 | B2 | 10/2005 | Bourdillon |
| 6,980,378 | B2 | 12/2005 | Lee |
| 6,987,616 | B2 | 1/2006 | Tamada et al. |
| 6,991,895 | B1 | 1/2006 | Yen et al. |
| 7,076,025 | B2 * | 7/2006 | Hasnah et al. ............ 378/82 |
| 7,095,510 | B2 | 8/2006 | Fukui |
| 7,110,503 | B1 * | 9/2006 | Kumakhov ............ 378/119 |
| 7,170,669 | B1 | 1/2007 | Jain et al. |
| 7,183,547 | B2 | 2/2007 | Yun et al. |
| 7,193,767 | B1 | 3/2007 | Peeri |
| 7,224,528 | B2 | 5/2007 | Phillips et al. |
| 7,245,696 | B2 | 7/2007 | Yun et al. |
| 7,330,530 | B2 * | 2/2008 | Chapman ............ 378/85 |
| 7,431,464 | B2 | 10/2009 | Park |
| 2003/0112421 | A1 | 6/2003 | Smith |
| 2003/0149357 | A1 | 8/2003 | Liu |
| 2004/0101676 | A1 | 5/2004 | Phillips et al. |
| 2004/0121241 | A1 | 6/2004 | Kodama |
| 2005/0062928 | A1 | 3/2005 | Yau et al. |
| 2005/0069696 | A1 | 3/2005 | King et al. |
| 2005/0269818 | A1 | 12/2005 | Forde |
| 2007/0013983 | A1 | 1/2007 | Kitamura et al. |
| 2007/0024828 | A1 | 2/2007 | Liao et al. |

OTHER PUBLICATIONS

X-Ray Data Booklet, second edition (Lawrence Berkeley National Laboratory, 2001).*

PCT International Search Report for PCT Application No. PCT/US07/01836 dated Feb. 13, 2008.

PCT International Searching Authority Invitation to Pay Additional Fees and, Where Applicable, Protest fee for PCT Application No. PCT/US07/01836 dated Sep. 28, 2007.

Communication of European publication number and information on the application of Article 67(3) EPC for Application No. 07762560.6 (PCT/US2007/001836).

PCT Written Opinion dated Apr. 13, 2009 for PCT Application No. PCT/US07/01836.

PCT Notification of Transmittal of International Preliminary Examination Report dated Nov. 16, 2009 for PCT International Application No. PCT/US07/01836.

Patent Application No. 2007/80009742.9 has been published in the Chinese Patent Gazette on Apr. 8, 2009 as Publication No. CN 101405596 A.

Indian Patent Application No. 4155/CHENP/2008 has been published in the Patent Office Journal on Mar. 13, 2009.

* cited by examiner

STEPWEDGE

CALCIFICATION SIMULATION

LINE PAIR CLUSTERS

FIG. 54A
 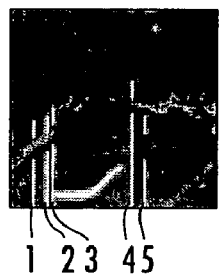 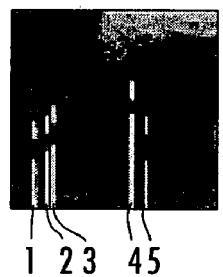 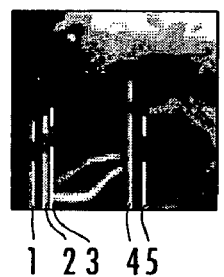
FIG. 54B  FIG. 54C  FIG. 54D  FIG. 54E

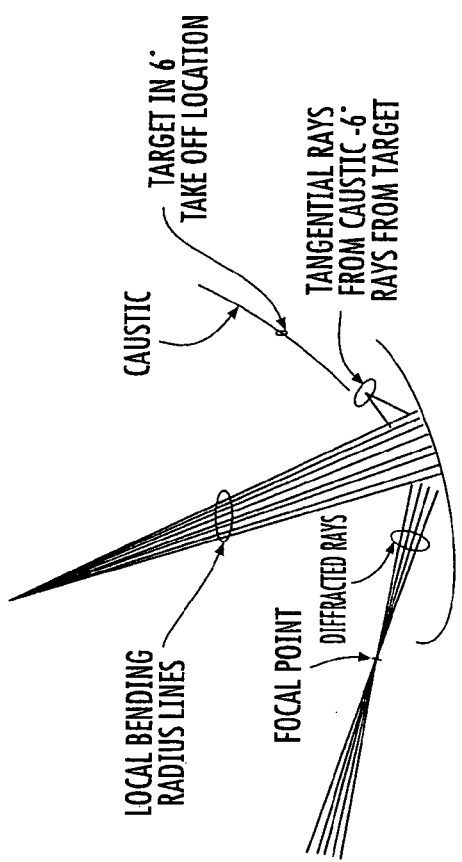
FIG. 57
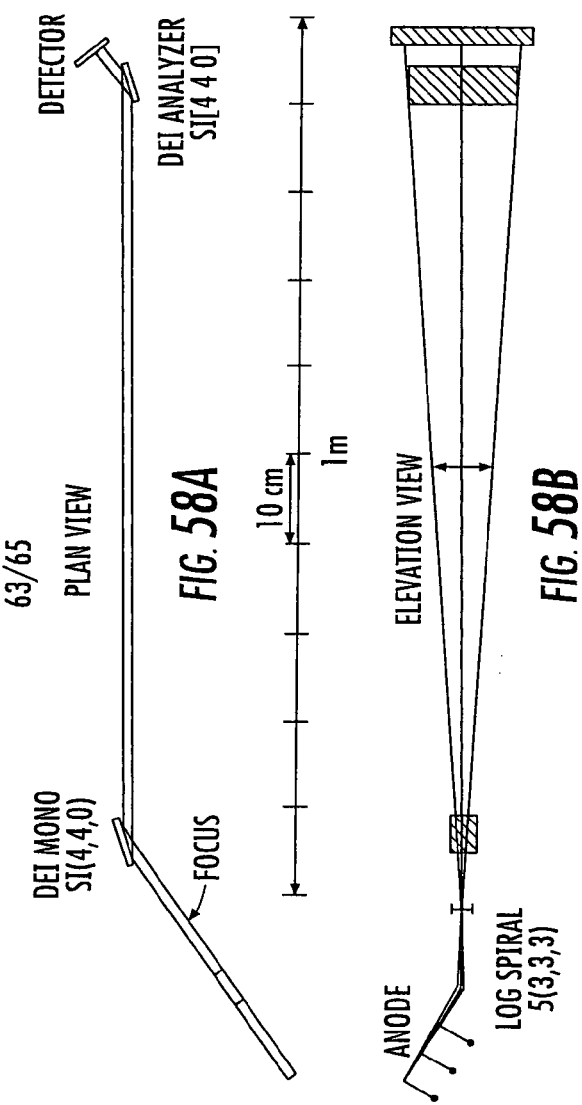
FIG. 58A
FIG. 58B

SYSTEMS AND METHODS FOR DETECTING AN IMAGE OF AN OBJECT BY USE OF AN X-RAY BEAM HAVING A POLYCHROMATIC DISTRIBUTION

RELATED APPLICATIONS

This non-provisional patent application claims the benefit of U.S. Provisional Application No. 60/761,796, filed Jan. 24, 2006, U.S. Provisional Application No. 60/761,797, filed Jan. 24, 2006, and U.S. Provisional Application No. 60/819,019, filed Jul. 6, 2006, the disclosures of which are incorporated by reference herein in their entireties.

GOVERNMENT INTEREST

This presently disclosed subject matter was made with U.S. Government support under contract number DE-AC02-98CH10886 awarded by the U.S. Department of Energy. Thus, the U.S. Government has certain rights in the presently disclosed subject matter.

TECHNICAL FIELD

The subject matter disclosed herein relates to X-ray imaging. More particularly, the subject matter disclosed herein relates to systems and methods for detecting an image of an object by use of an X-ray beam having a polychromatic distribution.

BACKGROUND

X-ray imaging has been used in a variety of fields for imaging objects. For example, X-ray imaging has been used extensively in the medical field for non-destructive testing and X-ray computed tomography (CT). Various other types of technology are also being used for medical imaging. A summary of some currently available medical imaging technologies are summarized below in this section.

X-Ray Radiography Using X-Ray Absorption

Conventional X-ray radiography measures the projected X-ray absorption, or attenuation, of an object. Attenuation differences within the object provide contrast of embedded features that can be displayed as an image. For example, cancerous tissues generally appear in conventional radiography because these tissues are denser than the surrounding non-cancerous tissues. The best absorption contrast is generally obtained at X-ray energies where the absorption is high. Conventional radiography is typically performed using lower X-ray energy in higher doses to allow greater absorption and, thus, better contrast and images. Using X-rays having higher energy generally requires a lower dosage to be used because of patient safety concerns. In general, as the X-ray energy level increases and the X-ray dose decreases, the quality of the conventional radiography image lessens.

X-ray sources for the current generation of radiographic imaging systems use a design based on a standard cathode/anode X-ray tube. The energy spectrum and general output characteristics of an X-ray tube are primarily determined by the anode material and configuration. Selecting the proper anode material is based heavily on the application, specifically on what modality and what structure is to be imaged. For mammography, the most common anode material is molybdenum, but rhodium is also used. Molybdenum's average energy of approximately 18 keV provides the appropriate spectrum for imaging soft tissue. For mammography systems, the anode is often stationary and mounted in a copper block to reduce heat. A major engineering problem is the generation of heat in the anode by the focused electron beam. X-ray tubes that have a stationary anode are more prone to heating because the primary means of heat removal is the surrounding copper anode, even with its high thermal conductance. Advancements in X-ray tube development have led to the use of a rotating anode, which rotates so that the electron beam from the cathode does not impact the same area on the anode. The primary acquisition detection method for radiography, until the relatively recent advent of digital detectors, is X-ray film.

X-ray imaging for screening mammography has been used to identify early stages of breast cancer. It is well known that breast cancer mortality among women under screened controls can be significantly reduced when compared with unscreened controls. Mammography tends to identify smaller and less advanced stages of cancer, when compared with cancers found by breast physical examination or breast self-examination. Treatment of smaller and less advanced stages of breast cancer result in better survival rates. It is quite apparent that enhanced radiology methods can be used to detect even smaller and earlier stage breast cancers. Approximately 10% of clinically obvious breast cancers are not visible in images produced by conventional mammography methods. In addition, it is typically difficult to distinguish between benign lesions and malignant ones using conventional radiology.

In particular, breast cancer which is not visible with conventional mammography techniques occurs most frequently in patients with relatively large amounts of breast glandular tissue. The density of the breast glandular tissue tends to obscure underlying pathology. In order to detect early stages of cancer, it is desirable to increase the sensitivity of mammography so that smaller and earlier stages of breast cancer can be detected. Earlier detection of breast cancer may result in significantly reduced mortality rates.

Mammographic technology has improved dramatically over the last few decades. For example, dedicated mammography equipment now exists with appropriate X-ray beam quality, adequate breast compression and automatic exposure control. However, conventional mammographic technology still depends upon the depiction of X-ray absorption to define differences between normal and abnormal tissues.

Limitations of conventional radiology are also apparent in imaging cartilage, such as during detection and treatment of injuries or degenerative joint diseases, such as osteoarthritis. Better imaging techniques would be beneficial for detecting such degenerative diseases earlier, such as before the point of irreversible damage.

Diffraction Enhanced Imaging (DEI)

DEI is an X-ray imaging technique that dramatically extends the capability of conventional X-ray imaging. The DEI technique is an X-ray imaging modality capable of generating contrast from X-ray absorption, X-ray refraction, and ultra-small angle scatter rejection (extinction). In contrast, conventional X-ray imaging techniques measures only X-ray absorption. The DEI absorption image and peak image shows the same information as a conventional radiograph, except that it is virtually free of scatter degradation. Based on Bragg's law of X-ray diffraction, $n\lambda = 2d \sin(\theta)$, DEI utilizes the Bragg peak of perfect crystal diffraction to convert angular changes into intensity changes, providing a large change in intensity for a small change in angle. Thus, DEI is well suited to soft-tissue imaging, and very promising for mammography.

DEI techniques have demonstrated improvements in object visualization when compared to conventional X-ray imaging techniques, but none have addressed the possibility of extending the usable energy range and decreasing or eliminating the need for X-ray absorption. The decrease or elimination of X-ray absorption is of significant concern in the medical field.

The use of a silicon analyzer crystal in the path of the X-ray beam generates two additional forms of image contrast, X-ray refraction, and extinction (ultra small angle scatter rejection). DEI utilizes highly collimated X-rays prepared by X-ray diffraction from perfect single-crystal silicon, which has heretofore required the high flux and energy range of a synchrotron to generate images. These collimated X-rays are of single X-ray energy, practically monochromatic, and are used as the beam to image an object.

Objects that have very little absorption contrast may have considerable refraction and extinction contrast, thus improving visualization and extending the utility of X-ray imaging. Applications of DEI techniques to biology and materials science have generated significant gains in both contrast and resolution, indicating the potential for use in mainstream medical imaging. An area of medicine where DEI may be particularly effective is in breast imaging for cancer diagnosis, where the diagnostic structures of interest often have low absorption contrast, making them difficult to see. Structures with low absorption contrast, such as the spiculations extending from a malignant mass, have high refraction and ultra-small angle scatter contrast. It is desirable to provide a DEI system with the capability to increase both the sensitivity and specificity of X-ray-based breast imaging.

Multiple studies have demonstrated improved image contrast in both medical and industrial applications of DEI. Advantages of DEI systems over conventional X-ray imaging systems in the medical field include a dramatic reduction in patient radiation dose and improved image quality. The dose reduction is due to the ability of DEI systems to function at higher X-ray energies. X-ray absorption is governed by the photoelectric effect, $Z^2/E^3$, where Z is the atomic number and E is the photon energy.

Until now, DEI systems have required the use of a synchrotron to produce an initial radiation beam which is manipulated by other system components for imaging an object. A synchrotron provides a highly collimated, high flux X-ray beam across a wide range of energies. A synchrotron generates radiation through the movement of charged particles in a circular orbit, specifically electrons, causing a release of photons. The unique properties of synchrotron radiation produce high flux X-rays over a wide energy range which can be used for wide range of applications.

The core theory of DEI is based on Bragg's law of X-ray diffraction. Bragg's law is defined by the following equation:

$$n\lambda = 2d \sin(\theta)$$

where $\lambda$ is the wavelength of the incident X-ray beam, $\theta$ is the angle of incidence, d is the distance between the atomic layers in the crystal, and n is an integer.

A monoenergetic radiograph contains several components that can affect image contrast and resolution: a coherently scattered component $I_c$, an incoherently scattered component $I_I$, and a transmitted component. X-rays passing through an object or medium where there are variations in density can be refracted, resulting in an angular deviation. Specifically, deviations in the X-ray range result from variations in $\rho t$ along the path of the beam, where $\rho$ is the density and t is the thickness. A fraction of the incident photons may also be diffracted by structures within an object, which are generally on the order of milliradians and referred to as small angle scattering. The sum total of these interactions contributed to the recorded intensity in a radiograph $I_N$, which can be represented by the following equation:

$$I_N = I_R + I_D + I_C + I_I$$

System spatial resolution and contrast will be degraded by the contributions of both coherent and incoherent scatter. Anti-scatter grids are often used in medical imaging to reduce the contribution of scatter, but there performance is limited and use of a grid often requires a higher dose to compensate for the loss in intensity.

The DEI technique utilizes a silicon analyzer crystal in the path of the post-object X-ray beam to virtually eliminate the effects of both coherent and incoherent scatter. The narrow angular acceptance window of the silicon analyzer crystal is referred to as its rocking curve, and is on the order of microradians for the X-ray energies used in DEI. The analyzer acts as an exquisitely sensitive angular filter, which can be used to measure both refraction and extinction contrast. Extinction contrast is defined as the loss of intensity from the incident beam due to scattering, which can produce substantial improvements in both contrast and resolution.

The Darwin Width (DW) is used to describe reflectivity curves, and is approximately the Full Width at Half Maximum (FWHM) of the reflectivity curve. Points at $-\frac{1}{2}$ DW and $+\frac{1}{2}$ DW are points on the curve with a steep slope, producing the greatest change in photon intensity per microradian for a particular analyzer reflection and beam energy. Contrast at the peak of the analyzer crystal rocking curve is dominated by X-ray absorption and extinction, resulting in near scatter-free radiographs. Refraction contrast is highest where the slope of the rocking curve is greatest, at the $-\frac{1}{2}$ and $+\frac{1}{2}$ DW positions. One DEI based image processing technique uses these points to extract the contrast components of refraction and apparent absorption from these image pairs.

The following paragraph describes of this technique for extracting the contrast components of refraction and apparent absorption from an image pair. When the analyzer crystal is set to an angle representing $+/-\frac{1}{2}$ DW for a given reflection and beam energy, the slope of the rocking curve is relatively consistent and can be represented as a two-term Taylor series approximation as represented by the following equation:

$$R(\theta_0 + \Delta\theta_Z) = R(\theta_0) + \frac{dR}{d\theta}(\theta_0)\Delta\theta_Z.$$

If the analyzer crystal is set to the low-angle side of the rocking curve ($-\frac{1}{2}$ DW), the resulting image intensity can be represented by the following equation:

$$I_L = I_R\left(R(\theta_L) + \frac{dR}{d\theta}\bigg|_{\theta=\theta_L} \Delta\theta_z\right).$$

The recorded intensity for images acquired with the analyzer crystal set to the high-angle position (+½ DW) can be represented by the following equation:

$$I_H = I_R\left(R(\theta_H) + \frac{dR}{d\theta}(\theta_H)\Delta\theta_z\right).$$

These equations can be solved for the changes in intensity due to apparent absorption ($I_R$) and the refraction in angle observed in the z direction ($\Delta\theta_z$) represented by the following equation:

$$\Delta\theta_z = \frac{I_H R(\theta_L) - I_L R(\theta_H)}{I_L\left(\frac{dR}{d\theta}\right)(\theta_H) - I_H\left(\frac{dR}{d\theta}\right)(\theta_L)}$$

$$I_R = \frac{I_L\left(\frac{dR}{d\theta}\right)(\theta_H) - I_H\left(\frac{dR}{d\theta}\right)(\theta_L)}{R(\theta_L)\left(\frac{dR}{d\theta}\right)(\theta_H) - R(\theta_H)\left(\frac{dR}{d\theta}\right)(\theta_L)}.$$

These equations can be applied to the high and low angle images on a pixel-by-pixel basis to separate the two contrast elements into what is known as a DEI apparent absorption and refraction image. However, it is important to note that each of the single point rocking curve images used to generate DEI apparent absorption and refraction images is useful.

As stated above, current DEI systems include a synchrotron for producing an X-ray beam. Synchrotron-based DEI systems have provided impressive results for many years. However, synchrotrons are large and expensive devices and are not practical for either medical or industrial applications. Given the dramatic increase in contrast and reduction in dose, it would be beneficial to increase the availability of DEI systems for widespread clinical use.

Development of a clinical DEI imager may have significance for women's health and medical imaging in general for the following reasons: (1) DEI has been shown to produce very high contrast for the features that are most important to detection and characterization of breast cancer; (2) the physics of DEI allows for imaging at higher x-ray energies than used with absorption alone; and (3) the ability of DEI to generate contrast without the need of photons to be absorbed dramatically reduces ionization, and thus reduces the absorbed dose.

Further, screen-film mammography has been studied extensively for the last 40 years, and because of many large randomized screening trials, it is known to reduce breast cancer mortality by approximately 18-30%. The rate of breast cancer death in the last few years has begun to decline, likely due in part to the widespread use of this imaging test. However, standard screen-film mammography is neither perfectly sensitive nor highly specific. Dense breast tissue and diffuse involvement of the breast with tumor tends to reduce the sensitivity of screening mammography. For women with dense breasts, lesions that develop are difficult to see because their ability to absorb photons is not much greater than the surrounding adipose tissue, generating little contrast for visualization. Approximately 10-20% of breast cancers that are detected by self-examination or physical examination are not visible by screen-film mammography. In addition, when lesions are detected by mammography and biopsy, only 5-40% of lesions prove to be malignant. Furthermore, approximately 30% of breast cancers are visible in retrospect on prior mammograms.

Current DEI and DEI imaging processing techniques are based heavily on conventional imaging theory and rely, at least in part, on X-ray absorption for image generation. Thus, objects imaged using these techniques absorb radiation. Such radiation exposure is undesirable in applications for medical imaging given concerns of dose, and this reasoning places considerable engineering limitations that make clinical and industrial translation challenging. Thus, it is desirable to provide DEI and DEI techniques that produce high quality images and that rely less on absorption but produce images with equivalent diagnostic quality and feature visualization.

Accordingly, in light of desired improvements associated with DEI and DEI systems, there exists a need for improved DEI and DEI systems and related methods for detecting an image of an object.

SUMMARY

The subject matter described herein includes systems and methods for detecting an image of an object using an X-ray beam having a polychromatic energy distribution. According to one aspect, the subject matter described herein can include a method for detecting an image of an object. The method can include generating a first X-ray beam having a polychromatic energy distribution. Further, the method can include positioning a single monochromator crystal in a predetermined position to directly intercept the first X-ray beam such that a second X-ray beam having a predetermined energy level is produced. Further, an object can be positioned in the path of the second X-ray beam for transmission of the second X-ray beam through the object and emission from the object as a transmitted X-ray beam. The transmitted X-ray beam can be directed at an angle of incidence upon a crystal analyzer. Further, an image of the object can be detected from a beam diffracted from the analyzer crystal.

According to another aspect, a method in accordance with the subject matter described herein can include generating a first X-ray beam having a polychromatic energy distribution. Further, a portion of the first X-ray beam can be blocked such that the first X-ray beam is a collimated fan beam. A monochromator crystal can be positioned in a predetermined position to intercept the collimated fan beam such that a second X-ray beam having a predetermined energy level is produced. The method can include positioning an object in a path of the second X-ray beam for transmission of the second X-ray beam through the object and emitting from the object a transmitted X-ray beam. Further, the method can include directing the transmitted X-ray beam at an angle of incidence upon an analyzer crystal. The method can also include detecting an image of the object from a beam diffracted from the analyzer crystal.

According to another aspect, a method in accordance with the subject matter described herein can include generating a first X-ray beam having a polychromatic energy distribution by generating a plurality of X-ray beams fanning out in different directions from an X-ray point source. The method can also include positioning a monochromator crystal in a predetermined position to intercept the first X-ray beam such that a second X-ray beam having a predetermined energy level is produced. Further, the method can include positioning an object in a path of the second X-ray beam for transmission of the second X-ray beam through the object and emitting from the object a transmitted X-ray beam. The transmitted X-ray beam can be directed at an angle of incidence upon an analyzer crystal. Further, the method can include detecting an image of the object from a beam diffracted from the analyzer crystal.

According to another aspect, a method in accordance with the subject matter described herein can include generating a first X-ray beam having first and second characteristic emission lines. The method can also include positioning a monochromator crystal in a predetermined position to intercept the first X-ray beam such that a second X-ray beam having the first and second characteristic emission lines is produced. Further, the method can include selectively blocking one of the first and second characteristic emission lines of the second X-ray beam and allowing an unblocked on of the first and second characteristic emission lines of the second X-ray beam to pass. An object can be positioned in a path of the unblocked one of the first and second characteristic emission lines of the second X-ray beam for transmission of the unblocked characteristic line of the second X-ray beam through the object and emitting from the object a transmitted X-ray beam. The method can include directing the transmitted X-ray beam at an angle of incidence upon an analyzer crystal. Further, the method can include detecting an image of the object from a beam diffracted from the analyzer crystal.

According to another aspect, a method in accordance with the subject matter described herein can include generating a first X-ray beam having first and second characteristic emission lines. A monochromator crystal can be positioned in a predetermined position to intercept the first X-ray beam such that a second X-ray beam having the first and second characteristic emission lines is produced. Further, the method can include positioning an object in a path of the first and second characteristic emission lines of the second X-ray beam for transmission of the first and second characteristic emission lines of the second X-ray beam through the object and emitting from the object a transmitted X-ray beam. The transmitted X-ray beam can be directed at an angle of incidence upon an analyzer crystal. The method can include detecting an image of the object from a beam diffracted from the analyzer crystal.

In accordance with this disclosure, novel systems and methods for detecting an image of an object using an X-ray beam having a polychromatic energy distribution are provided.

It is an object of the present disclosure therefore to provide novel systems and methods for detecting an image of an object using an X-ray beam having a polychromatic energy distribution. This and other objects as may become apparent from the present disclosure are achieved, at least in whole or in part, by the subject matter described herein.

BRIEF DESCRIPTION OF THE DRAWINGS

Preferred embodiments of the subject matter described herein will now be described with reference to the accompanying drawings, of which:

FIGS. 54A-54E are images of the visualization of fibrils with DEI as compared to a conventional radiograph;

FIG. 57 is a perspective view illustrating the focusing effect of a log-spiral element, with a source at caustic;

FIGS. 58A and 58B are a plan view and an elevation view, respectively, of a characterization system for experimental studies;

DETAILED DESCRIPTION

Figure 1A:
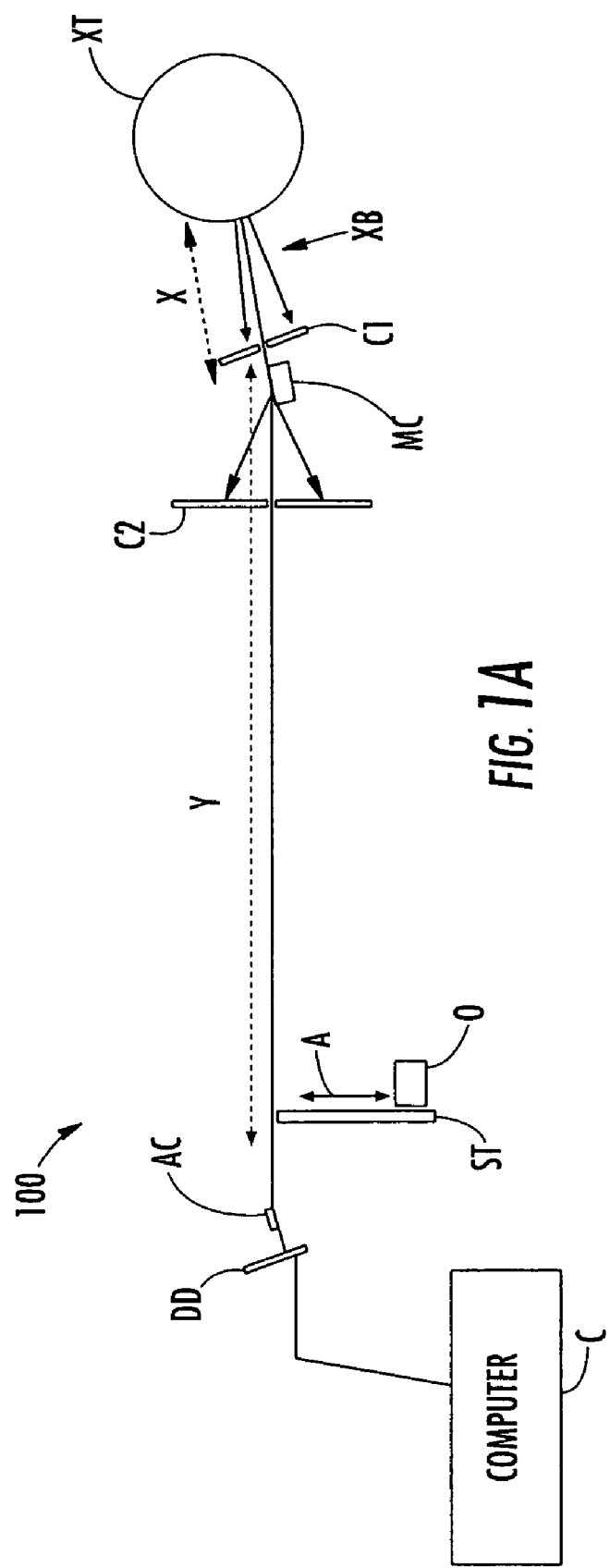
FIGS. 1A-1C are a schematic diagram, a top perspective view, and a side-top schematic view of a DEI system including a single monochromator crystal and operable to produce images of an object according to an embodiment of the subject matter described herein.

The subject matter described herein includes systems and methods for detecting an image of an object using an X-ray beam having a polychromatic energy distribution. In particular, the subject matter described herein discloses improved DEI and DEI systems and related methods for detecting an image of an object. According to one aspect, the subject matter described herein can include a method for detecting an image of an object. The method can include generating a first X-ray beam having a polychromatic energy distribution. Further, the method can include positioning a monochromator crystal in a predetermined position to intercept the first X-ray beam such that a second X-ray beam having a predetermined energy level is produced. Further, an object can be positioned in the path of the second X-ray beam for transmission of the second X-ray beam through the object and emission from the object as a transmitted X-ray beam. The transmitted X-ray beam can be directed at an angle of incidence upon a crystal analyzer. Further, an image of the object can be detected from a beam diffracted from the analyzer crystal. These systems and methods can be advantageous, for example, because they can provide extremely low dose in medical applications, fast scan times, high resolution, and relatively low operation and build costs. Further, for example, these systems can be constructed into a compact unit and be readily usable in clinical and industrial applications.

An imaging processing technique using DEI in accordance with the subject matter described herein can use images acquired at symmetric points of the rocking curve to generate apparent absorption and refraction images of an object. A DEI apparent absorption image is similar to a conventional radiograph image, but exhibits much greater contrast owing to scatter rejection. DEI refraction images can depict the magnitude of small beam deflections caused by large-scale refractive-index features. A DEI extinction image is generated at points on the rocking curve where the primary mechanism of contrast is due to photons that have been scattered by an object on the order of microradians. Another DEI based imaging processing technique is referred to as Multiple Image Radiography (MIR) which uses multiple points on the rocking curve to generate quantitative images representing an object's X-ray absorption, refraction, and ultra-small angle scatter. Systems and methods in accordance with the subject matter described herein can generate images at any point on the analyzer rocking curve, and can thus be used to generate: (1) single image DEI at any analyzer position; (2) DEI apparent absorption and refraction images; (3) MIR absorption, refraction, and scatter images; and (4) mass density images. The ability to generate the raw image data required for these processes and any other DEI based processing technique are useful for all DEI based processing techniques. In addition, systems and methods described herein are amenable for use in computed tomography, and can provide the raw data for use in any DEI-based computed tomography algorithm.

Photon Interactions with Matter

This section provides an overview of X-ray generation, photonics, and photon interactions with matter. Further, this section explains the physical mechanisms of X-ray absorption, refraction, and scatter and how they relate to DEI and DEI image processing methods. The topics of energy deposition, dose measurement, and the associated health effects of radiation exposure are also discussed.

One of the most important underlying physical interactions in radiography is the photoelectric effect. Application of this theory to X-ray imaging helps to explain how contrast is obtained in conventional radiography. X-rays passing through an object, such as breast tissue, can strike an electron and raise its energy to a level above the binding energy of that orbital. If this occurs, the electron will have sufficient energy to overcome the attractive force of the nucleus and leave the atom with a total energy equal to the energy of the incident photon minus the binding energy of the electron. In biological tissues, incident X-rays can lead to direct or indirect free radical formation, which can interact with DNA and other cellular structures leading to mutations and other deleterious effects. The positive aspect of this interaction is that the energy of the X-ray photon is transferred to the electron, which means that it will not encounter the film or detector of an imaging system. Decreasing the amount of transmitted X-rays through an object is referred to as X-ray attenuation, and the primary component of this process in conventional imaging is through absorption via the photoelectric effect.

The probability of photoelectric absorption occurring per unit mass is proportional to $Z^3/E^3$, where Z is the atomic number and E is the energy of the incident photon. For medical imaging, the equation is often simplified to reflect the effect of beam energy, making the probability of photoelectric absorption proportional to $1/E^3$. Since contrast in conventional radiography is based on absorption, absorption contrast will decrease rapidly at higher energy levels. An exception to this trend occurs at the K-absorption edge of an atom, a characteristic energy specific to each element. The probability that a photoelectric interaction will occur increases significantly when the incident photon energy is just below the K-absorption energy, or K-edge.

Since photoelectric absorption is increased with higher atomic number and lower beam energy, imaging breast tissue becomes a challenging endeavor. Most of the primary elements in soft tissue are composed of hydrogen, carbon, nitrogen and oxygen, all of which have relatively low atomic numbers and absorption edges below 1 keV. Both the relatively low average atomic number and low absorption edge of the primary elements composing the parenchyma of breast tissue make determining differences between benign and malignant features challenging, especially in the early stages of disease.

A physical interaction inherent to conventional X-ray generation is that of bremsstrahlung, which is German for "breaking radiation". Electrons at non-relativistic velocities used in imaging systems are accelerated through a voltage and have a kinetic energy defined by the following equation:

$$KE = \frac{1}{2}mv^2$$

Electrons emitted into a metal, such as the anode of an X-ray tube, can be deflected as they pass by the dense atomic nuclei and decelerate rapidly. An electron can release energies ranging from 0 to its total KE, with the loss of energy dependent on how close the passing electron is to the nucleus. Deflections that result in a low energy release have a much higher probability than those that result in a large energy release. Electrons that are accelerated at high potentials and have a strong interaction with the nucleus that results in a significant decrease in velocity can result in the release of a photon in the X-ray band of the energy spectrum. The main source of X-rays generated from diagnostic X-ray tubes comes from bremsstrahlung radiation.

Accelerated electrons interacting with an atom can produce another type of X-ray based primarily on the object's atomic properties, known as characteristic X-rays. If an accelerated electron encounters an electron in an atomic orbital, part of its energy can be transferred and raise the impacted electron to a higher energy level. Ejection of the impacted electron can occur if the energy transferred is equal to or greater than the binding energy of that electron. If an interaction occurs that ejects one of these electrons, an electron from a higher energy level will drop to fill the gap. Since these electrons are going from a high energy level to a lower energy level, the change in energy level is accompanied with a release of energy. An electron that transitions from the second energy level to the first energy level (n=2 to n=1) are referred to as a $K_\alpha$ X-rays. Transitions from the third energy level to the first energy level (n=3 to n=1) are classified as $K_\beta$ X-rays. There are numerous transitions that can occur based on this electronic collision, but the interactions that generate characteristic X-rays are produced by transitions in the lower atomic energy levels.

The energy output spectrum of an X-ray target will depend on the properties of the metal being used. Determining the average energy needed for a particular imaging application is important in selecting a target. For applications that utilize monochromatic X-rays, the characteristic X-rays produced by a target are of particular importance.

Regarding X-ray absorption, when X-ray photons encounter matter, the interaction leads to an attenuation of the incident X-rays, with a portion of the X-rays being absorbed and a portion being transmitted. X-ray attenuation is a loss in photon intensity based on electron density and mean atomic number of an object. Scattering of X-rays can also occur as photons pass through matter and lead to a loss in intensity, but this component is difficult to measure in conventional radiography. Quantification of the amount of photons that are absorbed as they pass through an object of thickness X is determined by how many photons are transmitted ($I_t$) compared to the number of photons in the incident beam ($I_o$). The degree to which photons are attenuated as they pass through matter is a materials property that can be measured, and is termed the attenuation coefficient ($\mu$) with units of $cm^{-1}$. Differences in the linear attenuation coefficients allow for X-ray image contrast, with the highest contrast being between areas of high and low attenuation.

The linear absorption coefficient is proportional to the density of the material traversed, and the tabulated value is often expressed as $\mu/\rho$. This value is called the mass absorption coefficient and it is independent of the physical state of the material (solid, liquid, or gas).

The refraction of light as it passes from one medium to another was first discovered by Willebrord Snell, and the law that defines this process is known at Snell's law. Mathematically, this relationship is defined by the following equation:

$$n_1 \sin(\theta_1) = n_2 \sin(\theta_2)$$

where the incident medium is medium 1, and the refracted medium is medium 2.

The passage of an electromagnetic wave passing from one medium to another is analogous to visible light passing through a medium, with the deviation depending on the index difference. Using the classic example of visible light, light moving from one index of refraction to a medium with a higher index of refraction can be refracted. This example is commonly used to demonstrate refraction of visible light, but the law also applies for X-rays. However, for X-rays, the real parts of the complex refractive indices are less than unity and can be expressed by the following equation:

$$n = 1 - \delta$$

When using high-energy X-rays and materials with a low average atomic number, an approximation for $\delta$ is provided by the following equation:

$$\delta \cong \frac{N\lambda^2 r_e}{2\pi}$$

where N is the number of electrons per unit volume of the sample material, $r_e$ is the classical electron radius, and $\lambda$ is the X-ray wavelength. Using these equations one can show that for a linear interface between two regions with distinct refractive indices, an incident photon will be deflected at an angle $\Delta\theta$ approximated by the following equation:

$$\Delta\theta \approx (n_1 - n_2) \tan \theta_1$$

Photons can primarily undergo three events when they encounter an object: they can pass through without any interaction, they can be absorbed through the photoelectric effect, or they can undergo a scattering event. In its most general definition, scattering is an angular deviation in the path of a photon secondary to an interaction with another object. The characteristics of the photon, the medium it is traveling in, and the properties of the object it encounters has a profound impact on the outcome of the interaction.

Interactions that occur without a loss or transfer of energy are elastic, and X-ray interactions that occur without an associated loss of energy in the incident photon are referred to as elastic scatter, or coherent scatter. In a coherent scattering event, the energy of the primary X-ray photon is first completely absorbed and then re-emitted by the electrons of a single atom. There is no net energy loss in the interaction, but the direction of the photon re-emission is completely arbitrary. For medical imaging, coherent scatter interactions are far less significant than photoelectric interactions or scattering events that occur with a loss of energy, known as incoherent scattering.

In the energy ranges used in diagnostic imaging, the scattering interaction that is dominant and often problematic is incoherent scattering. This effect is known as Compton scattering. A Compton scattering interaction can be described as a collision between an X-ray photon and an electron in the outer energy level of an atom. The energy binding the outer electrons is minimal, and all of the energy lost in the interaction between the photon and the electron is transferred as kinetic energy to the electron. This transfer of energy results in a photon with decreased energy, or increased wavelength, and the ejection of the impacted electron from the atom. Both energy and momentum are conserved in the collision, so the energy and angular deviation of the scattered photon will depend on the amount of energy transferred to the electron. The Compton scattering equation used to describe the change in wavelength is provided by the following equation:

$$\lambda - \lambda' = \frac{h}{mc}(1 - \cos\theta) = \frac{2h}{mc}\sin^2\left(\frac{1}{2}\theta\right)$$

where $\lambda$ is the incident photon wavelength and $\lambda'$ is the scattered photon wavelength.

High energy X-ray photons typically transfer a small amount of energy, making the scattering angle small relative to the initial trajectory of the photon. Conversely, scattering of lower energy X-ray photons is more isotropic in nature. The problem in conventional radiography is that while the lower energy X-rays used in diagnostic imaging are scattered isotropically, those photons that are detected are forward directed. These scattered photons can have a similar energy and direction when compared with the desired photons used to generate an image. The similarity in energy and direction makes their removal by anti-scatter grids and energy filters difficult. For this reason, Compton scattering can reduce resolution and contrast by blurring the resulting image. Ingenious methods have been used to reduce the impact of Compton scattering on radiography, but no conventional X-ray imaging techniques have been successful in completely eliminating this effect.

The development and use of imaging systems that use ionizing radiation are both enabled and grounded by the electromagnetic radiation used to visualize the internal structure of an object or patient. Ionizing radiation is defined as radiation which has enough energy to cause atoms to lose electrons and become ions. X-ray imaging is the most commonly used ionizing imaging modality, but other anatomical and functional imaging modalities utilize ionizing radiation to obtain diagnostic information. An unavoidable consequence of using ionizing radiation is the dose associated with its use, and an understanding of how dose is measured and the associated health effects are essential. As with other systems of measurement, the quantification of radiation exposure has evolved and changed producing numerous units and methods.

Dose is defined as the amount of radiation exposed to or absorbed by a subject or object. The Roentgen is a unit of exposure use to measure the ionization produced in air by X-ray or gamma radiation. Determining the exposure in terms of Roentgens involves determining the sum of the electrical charges on all ions of one sign produced in air when all electrons liberated by photons in a volume element of air are completely stopped in air, divided by the mass of the air in the volume element. One Roentgen (R) is defined as $2.58 \times 10^{-4}$ Coulombs of charge produced by X-ray or gamma rays per kilogram of air. The Roentgen is also defined as the amount of x- and/or gamma radiation that produces a charge of 1 esu ($2.08 \times 10^9$ ion-pairs) in 1 cc of dry air at standard temperature and pressure. Use of the Roentgen is limited to measuring x and gamma radiation, and more importantly it is not a measure of absorbed dose. Its use is not common in medical imaging devices, but its use does persist because the measurement of air ionization is still widely used in other areas.

A more useful measurement of radiation for biological imaging applications takes into account the dose of radiation absorbed by a subject or object, which is expressed in rad. A rad is equal to 100 ergs (1 erg=$10^{-7}$ J) of energy absorbed by 1 gram of tissue. The internationally adopted unit of absorbed radiation is the gray and is equal to 100 rads. A rad or gray is not a measure of total energy, it is a measure of how much dose is absorbed per gram of tissue. In order to determine how much total energy was delivered, one must know the amount of tissue exposed. Both the rad and gray provide a measure of absorbed dose, but it is still just a measure of the amount of energy left behind in a tissue.

In addition to determining the effect particular types of radiation, the type of tissue being exposed also has an impact on the overall effect. Certain types of tissue are more sensitive to radiation than others, with some of the most sensitive being rapidly dividing cells such as hematopoietic stem cells, intestinal epithelium, and spermatogenic cells. A term known as the effective dose is calculated by adding the product of the equivalent doses of the types of tissues irradiated and their weighting factor expressed by the following equation:

$$EffectiveDose = \sum_{i=1}^{n}(EquivalentDoses \times TissueWeightingFactor)$$

Biological systems rely on a hyper-complex system of molecules and structures to carry out the functions necessary for life. Ionizing radiation can disrupt cellular operations which can lead to a loss of function or death of the cell. Molecules in the body are united by chemical bonds and interact in a well defined sequence, often assisted by enzymes and other biological machinery. Energy released from ionization can break chemical bonds, potentially changing the shape and function of these molecules. The impact on the cell is dependent on which parts of the cell are disrupted and how many events take place in a given amount of time.

One of the most sensitive and critical components of the cell is its DNA (deoxyribonucleic acid), which is involved in cellular replication, transcription, and subsequent translation. If an ionization event takes place in the DNA leading to the ejection of an electron, an electrical charge can form in the DNA. Interactions that take place in this manner are called a direct action, in that the ionization event occurs directly in the DNA or from a neighboring molecule. Approximately ⅔ of free radical generation from X-rays is classified as an indirect action, occurring when an ejected electron strikes a water molecule. This ionizes the water molecule and can lead through a series of steps to the creation of a free radical. Once a free radical is generated, it can react very strongly with other molecules to restore a stable electron configuration. If a free radical interacts with a DNA molecule, it can create an error that does nothing, causes a temporary dysfunction, or destabilizes the cell, leading to eventual cellular death.

Excessive radiation exposure can lead to cell death, which can be manifested in two basic forms. Ionization can disrupt cellular functions to the point where the cell can no longer sustain itself, leading to cell death. Mitotic inhibition can also occur, allowing the cell to function, but no longer replicate. Effects that have an impact on the cellular level can be scaled to the organ, system, or organism level. A dose of 100 gray to the entire body can lead to death within 24 to 48 hours. A whole body dose of 2.5 to 5 gray can produce death within several weeks. Localized radiation exposure to organs and other body parts can lead to focal cellular death and dysfunction, with the impact of damage determined in part by the sensitivity of the tissue type.

Cellular death is only one consequence of exposure to ionizing radiation, alteration of DNA can lead to errors in the DNA blueprint. The development of cancer is a possible outcome of DNA damage to somatic cells. Errors in the DNA can lead to defects in cellular regulation, which can lead to uncontrolled proliferation and the development of cancer. Induction of errors in the DNA of germ cells can lead to heritable defects that may not manifest themselves for generations.

DEI and DEI Systems and Related Methods

Figure 1B:
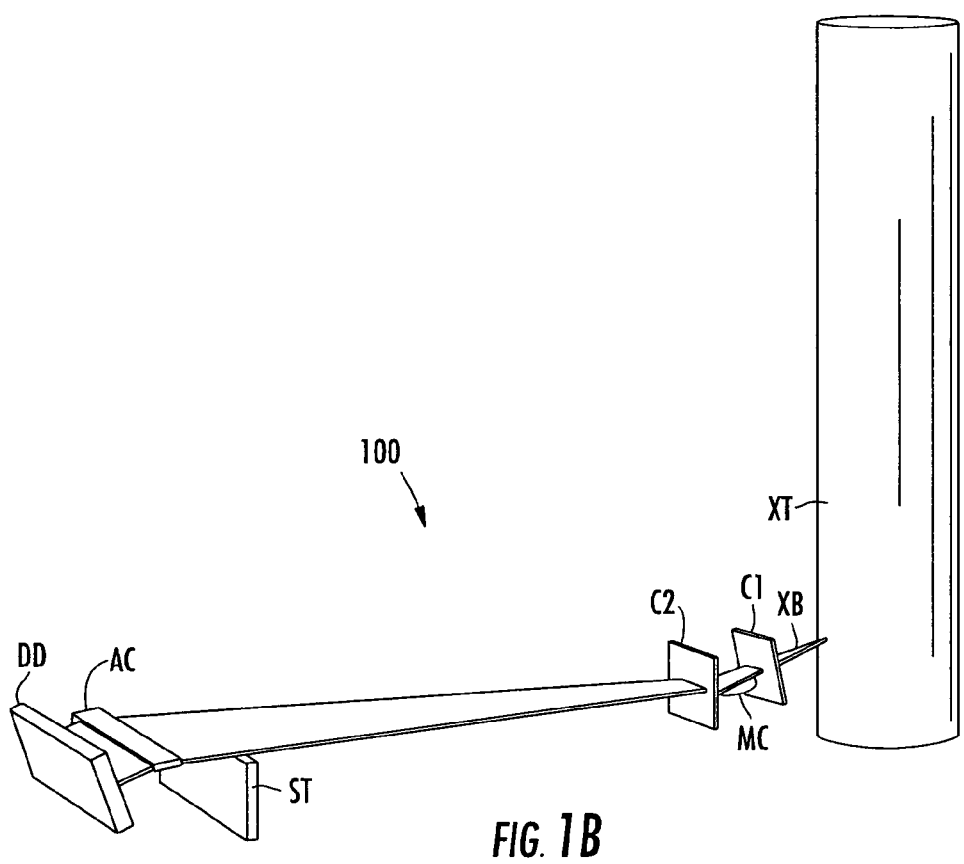
Figure 1C:
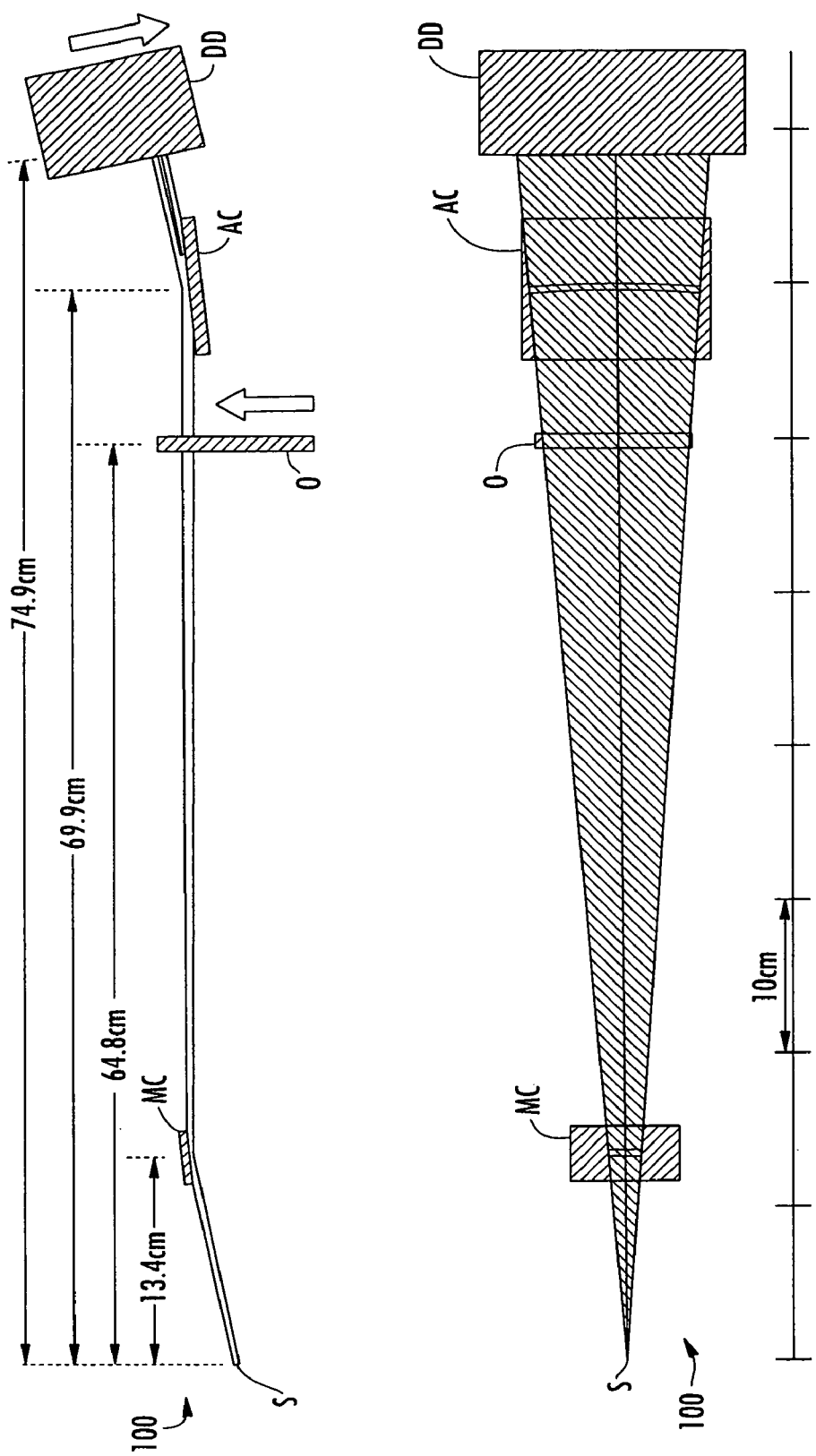
Figure 1D:
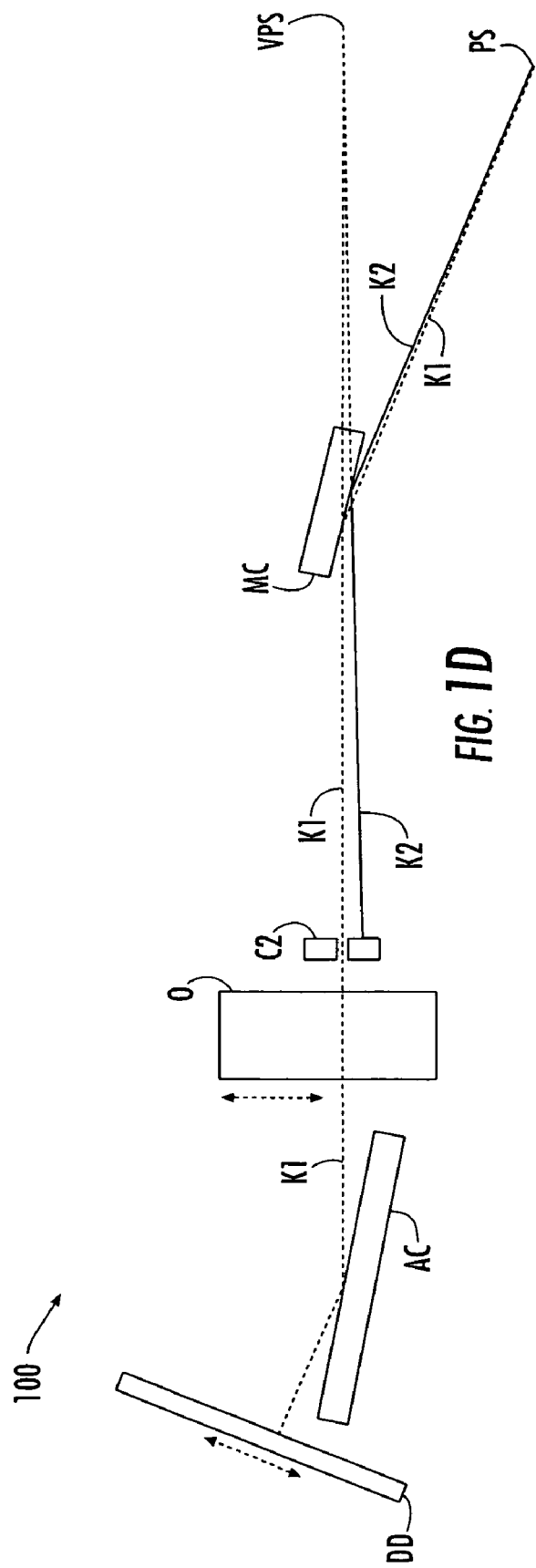
FIGS. 1D and 1E are schematic diagrams of the DEI system shown in FIGS. 1A-1C in different modes of operation according to an embodiment of the subject matter described herein.
Figure 1E:
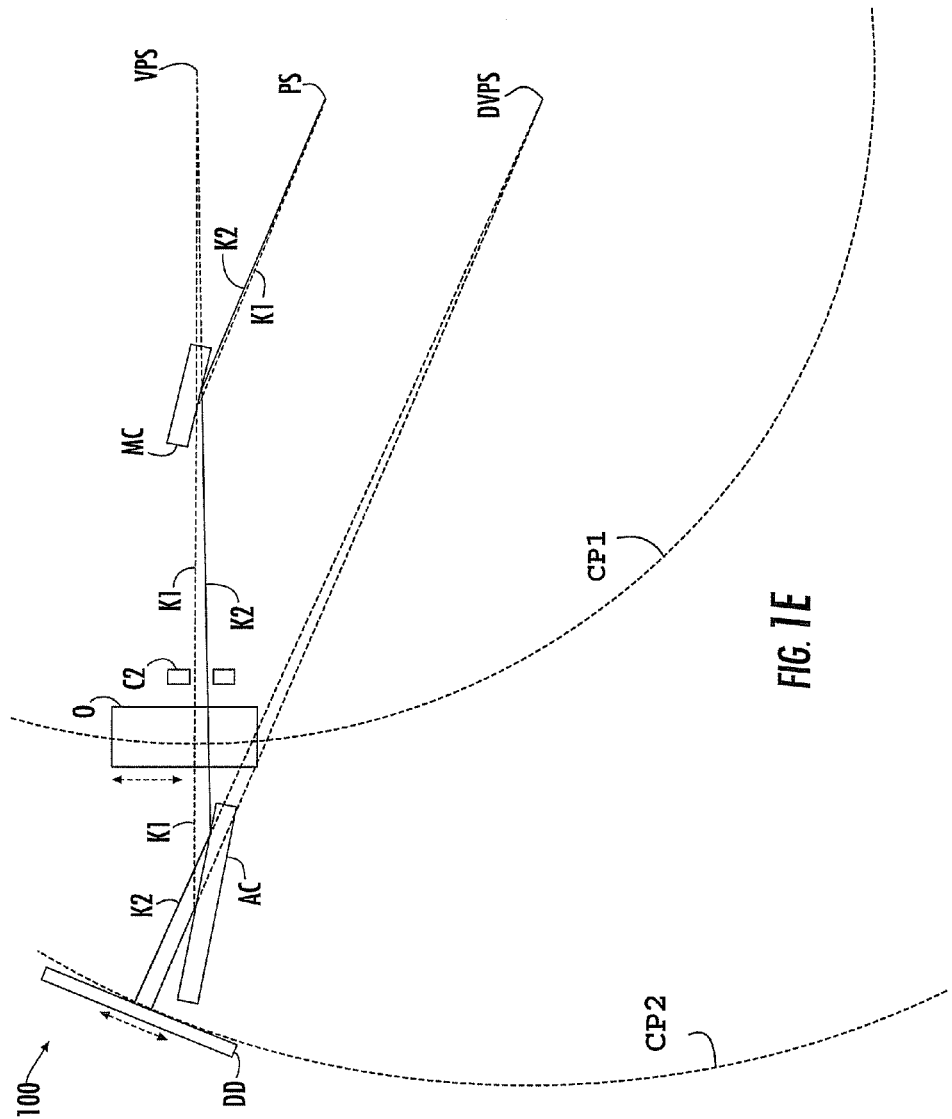

A DEI system according to one embodiment of the subject matter described herein can include a single monochromator crystal for rejecting particular X-rays emitted by an X-ray tube. FIGS. 1A-1C are a schematic diagram, a top perspective view, and a side-top schematic view of a DEI system, generally designated 100, including a single monochromator crystal and operable to produce images of an object O according to an embodiment of the subject matter described herein. Further, FIGS. 1D and 1E are schematic diagrams of DEI system 100 in different modes of operation according to an embodiment of the subject matter described herein. Referring to FIGS. 1A and 1B, DEI system generally designated 100 can include an X-ray tube XT operable to produce a polychromatic X-ray beam, generally designated XB, or a plurality of X-ray beams fanning out in different directions from a point source of X-ray tube XT. X-ray beam XB can include photons having different energies. In one example, X-ray tube XT is a tungsten X-ray tube having a point source from which X-ray beam XB can be emitted.

Figure 2:
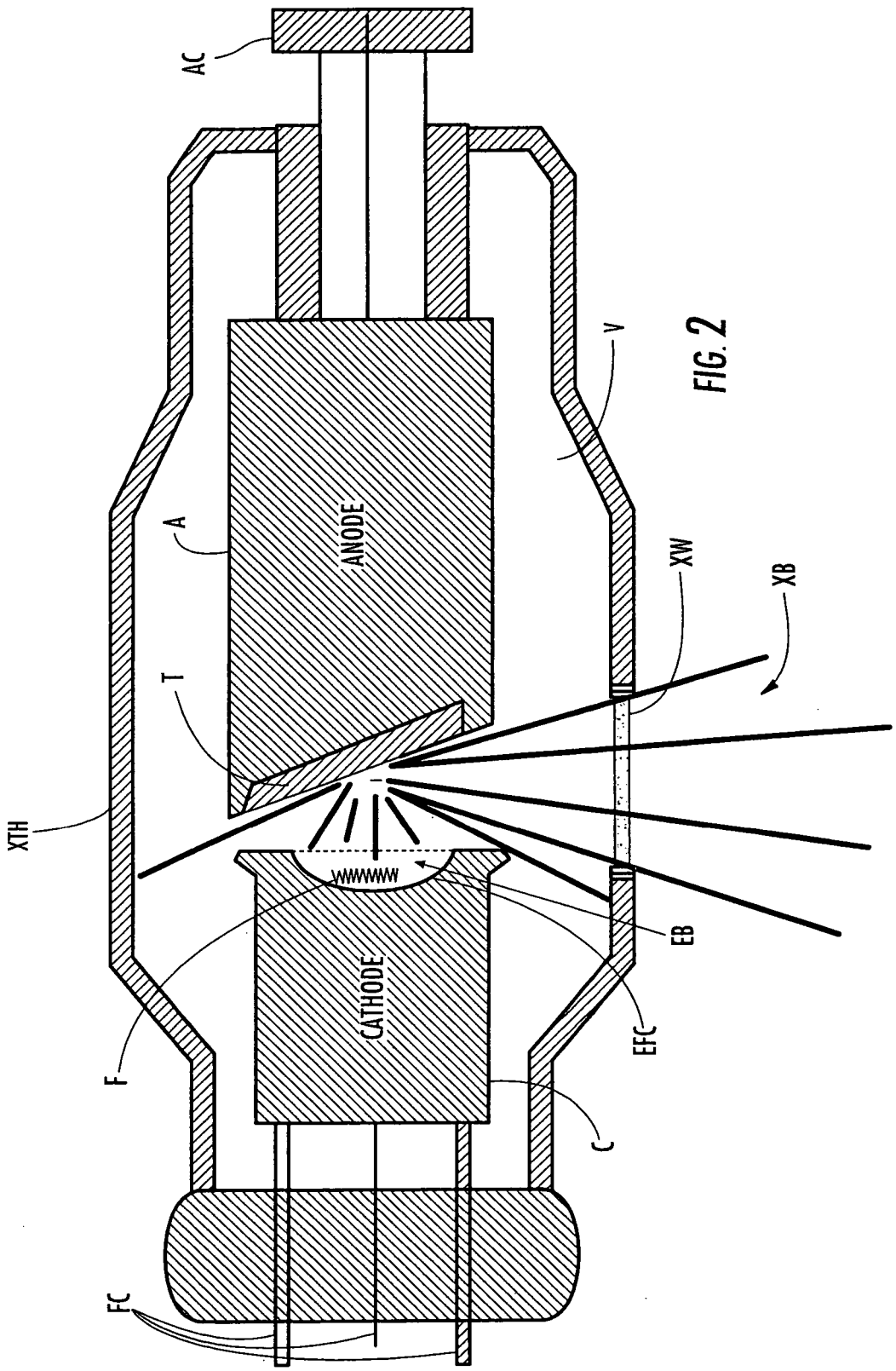
FIG. 2 is a schematic diagram of an X-ray tube based on a cathode/anode tube design according to an embodiment of the subject matter described herein.

FIG. 2 is a schematic diagram of X-ray tube XT based on a stationary X-ray tube design according to an embodiment of the subject matter described herein. Referring to FIG. 2, X-ray tube XT includes a cathode C configured to generate an electron beam, generally designated EB. Cathode C is made of tungsten. A high voltage is applied across cathode C and anode A, which creates a high potential difference across a vacuum interior V of X-ray tube XT. A voltage potential can be applied to anode A via an anode connection ANC. X-ray tube XT can include a filament F configured to heat cathode C. Filament F can be connected to a power supply by filament connections FC.

Vacuum interior V is defined within X-ray tube housing XTH. Electrons may be thermonically ejected from cathode C by heating cathode C. An electrostatic focusing cup EFC surrounds the point of electron ejection, which helps to focus the electron stream towards anode A. Further, electrons being emitted from cathode C are focused across vacuum interior V to anode A, with the velocity across the gap being determined by the voltage applied across the circuit.

Electrons ejected from cathode C can be directed towards and incident upon a tungsten target T of anode A. As a result of the impact of electrons upon target T, X-ray beam XB is generated. X-ray beam XB exits vacuum interior V via an X-ray window XW. X-ray beam XB can include characteristic emission lines and bremsstrahlung radiation.

One example of an X-ray generator is the ISOVOLT TITAN 160 available from GE Inspection Technologies of Ahrensburg, Germany. Other exemplary X-ray tubes include the COMET MXR-160 Series of X-ray tubes, such as the MXR-160HP/20 X-ray tube, which are available from Comet AG of Flamatt, Switzerland. Other exemplary X-ray tubes can include those that use anodes other than tungsten, including molybdenum, iron, and copper. Other suitable types of targets include a barium hexaboride target and a samarium target. A barium hexaboride target can produce X-rays at about 30 keV. Samarium's $K\alpha 1$ line is at about 40 keV. In one example, an anode of an x-ray tube can be a rotating anode from which x-ray beams can be emitted. In another example, an anode of an x-ray tube can be a stationary anode from which x-ray beams can be emitted.

Referring again to FIGS. 1A and 1B, a collimator C1 can be positioned for blocking a portion of X-ray beam XB that fall outside an angular acceptance window of monochromator crystal MC. System 100 can also include additional collimators positioned between X-ray tube XT and monochromator crystal MC for blocking a portion of X-ray beam XB that falls outside an angular acceptance window of monochromator crystal MC. The collimators can define a slit or hole through which a portion of X-ray beam XB can pass to monochromator crystal MC. Further, the collimators can be made of any suitable material for blocking X-ray beams such as lead. A distance X between X-ray tube XT and collimator C1 can be about 100 millimeters (mm).

Monochromator crystal MC can be configured to select a predetermined energy of a portion of X-ray beam XB incident thereon. In one example, monochromator crystal MC is a silicon [333] monochromator crystal adapted to reject the majority of photons of X-ray beam XB that do not have a desired energy. For the case of a tungsten X-ray tube, there can be a range of beam energies that are reflected by the silicon monochromator crystal. In this case, the characteristic emission lines of the X-ray beams are 59.13 keV ($K\alpha 1$) and 57.983 ($K\alpha 2$), and the bremsstrahlung radiation that falls within the narrow angular acceptance window of the monochromator crystal. The brightness of the bremsstrahlung radiation is several orders of magnitude less than the two $K\alpha$ emission lines.

X-ray beam XB are scattered by monochromator crystal MC in several different directions. A collimator C2 can be positioned for blocking a portion of X-ray beam XB that falls outside an angular acceptance window of analyzer crystal AC. Collimator C2 can define a slit or hole through which a portion of X-ray beam XB can pass towards analyzer crystal AC for interception by analyzer crystal AC. In one example, a distance Y between monochromator crystal MC and analyzer crystal AC can be about 500 mm.

Analyzer crystal AC can be rotated for measuring the amount of radiation traveling in a particular direction. The angular sensitivity function of the crystal system is called the intrinsic rocking curve, and this property is used to generate image refraction contrast. If an X-ray photon is deviated towards the peak of the rocking curve, its reflectivity, and this intensity will increase. If an object feature causes a photon to be deflected down the rocking curve, or away from the peak reflectivity position, it will cause a reduction in intensity.

The sample or object can be imaged in air or immersed in a coupling medium, such as water. The use of a coupling medium can be used to reduce the index gradient between the air and the object to be imaged, thus allowing the incident X-rays to pass into the sample without experiencing significant refraction at the air-object interface. This is not necessary for most objects, but it is an application of the DEI method and can be used to improve the internal contrast of an object.

In one example, monochromator crystal MC is a symmetric crystal which is narrow in one dimension. A symmetric crystal's lattice planes (the atomic layers that contribute to diffracting the X-ray beam) are parallel to the surface of the crystal. A symmetric crystal preserves the divergence and size of the incoming beam. In comparison, an asymmetric crystal modifies the divergence and size of the incoming beam. In this example of monochromator crystal MC being a symmetric crystal, two-dimensional imaging of large imaging fields (e.g., imaging fields of about 100 mm by 100 mm) can be achieved by scanning a sample object and a detector using a symmetric crystal. One exemplary advantage of a symmetric crystal over an asymmetric crystal is that the asymmetric crystal requires a large monochromator crystal to prepare the imaging beam (e.g., selecting and collimating X-rays), imposing a severe limitation on the perfection of the large crystal. Further, the size of an asymmetric crystal increases with increasing X-ray beam energy, thus making it impractical for X-rays of about 59.13 keV. In contrast, for example, a symmetric monochromator crystal used in accordance with the subject matter described herein can utilize 59.13 keV X-rays with a modest sized crystal of about 30 mm in length.

Referring again to FIGS. 1A and 1B, an object O can be positioned in the path of X-ray beam XB by a scanning stage ST for imaging of object O. Object O can be scanned perpendicular to the direction of X-ray beam XB as indicated by arrow A. During scanning of object O, X-ray beam XB can pass through object O and can be analyzed by analyzer crystal AC, which can be a silicon [333] crystal that matches monochromator crystal MC. X-ray beam XB incident on analyzer crystal AC can diffract for interception by a digital detector (or image plate) DD. Digital detector DD can detect the intercepted X-ray beam XB and generate electrical signals representative of the intercepted X-ray beams.

In one example, a line source scanning system can be utilized. In one example, the scanning system can have a 1:1 correlation between the object and the detector.

The electrical signals can be communicated to a computer C for image analysis and display to an operator. The image represented by the electrical signals can include contributions from both the $K\alpha 1$ and $K\alpha 2$ energies in the resulting image. In one example, the energy of interest is the $K\alpha 1$ energy of 59.319 keV. In this example, the image features produced by the $K\alpha 2$ energy can be removed via image processing. If features created by the $K\alpha 2$ portion of the X-ray beam are at a distance lower than the resolution desired, then the two can be used together and reduce the overall image time required. For high resolution applications, the $K\alpha 2$ energy portion can cause a shadowing effect and can be removed via image processing. Computer C can be configured to generate an absorption image, an image showing refraction effects, and an image depicting ultra-small-angle scattering, the types of which are described in more detail below.

Referring particularly to FIG. 1B, monochromator crystal MC can propagate x-ray beam XB as a fan beam. The fan beam can be collimated with collimators to shield against undesired x-rays, resulting in clear DEI images and low subject dose. In contrast to a two-dimensional beam, a fan beam can be more readily controlled for the shielding of undesired x-rays.

Referring to FIG. 1C, exemplary distances are shown between a source S of the emission of X-ray radiation from X-ray tube XT (shown in FIGS. 1A and 1B) to monochromator crystal MC, object O, analyzer crystal AC, and detector DD. The components may be spaced from one another at other suitable distances depending upon the application. In this example, DEI system 100 is configured for mammography.

Referring now to FIGS. 1D and 1E, as stated above, these figures show DEI system 100 in different operation modes. Characteristic emission lines K$\alpha$1 K1 and K$\alpha$2 K2 of the X-ray beam are generated by X-ray tube XT. Emission lines K$\alpha$1 K1 and K$\alpha$2 K2 originate from the same point source PS. As stated above, monochromator crystal MC rejects the majority of photons of the X-ray beam that do not have the desired energy. In this case, emission lines K$\alpha$1 K1 and K$\alpha$2 K2 and bremsstrahlung radiation pass monochromator crystal MC and are redirected towards analyzer crystal AC as shown.

Collimator C2 is positioned in a path of emission lines K$\alpha$1 K1 and K$\alpha$2 K2. Collimator C2 defines an adjustable slit through which emission lines can be selectively passed towards analyzer crystal AC. In the first operational mode shown in FIG. 1D, the slit is adjusted for an aperture X, 0.6 mm for a distance of about 400 mm from the point source PS, and positioned such that emission line K$\alpha$1 K1 passes collimator C2 and K$\alpha$2 K2 is blocked. Thus, collimator C2 removes all X-rays except for the X-rays from emission line K$\alpha$1 K1 and a very narrow range of bremsstrahlung radiation. In this mode, the beam is not divergent and thus object O and detector DD are scanned at the same scanning speed, in opposite directions. This mode yields a maximum possible out-of-plane resolution (the direction of DEI's contrast), but at the cost of removing a portion of the X-rays from the X-ray beam, thereby necessitating increased exposure time. The virtual point source for object O is designated VPS.

Referring now to FIG. 1E, in the second operational mode, emission lines K$\alpha$1 K1 and K$\alpha$2 K2 and the bremsstrahlung radiation at nearby energies are passed through collimator C2. The slit of collimator C2 is adjusted for an aperture of X, 2.0 mm at a distance of about 400 mm from the point source PS and positioned such that emission lines K$\alpha$1 K1 and K$\alpha$2 K2 and the bremsstrahlung radiation passes collimator C2. In this mode, the beam divergence is taken into account. In order to avoid image blurring, object O and detector DD can be scanned at the same angular speed. The relative scanning speeds of detector DD and the sample stage on which object O is placed can be determined by the source-to-object distance and the source-to-detector distance (where the distances are taken along the beam path). The beam divergence in this mode can lead to lower resolution out-of-plane, but this mode has the advantage of passing more X-rays and thus allows for a faster exposure time. The virtual point source for detector DD is designated DVPS. Circle portions CP1 and CP2 are centered at the virtual source points for object O and detector DD, respectively.

Further, in one embodiment of using the second mode, the Bremsstrahlung radiation at x-ray energies that are different from the K alpha lines can be captured. Thus, in this embodiment, the system is tunable in x-ray energy and is not limited to the characteristic emission energies. This functionality can be achieved by changing the incident angle of the monochromator crystal and the analyzer crystal. In one example, this functionality can be achieved by changing the incident angle to 11.4 degrees, following the Bragg's law, and replacing the Copper filter with an Aluminum filter. In this example, imaging can occur at 30 keV x-ray energy. X-ray energies lower than the Tungsten emission line energies can be utilized for relatively thin objects.

In one example, the copper filter can be configured to remove about 19 keV bremsstrahlung radiation for reducing or eliminating unwanted crystal reflections and harmonics. Images have the potential to be degraded without this filtering.

Figure 3:
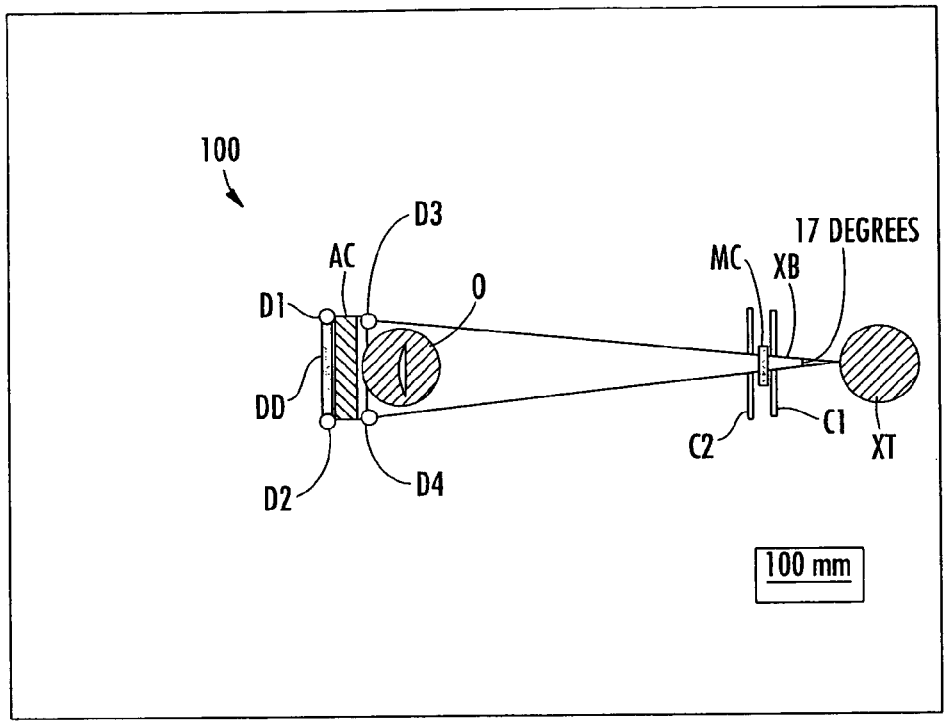
FIG. 3 is a top schematic view of the DEI system of FIGS. 1A-1E according to an embodiment of the subject matter described herein.

FIG. 3 is a top schematic view illustrating DEI system 100 of FIGS. 1A-1E according to an embodiment of the subject matter described herein. Referring to FIG. 3, X-ray beam XB are generated by a source of X-ray tube XT. Collimators C1 and C2 block the spread of the portion of X-ray beam XB that pass towards analyzer crystal AC to an angle of about 5.7 degrees from the source of X-ray tube XT. The portion of X-ray beam XB that passes through collimators C1 and C2 is the X-ray beam portion that passes through slits in the collimators.

System 100 can include right and left analyzer sodium iodide detectors D1 and D2, respectively, and right and left monochromator sodium iodide detectors D3 and D4, respectively. Detectors D1-D4 are configured for analyzer alignment. These detectors are used to measure the intensity of the diffracted X-ray beam being emitted from the monochromator crystal MC, or the analyzer AC. For system alignment, detectors D1 and D2 are placed in the post analyzer crystal AC X-ray beam XB. If the analyzer crystal is not tuned to the desired angle, the intensity measured by the detectors D1 and D2 will show this and the system can be adjusted. The same is true for the detectors in the post-monochromator crystal MC X-ray beam XB. In addition, detectors D1-D4 can be used to measure X-ray beam XB in real time and adjust the analyzer crystal, D1 and D2, chi (angle as measured about the axis along the X-ray beam path) or monochromator crystal chi, D3 and D4. The use of these detectors to set, measure, and adjust the analyzer crystal AC and monochromator crystal MC can be important for successful DEI image acquisition.

Figure 4:
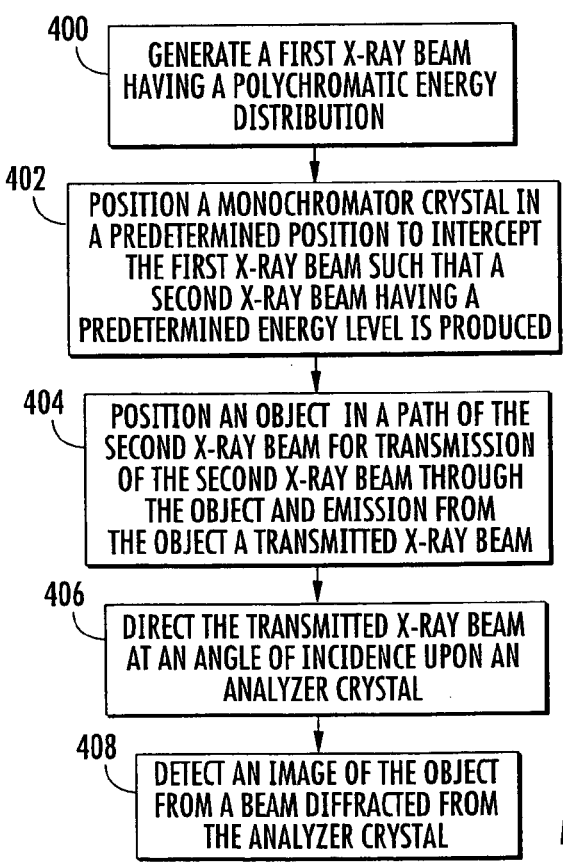
FIG. 4 is a flow chart of an exemplary process for imaging an object by use of DEI system of FIGS. 1A-1E according to an embodiment of the subject matter described herein.

FIG. 4 is a flow chart illustrating an exemplary process for imaging object O by use of DEI system 100 shown in FIGS. 1A-1E according to an embodiment of the subject matter described herein. Referring to FIG. 4, in block 400, a first X-ray beam can be generated that has a polychromatic energy distribution. For example, X-ray beam XB generated by X-ray tube XT can have a polychromatic energy distribution. Further, for example, X-ray tube XT can be set to a power of at least 50 kW for generating the X-ray beam. In the alternative, for example, the power of X-ray tube XT can be set to less than 50 kW (such as about 30 kW) for some medial applications, research and development, small animal imaging, etc. The advantage of using less power is a reduced cost. The first X-ray beam can have a beam energy ranging from about 10 keV to about 60 keV. In one example, the first X-ray beam can be generated by a synchrotron.

In block 402, monochromator crystal MC can be positioned in a predetermined position to intercept the first X-ray beam such that a second X-ray beam having a predetermined energy level is produced. For example, a surface of monochromator crystal MC can be positioned in the path of X-ray beam. XB for intercepting the beam. As stated above, monochromator crystal MC can be adapted to reject the majority of photons of X-ray beam XB that do not have a desired energy. Thus, a resulting second X-ray beam can be produced that has the predetermined energy level. In one example, a surface of monochromator crystal MC can be positioned at an angle of between about 5 degrees and 20 degrees with respect to a path of X-ray beam XB incident upon the surface of monochromator crystal MC. In this example, these angles may be used for [333] reflection. Alternatively, other suitable angles may be used in the positioning of the surface of monochromator crystal MC. In another example, a surface of monochromator crystal MC can be positioned at an angle of between about 1 degrees and 20 degrees with respect to a path of X-ray beam XB incident upon the surface of monochromator crystal MC. In another example, a surface of monochromator crystal MC can be positioned at an angle of between about 1 degree and 20 degrees with respect to a path of X-ray beam XB incident upon the surface of monochromator crystal MC. If both [333] and [111] reflections are used, the angular range can be between about 1 degree and about 40 degrees for the energy range of 10 to 70 keV.

In block 404, object O can be positioned in a path of the second X-ray beam for transmission of the second X-ray beam through object O and emission of a transmitted beam from object O. For example, object O can be positioned on scanning stage ST for movement of object O into the pathway of the X-ray beam.

In block 406, the transmitted X-ray beam can be directed at an angle of incidence upon analyzer crystal AC. For example, analyzer crystal AC can be positioned in the path of the transmitted X-ray beam and at an angle for intercepting the X-ray beam at an angle of incidence. At least a portion of the beam intercepting analyzer crystal AC can be diffracted towards detector DD.

In block 408, an image of object O can be detected from the beam diffracted from analyzer crystal AC. For example, detector DD can detect the diffracted beam from analyzer crystal AC. The diffracted beam can be detected by one of the following exemplary detectors: a detector configured to digitize a detected image; a radiograph film; and an image plate. In one example, the image of an object can be detected from a beam diffracted from a crystal analyzer at a peak of a rocking curve of the crystal analyzer and/or near a peak of a rocking curve of the crystal analyzer. The detected image can be processed and presented to a user via a computer C for presentation to a user.

In another example of detecting the image of the object, a first angle image of object O can be detected from a first diffracted beam emitted from analyzer crystal AC positioned at a first angular position. The first angle image of object O can be detected at a low rocking curve angle setting of analyzer crystal AC. Further, a second angle image of object O can be detected from a second diffracted beam emitted from analyzer crystal AC positioned at a second angular position. The second angle image of object O can be detected at a high rocking curve angle setting of analyzer crystal AC. The first and second angle images can be combined by computer C to derive a refraction image. Further, computer C can derive a mass density image of object O from the refraction image. The mass density image can be presented to a user via a display of computer C.

Figure 5:
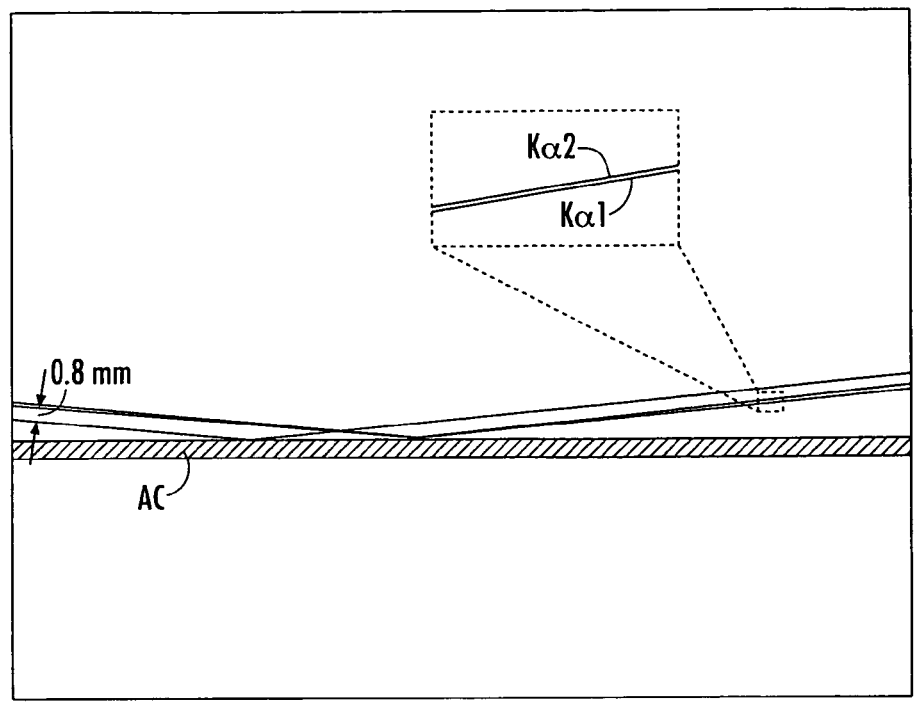
FIG. 5 is a side view of an analyzer crystal of DEI system shown in FIGS. 1A-1E, and 3 according to an embodiment of the subject matter described herein.

FIG. 5 is a side view of analyzer crystal AC of DEI system 100 shown in FIGS. 1A-1E, and 3 according to an embodiment of the subject matter described herein. Referring to FIG. 5, the diffraction of characteristic emission lines $K\alpha 1$ and $K\alpha 2$ from the surface of analyzer crystal AC are shown. The accommodation of more than one x-ray energy can result in improved X-ray flux.

Figure 6A:
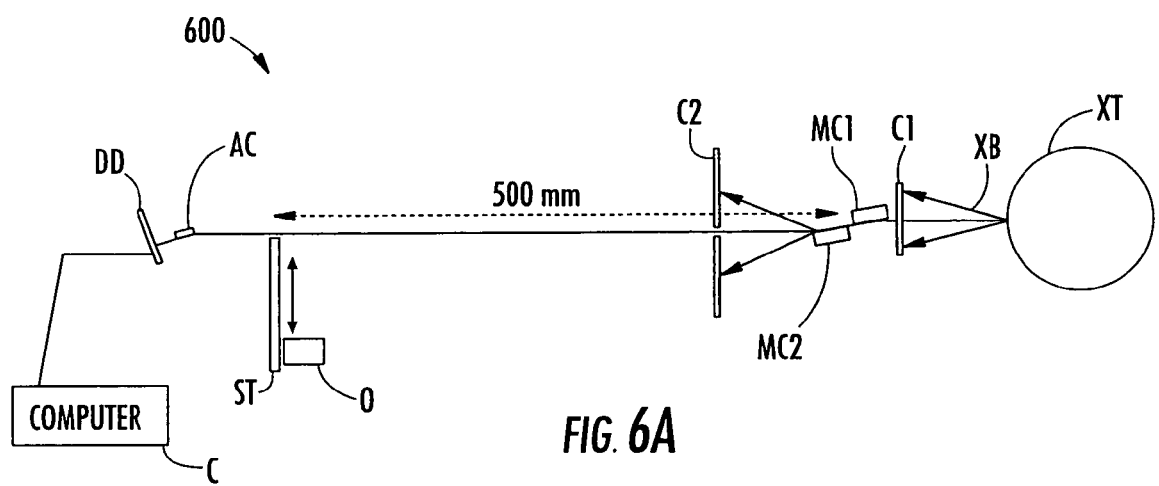
FIGS. 6A and 6B are a schematic diagram and a top perspective view, respectively, of a DEI system including mismatched monochromator crystals and operable to produce images of an object according to an embodiment of the subject matter described herein.
Figure 6B:
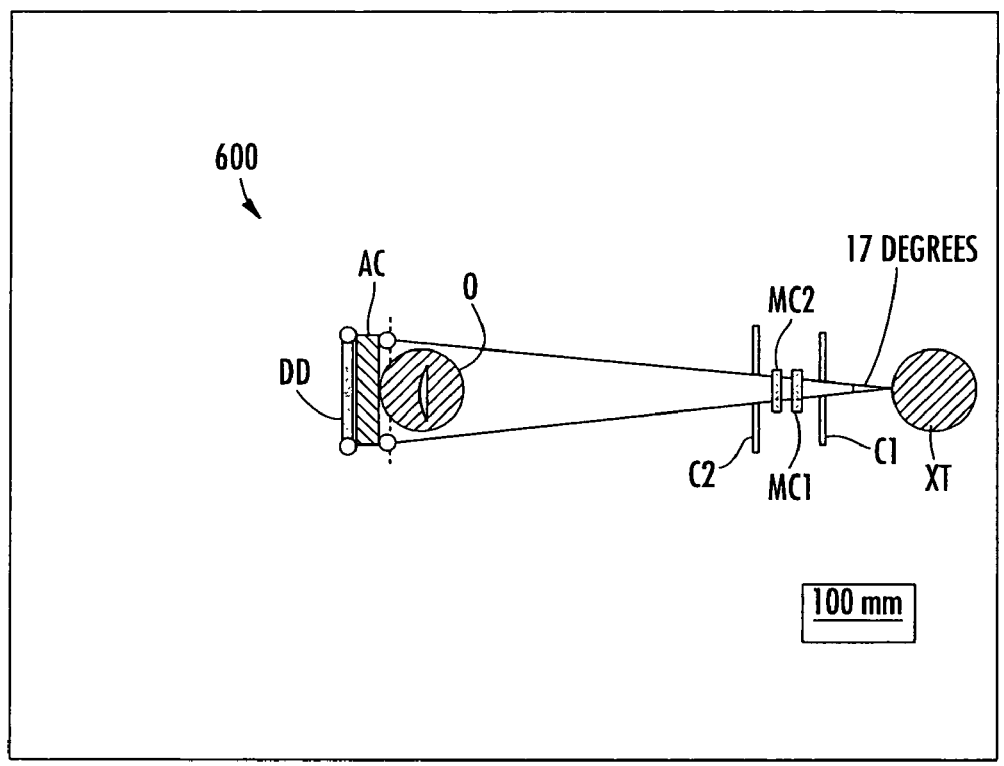

In another embodiment, a DEI system in accordance with the subject matter described herein can include a mismatch crystal design for rejecting particular X-rays emitted by an X-ray tube. In this design, the $K\alpha 2$ emission line of the X-ray beam can be eliminated at the monochromator. FIGS. 6A and 6B are a schematic diagram and a top perspective view, respectively, of a DEI system, generally designated 600, including mismatched monochromator crystals and operable to produce images of an object O according to an embodiment of the subject matter described herein. Referring to FIGS. 6A and 6B, DEI system 600 includes X-ray tube XT operable to produce X-ray beam XB. Collimator C1 can be positioned for blocking a portion of X-ray beam XB that fall outside an angular acceptance window of a first monochromator crystal MC1. The unblocked portion of X-ray beam XB can intercept first monochromator crystal MC1, which refracts the unblocked portion in a direction for intercept by a second monochromator crystal MC2. First monochromator crystal MC1 can be tuned to a particular angle using Bragg's Law to select a very narrow range of photon energies for resulting in a diffracted monochromatic beam directed towards second monochromator crystal MC2. Because of the divergence of X-ray beam XB from X-ray tube XT, first monochromator crystal MC1 can diffract a range of energies which can include the characteristic emission lines $K\alpha 1$ and $K\alpha 2$ and bremsstrahlung radiation at nearby energies. A function of second monochromator crystal MC2 is to redirect the beam to a direction parallel to the incident beam and aligned with analyzer crystal AC. When tuning the system for a particular energy, the first monochromator crystal is aligned first, and then the second crystal is tuned to find the position of the beam.

With second monochromator crystal. MC2 aligned, analyzer crystal AC is scanned to find the position of the beam on the crystal. Rocking the crystal to find the beam position is analogous to scanning a radio dial to find a particular station, generating a sharp rise in intensity when the angular position of the analyzer is in perfect alignment with the second monochromator crystal. Once analyzer crystal AC is aligned, the system is tuned and ready for use.

First and second monochromator crystals MC1 and MC2, respectively, can be configured in a mismatch crystal design for rejecting particular X-rays emitted by an X-ray tube. Monochromator crystals MC1 and MC2 can be used to eliminate the $K\alpha 2$ emission line of X-ray beam XB, which can be achieved by utilizing the angular acceptance versus energy for different crystals. In one example, monochromator crystals MC1 and MC2 can be germanium [333] and silicon [333] monochromator crystals, respectively.

Figure 7:
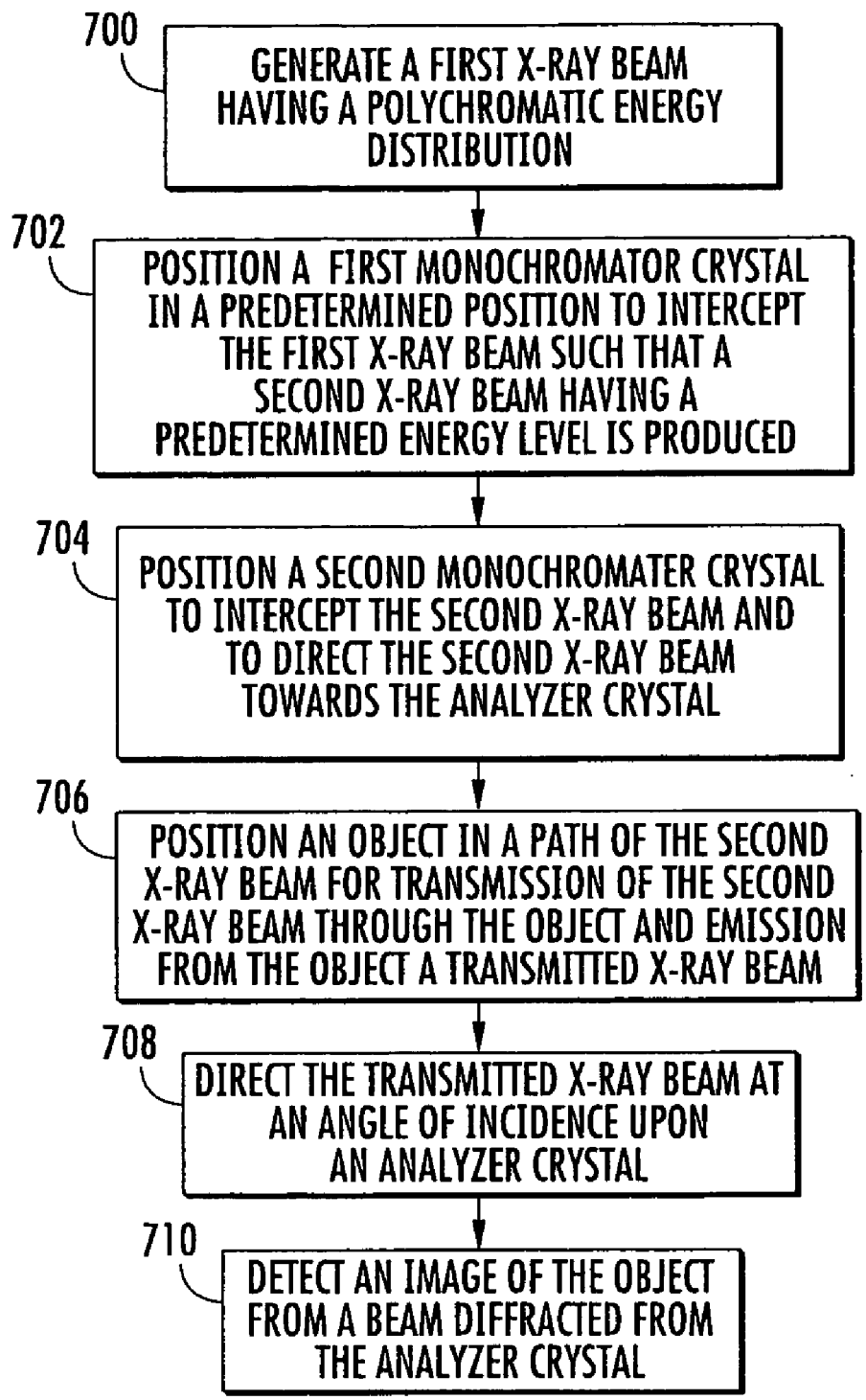
FIG. 7 is a flow chart of an exemplary process for imaging an object by use of the DEI system of FIGS. 6A and 6B according to an embodiment of the subject matter described herein.

FIG. 7 is a flow chart illustrating an exemplary process for imaging object O by use of DEI system 600 shown in FIGS. 6A and 6B according to an embodiment of the subject matter described herein. Referring to FIG. 7, in block 700, a first X-ray beam can be generated that has a polychromatic energy distribution. For example, X-ray beam XB generated by X-ray tube XT can have a polychromatic energy distribution. Further, for example, X-ray tube XT can be set to a power of at least 50 kW for generating the X-ray beam. The first X-ray beam can have a beam energy ranging from about 10 keV to about 60 keV. In one example, the first X-ray beam can be generated by a synchrotron.

In block 702, monochromator crystal MC1 can be positioned in a predetermined position to intercept the first X-ray beam such that a second X-ray beam having a predetermined energy level is produced. For example, a surface of monochromator crystal MC1 can be positioned in the path of X-ray beam XB for intercepting the beam. As stated above, monochromator crystal MC1 can be adapted to reject the majority of photons of X-ray beam XB that do not have a desired energy. Thus, a resulting second X-ray beam can be produced that has the predetermined energy level. In one example, a surface of monochromator crystal MC1 can be positioned at an angle of between about 5 degrees and 20 degrees with respect to a path of X-ray beam XB incident upon the surface of monochromator crystal MC1.

In block 704, monochromator crystal MC2 can be positioned to intercept the second X-ray beam and to direct the second X-ray beam towards analyzer crystal AC. In one example, second monochromator crystal MC2 can be positioned such that the second X-ray beam is directed along a path parallel to a path of the portion of X-ray beam XB passing through collimator C1. In another example, monochromator crystals MC1 and MC2 can be mismatched. In another example, monochromator crystals MC1 and MC2 can be selected for rejecting a predetermined portion of X-ray beam XB. In another example, monochromator crystals MC1 and MC2 can be one of germanium [333] and silicon [333] monochromator crystals.

In block 706, object O can be positioned in a path of the second X-ray beam for transmission of the second X-ray beam through object O and emission of a transmitted beam from object O. For example, object O can be positioned on a scanning stage for movement of object O into the pathway of the X-ray beam.

In block 708, the transmitted X-ray beam can be directed at an angle of incidence upon analyzer crystal AC. For example, analyzer crystal AC can be positioned in the path of the transmitted X-ray beam and at an angle for intercepting the X-ray beam at an angle of incidence. At least a portion of the beam intercepting analyzer crystal AC can be diffracted towards detector DD.

In block 710, an image of object O can be detected from the beam diffracted from analyzer crystal AC. For example, detector DD can detect the diffracted beam from analyzer crystal AC. The diffracted beam can be detected by one of the following exemplary detectors: a detector configured to digitize a detected image; a radiograph film; and an image plate. In one example, the image of an object can be detected from a beam diffracted from a crystal analyzer at a peak of a rocking curve of the crystal analyzer and/or near a peak of a rocking curve of the crystal analyzer. In this example, the peaks can occur within approximately one-half of a Darwin width of the rocking curve. The detected image can be processed and presented to a user via a computer C for presentation to a user.

In another example of detecting the image of the object, a first angle image of object O can be detected from a first diffracted beam emitted from analyzer crystal AC positioned at a first angular position. The first angle image of object O can be detected at a low rocking curve angle setting of analyzer crystal AC. Further, a second angle image of object O can be detected from a second diffracted beam emitted from analyzer crystal AC positioned at a second angular position. The second angle image of object O can be detected at a high rocking curve angle setting of analyzer crystal AC. The first and second angle images can be combined by computer C to derive a refraction image. Further, computer C can derive a mass density image of object O from the refraction image. The mass density image can be presented to a user via a display of computer C.

Figure 8:
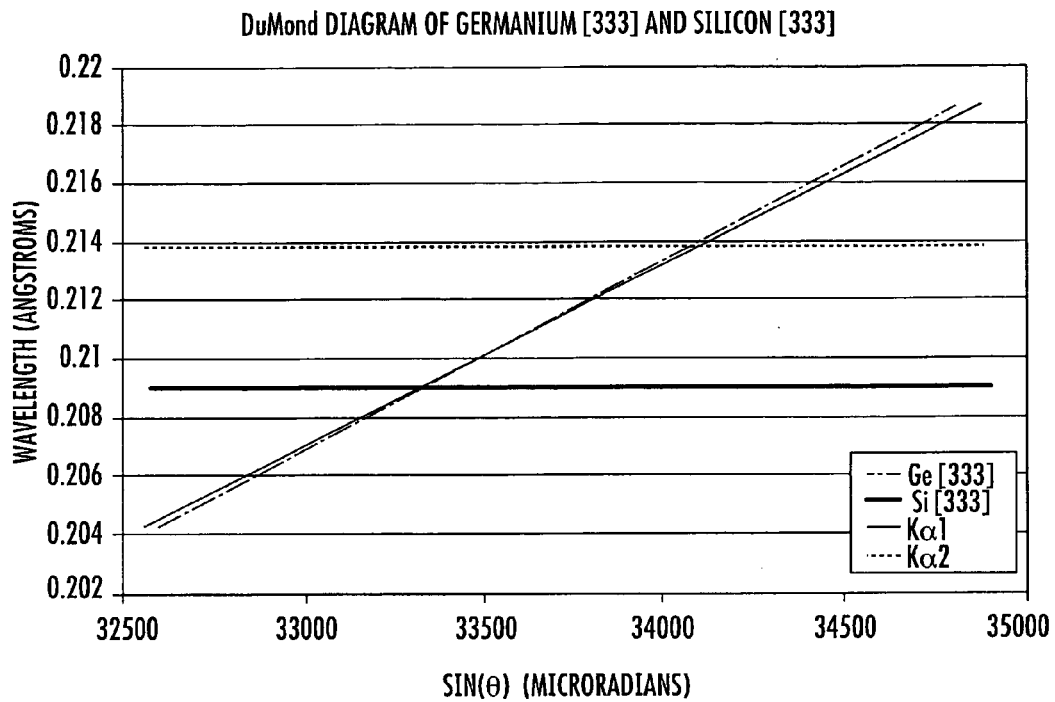
FIGS. 8-10 are graphs of Dumond diagrams of germanium [333] and silicon [333] crystals at different wavelengths.
Figure 9:
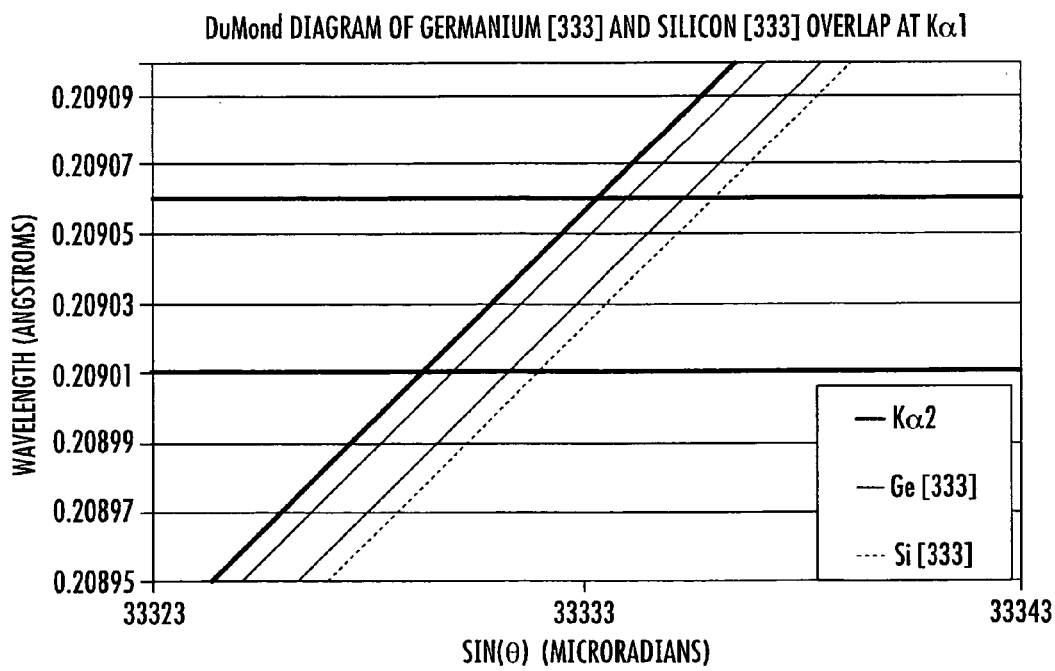
Figure 10:
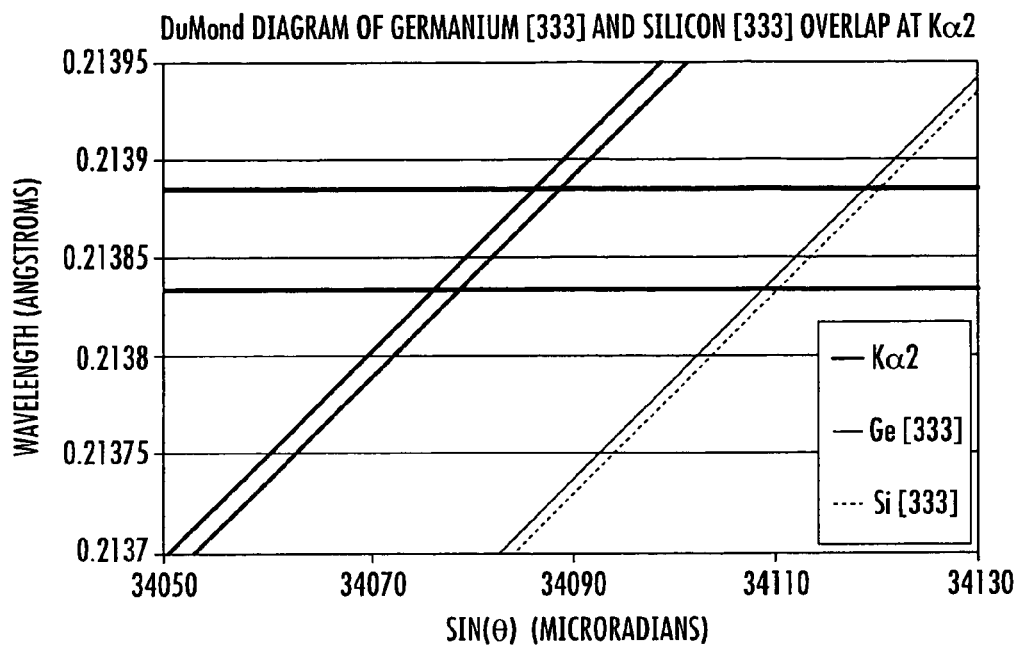

FIGS. 8-10 are graphs of Dumond diagrams of germanium [333] and silicon [333] crystals at different wavelengths. In particular, FIG. 8 is a graph of a Dumond diagram of germanium [333] and silicon [333] crystals in the range of wavelengths corresponding to the $K\alpha 1$ and $K\alpha 2$ of tungsten. FIG. 9 is a graph of a Dumond diagram of germanium [333] and silicon [333] crystals in the range of wavelengths corresponding to the $K\alpha 1$ of tungsten. At the wavelength corresponding to $K\alpha 1$ of tungsten (59.319 keV), there is a complete overlap of the germanium [333] and silicon [333], thus indicating that there is no rejection of the $K\alpha 1$ energy as it diffracts across the first intercepted crystal (i.e., a germanium monochromator crystal) and the second intercepted crystal (i.e., a silicon monochromator crystal). However, at higher wavelengths, there is a separation of the wavelengths that will be accepted for each crystal at a given angle. Referring to FIG. 10, at the wavelength corresponding to the $K\alpha 2$ of tungsten (57.982 keV), there is no overlap in the wavelength acceptance of germanium [333] and silicon [333]. Applying this to a tungsten-based source as described with respect to the example shown in FIGS. 6A and 6B, germanium and silicon monochromator crystals can be positioned in parallel geometry to allow the nearly lossless reflection of the $K\alpha 1$ wavelength and completely reject the $K\alpha 2$ wavelength.

Figure 11:
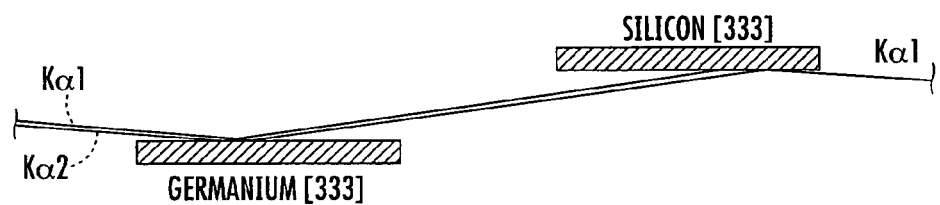
FIG. 11 is a side view of a germanium monochromator crystal and a silicon monochromator crystal of the DEI system shown in FIGS. 6A and 6B according to an embodiment of the subject matter described herein.

FIG. 11 is a side view of germanium monochromator crystal MC1 and silicon monochromator crystal MC2 of DEI system 600 shown in FIGS. 6A and 6B according to an embodiment of the subject matter described herein. Referring to FIG. 11, monochromator crystals MC1 and MC2 are shown in a parallel geometry to provide for the nearly lossless reflection of $K\alpha 1$ wavelength and completely reject the $K\alpha 2$ wavelength for a tungsten X-ray tube.

Referring again to FIGS. 6A and 6B, the portion of X-ray beam XB passing monochromator crystals MC1 and MC2 is scattered in several different directions. A collimator C2 can include a slit or hole positioned for blocking a portion of X-ray beam XB that falls outside an angular acceptance window of analyzer crystal AC.

Object O can be positioned in the path of X-ray beam XB for imaging by a scanning stage ST. During scanning of object O, X-ray beam XB can pass through object O and can be analyzed by analyzer crystal AC, which can be a silicon [333] crystal that matches monochromator crystal MC2. X-ray beam XB incident on analyzer crystal AC can diffract for interception by digital detector DD. Digital detector DD can detect the intercepted X-ray beam XB and generate electrical signals representative of the intercepted X-ray beams for communication to computer C. Computer C can analyze the signal representation and display an image of object O to an operator. In particular, computer C can be configured to generate an absorption image, an image showing refraction effects, and an image depicting ultra-small-angle scattering, the types of which are described in more detail below.

Figure 12:
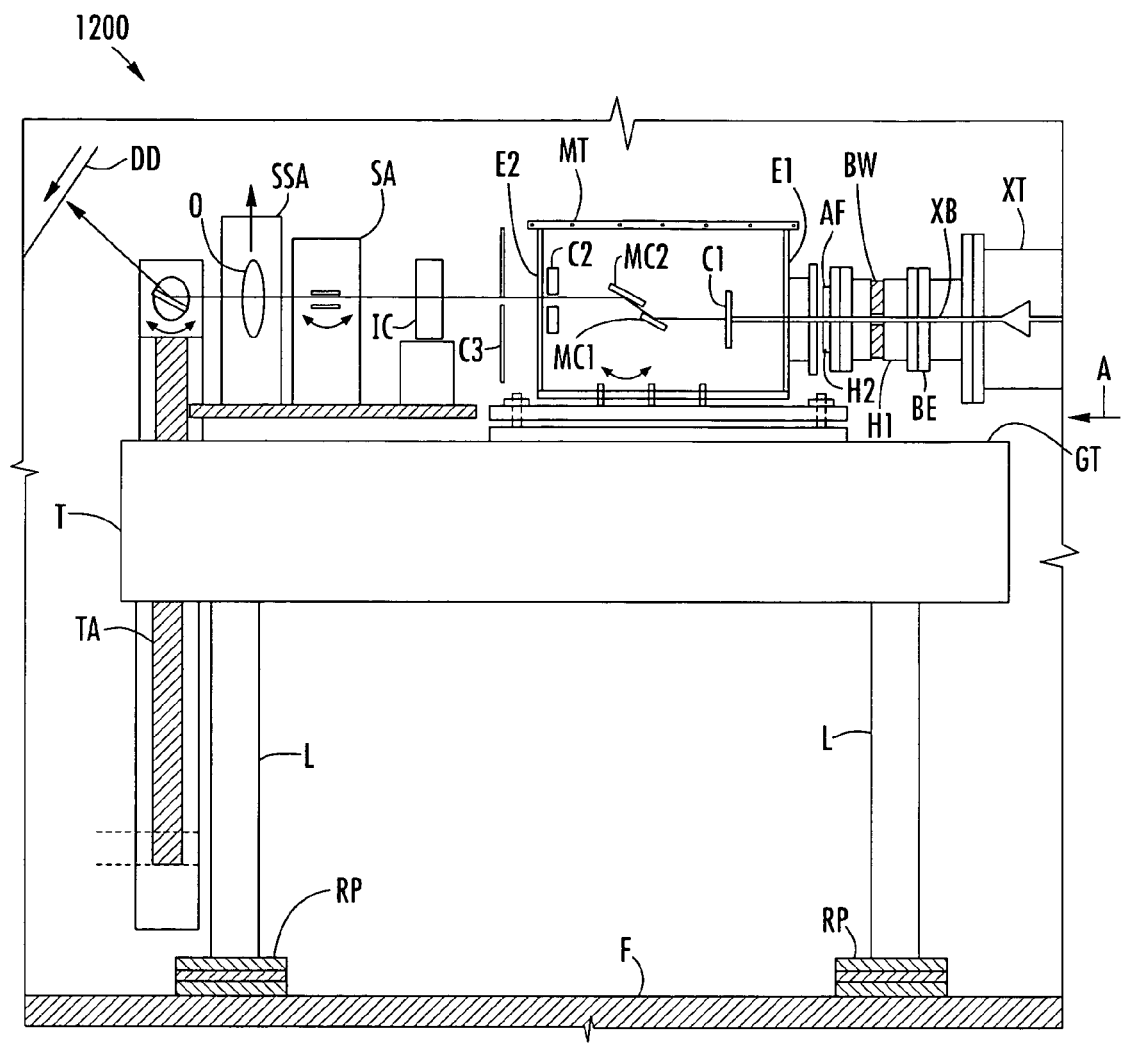
FIG. 12 is a schematic diagram of a DEI system including mismatched monochromator crystals and operable to produce images of an object according to an embodiment of the subject matter described herein.

FIG. 12 is a schematic diagram of a DEI system, generally designated 1200, including mismatched monochromator crystals and operable to produce images of object O according to an embodiment of the subject matter described herein. Referring to FIG. 12, DEI system 1200 can include a tungsten X-ray tube XT operable to produce X-ray beam XB generally directed in the direction indicated by arrow A. A beryllium (Be) window BW can be positioned at a beam exit end BE of X-ray tube XT for intercepting X-ray beam XB. Functions of Be window BW include filtering of low energy X-rays and sealing the vacuum interior of X-ray tube XT. Be window BW can be held in a housing H1 configured for attachment to beam exit end BE.

An aluminum (Al) filter AF can be positioned downstream from Be window BW for intercepting X-ray beam XB passing through Be window BE. Al filter AF can be held in a housing H2 configured for attachment to housing H1 of Be window BW. An Al filter AF is used to attenuate undesired lower energy X-rays.

A monochromator tank MT can be positioned downstream from Al filter AF for intercepting X-ray beam XB passing through Al filter AF. Monochromator tank MT can include mismatched first and second monochromator crystals MC1 and MC2, respectively, and a pair of collimators C1 and C2 that each define a slit through which X-ray beam XB can pass. Monochromator tank MT can include ends E1 and E2 for entry and exit, respectively, of X-ray beam XB. Collimators C1 and C2 can collimate a portion of X-ray beam XB. First and second monochromator crystals MC1 and MC2, respectively, can be configured in a mismatch crystal design for rejecting particular X-rays emitted by an X-ray tube. Monochromator crystals MC1 and MC2 can be used to eliminate the K$\alpha$2 emission line of X-ray beam XB. In one example, monochromator crystals MC1 and MC2 can be germanium [333] and silicon [333] monochromator crystals, respectively. Monochromator tank MT can house mechanisms for rotating monochromator crystals MC1 and MC2 as described herein for selecting an energy of X-ray beam XB.

System 1200 can include another collimator C3, an ion chamber IC, and a shutter assembly SA positioned downstream from monochromator tank MT. On exiting end E2 of monochromator tank MT, at least a portion of X-ray beam XB can pass through a slit defined within collimator C3 positioned downstream from monochromator tank MT for X-ray beam collimation and for blocking a portion of X-ray beam XB. Ion chamber IC is used to measure the X-ray flux using the principle that X-ray photons passing through the chamber can ionize and create a voltage. Shutter assembly SA can be operated to selectively block and pass X-ray beam XB, thus providing for the selective exposure of object O to X-ray beam XB.

Object O can be held by a scanning stage assembly SSA for scanning across the path of X-ray beam XB during imaging. During scanning of object O, X-ray beam XB can pass through object O and can be analyzed by analyzer crystal AC, which can be a silicon [333] crystal that can match second monochromator crystal MC2. Analyzer crystal AC can be rotatable to an appropriate angle with respect to monochromator crystal MC2 as described herein. X-ray beam XB incident on analyzer crystal AC can diffract for interception by a moveable digital detector DD. Digital detector DD can detect the intercepted X-ray beam XB and generate electrical signals representative of the intercepted X-ray beams for communication to computer C. Computer C can analyze the signal representation and display an image of object O to an operator. In particular, computer C can be configured to generate an absorption image and an image showing refraction effects, the types of which are described in more detail below. DEI system 1200 can also be modified in accordance with DEI techniques for displaying an image showing ultra-small angle scattering effects.

A table T can include a granite top GT having a top surface on which monochromator tank MT, collimator C3, ion chamber IC, and shutter assembly SA can be positioned. Table T can include a plurality of legs L that each include a rubber pad RP positioned between a bottom end and a floor F to dampen vibrations for stabilizing system 1200, as described in further detail below. Table T can include a tangent arm TA configured to move analyzer crystal AC up and down in a vertical direction.

Figure 13:
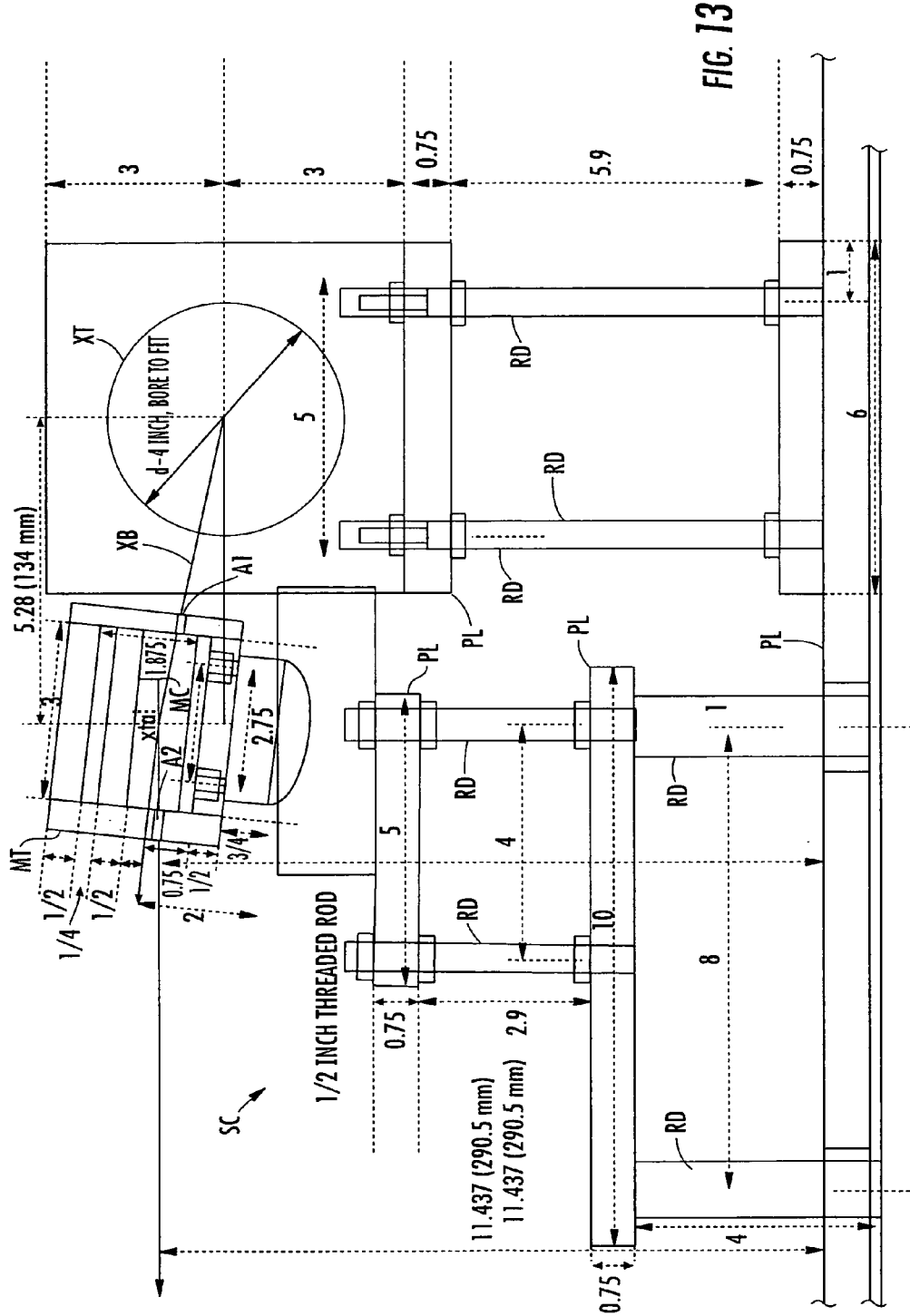
FIGS. 13-16 are schematic diagrams of an exemplary arrangement of an X-ray tube and a monochromator tank having a single monochromator crystal on a scaffold according to an embodiment of the subject matter described herein.

FIGS. 13-16 are schematic diagrams of an exemplary arrangement of X-ray tube XT and monochromator tank MT having a single monochromator crystal MC on a scaffold, generally designated SC, according to an embodiment of the subject matter described herein. In particular, FIG. 13 is a schematic diagram of a side view of the exemplary arrangement. Referring to FIG. 13, scaffold SC includes a plurality of platforms PL and rods RD attached to one another for positioning X-ray tube XT (a portion of which is positioned within the bore indicated by reference label XT) with respect to monochromator tank MT. X-ray tube XT and monochromator tank MT can be precisely positioned with respect to one another such that X-ray beam XB emitted from X-ray tube XT can enter monochromator tank MT through an aperture A1 and such that X-ray beam XB fall within the angular acceptance window of monochromator crystal MC. X-ray beam XB diffracting from monochromator crystal MC can exit monochromator tank MT through aperture A2. The distances indicated by numbers in FIGS. 13-16 are in inches unless otherwise indicated.

Figure 14:
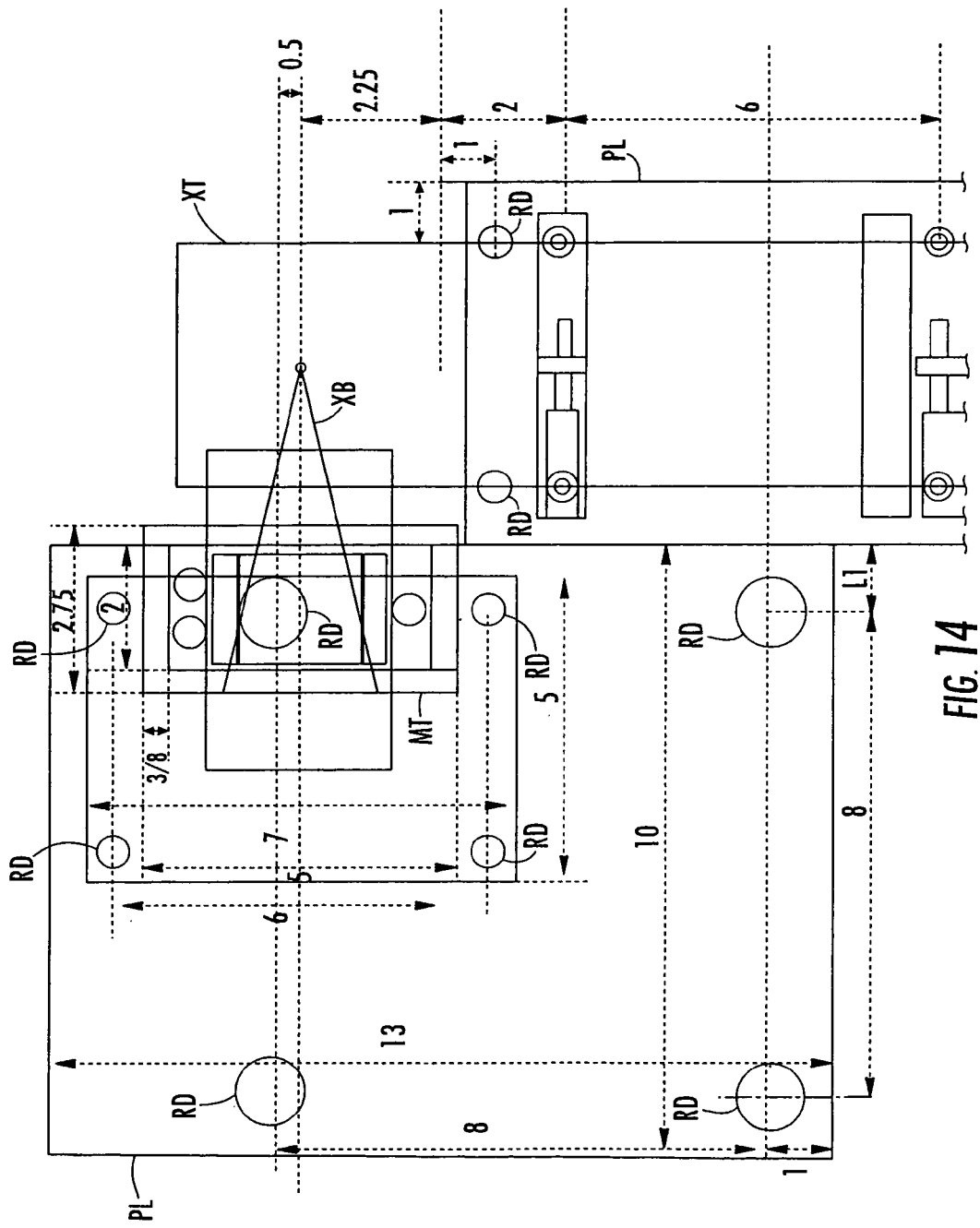

FIG. 14 is a schematic diagram of a top view of the exemplary arrangement shown in FIG. 13. Referring to FIG. 14, X-ray beam XB are shown forming a fan shape extending from a point P within X-ray tube XT.

Figure 15:
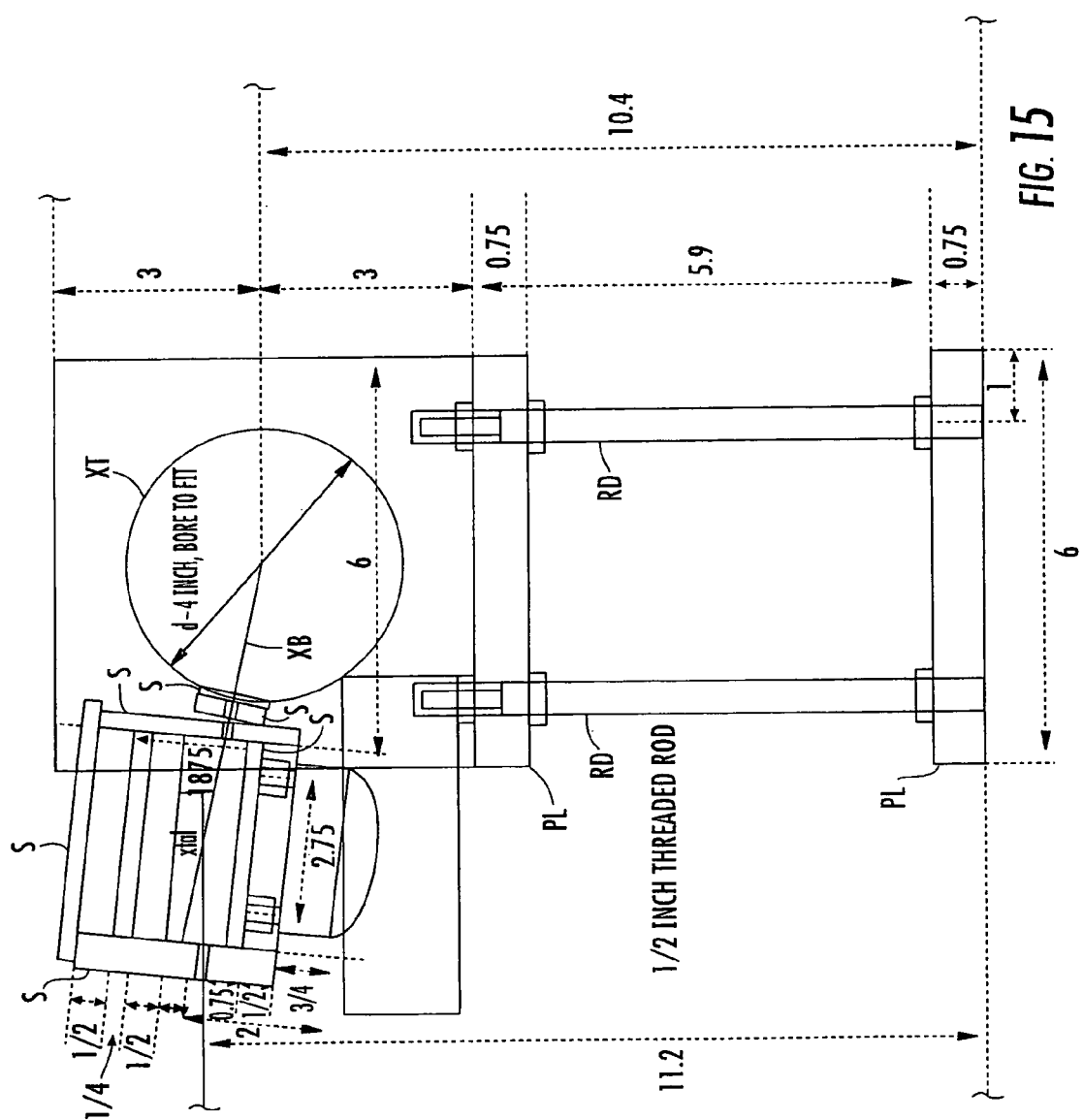
Figure 16:
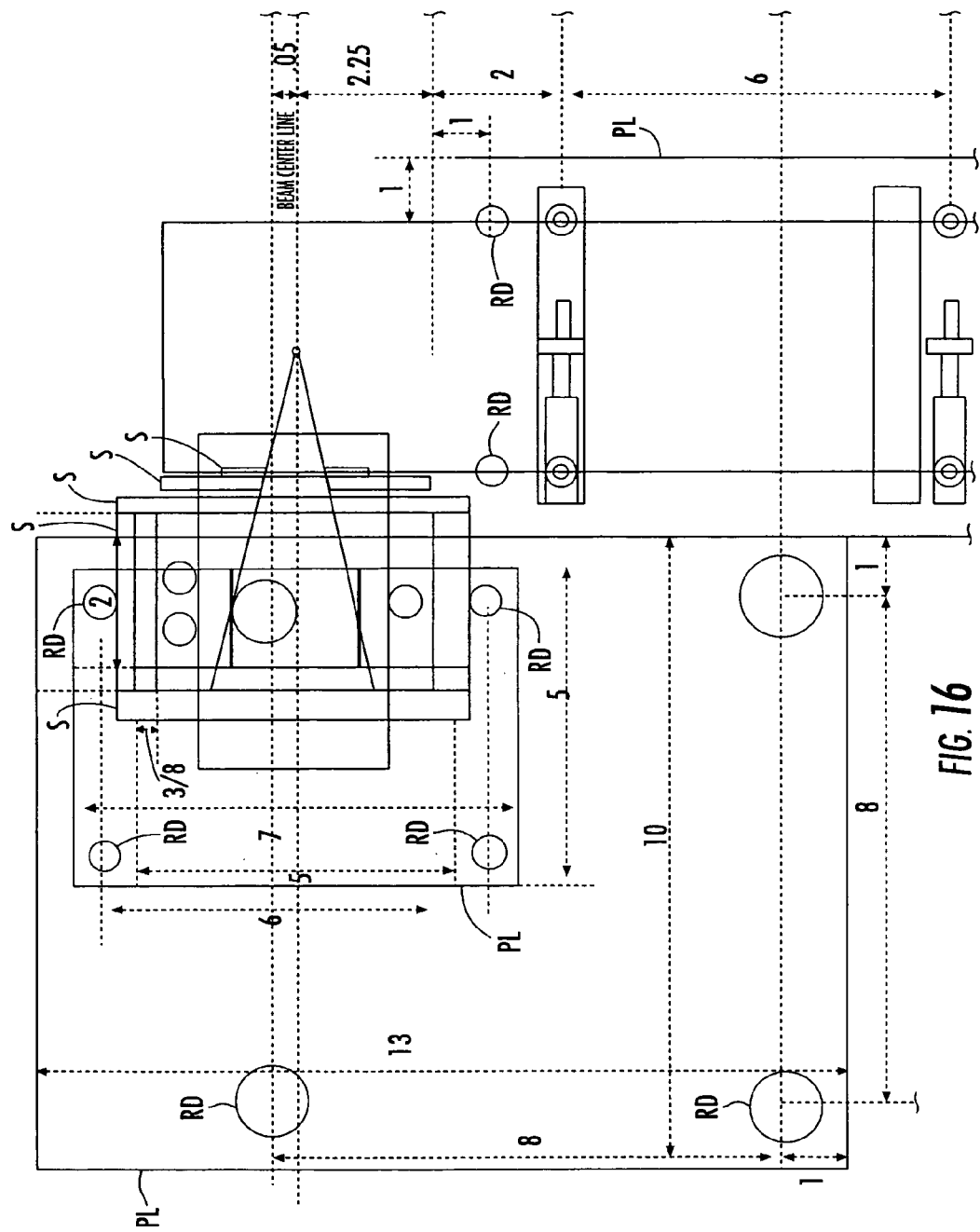

FIGS. 15 and 16 are schematic diagrams of another side view and another top view, respectively, of the exemplary arrangement shown in FIGS. 13 and 14. Referring to FIGS. 15 and 16, the arrangement is shown without side plates and top plates, respectively, in order to illustrate shielding S. Shielding S can function to prevent the emission of X-ray beam XB in undesired directions. Additional shielding can be utilized for protection. Further, suitable shielding can be provided in a clinical device as needed.

FIGS. 17-26 are images of exemplary portions of a DEI system according to an embodiments of the subject matter described herein. In particular, referring to FIG. 17, an image is shown of an X-ray beam exit portion of X-ray tube XT. X-ray beams can be emitted from X-ray tube XT and through a Be window BW, which is attached to X-ray tube XT and positioned for intercepting X-ray beams. Be window BW is fitted with two layers of internal lead (Pb) shielding PS.

Figure 18:
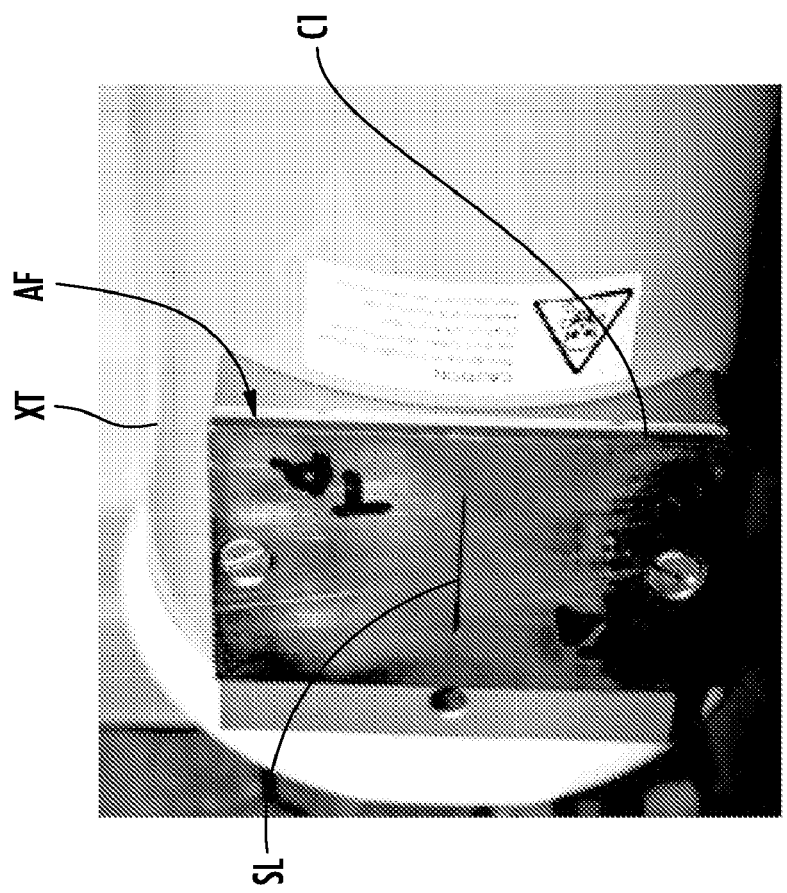
FIG. 18 is another image of the X-ray beam exit portion of the X-ray tube shown in FIG. 17.
Figure 17:
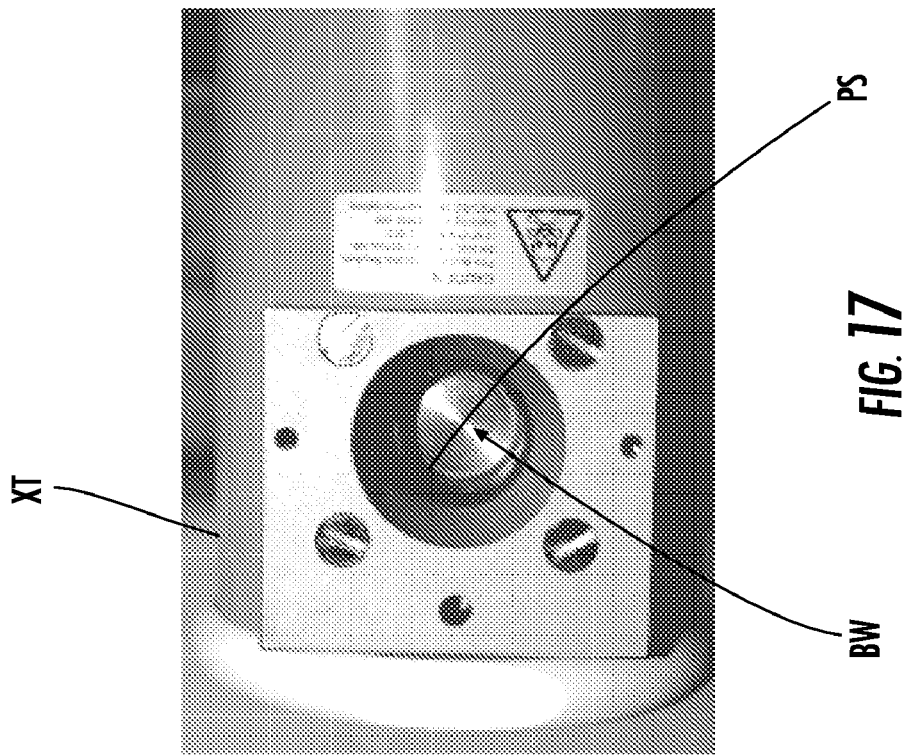
FIG. 17 is an image of an X-ray beam exit portion of an X-ray tube according to an embodiment of the subject matter described herein.

FIG. 18 is another image of the X-ray beam exit portion of X-ray tube XT shown in FIG. 17. In this image, Al filter AF and collimator C1 are attached to X-ray tube XT and positioned for intercepting X-ray beams. Al filter AF is about 2 mm in thickness. Collimator C1 includes a slit SL for passable of X-ray beams. In this example, collimator C1 is made of tantalum (Ta) and about 1/8 inches in thickness. In one example, the slit is sized to be slightly larger than the spot size on the X-ray tube. In one example, the slit is 1.0 mm and the spot size on the X-ray tube is 0.4 mm. The slit can provide for a vertically collimated fan beam.

Figure 19:
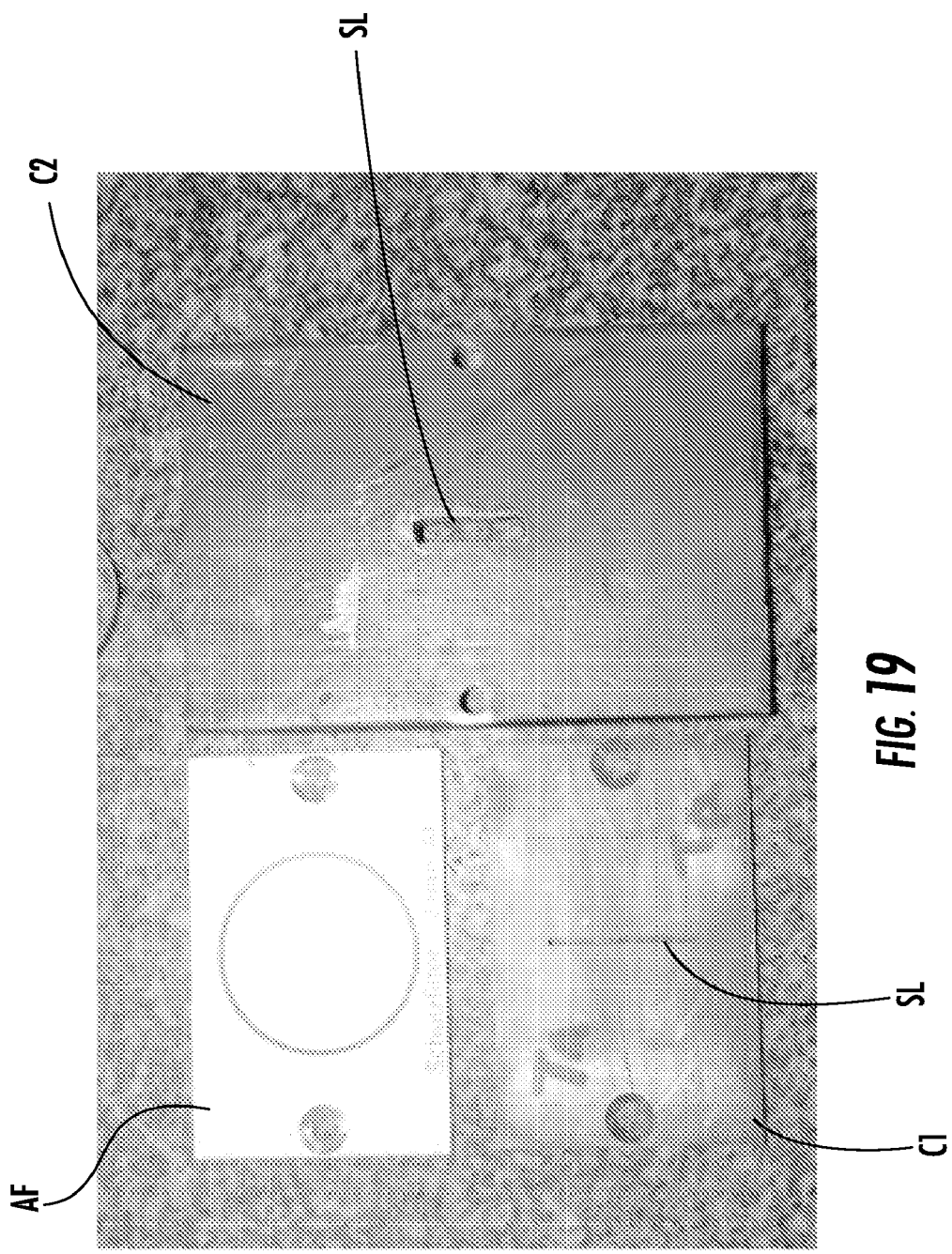
FIG. 19 is an image of an aluminum filter and collimators according to an embodiment of the subject matter described herein.

FIG. 19 is an image of Al filter AF, collimator C1, and another collimator C2. In this image, the components are disassembled for the purpose of illustration. The components can be fitted together adjacent one another in an assembled state.

Figure 21:
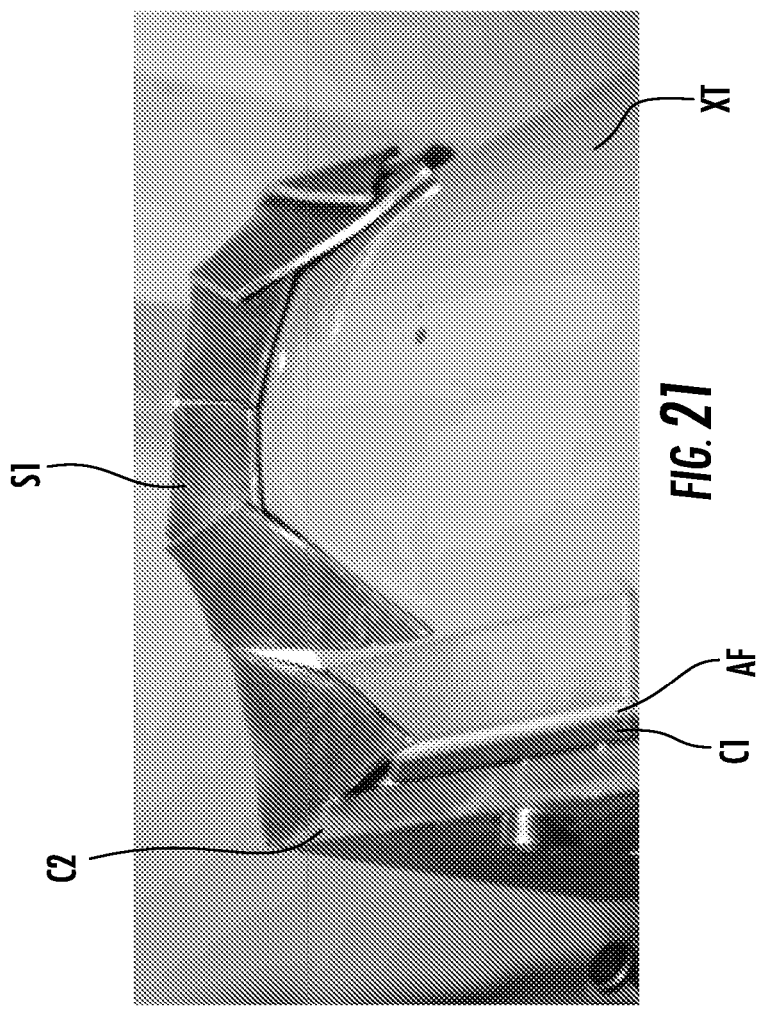
FIG. 21 is an image of a shielding cap on an end of an X-ray tube for the purpose of preventing the undesired emission of X-ray beams from the end of X-ray tube according to an embodiment of the subject matter described herein.
Figure 20:
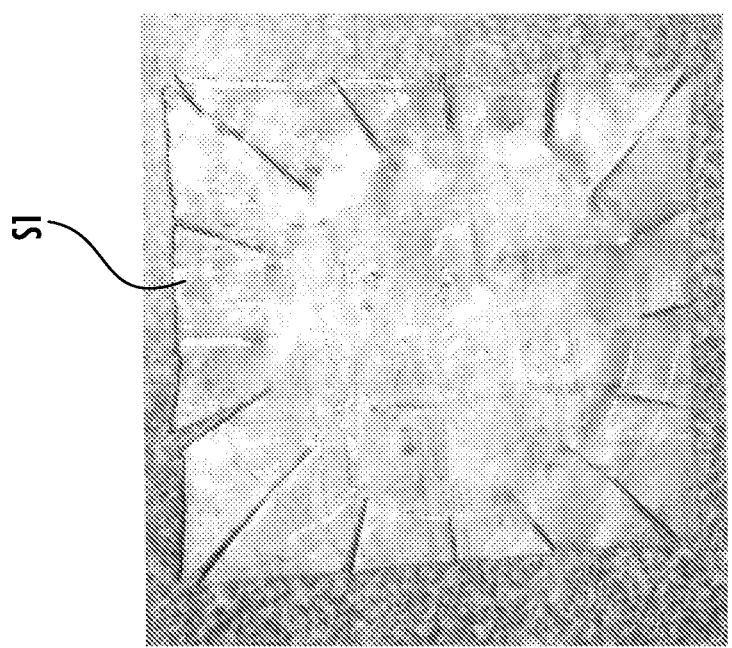
FIG. 20 is an image of the shielding cap that is disassembled and cut but not bent for fitting to the end of X-ray tube according to an embodiment of the subject matter described herein.

FIGS. 20 and 21 are images of a shielding cap and an X-ray tube. FIG. 20 is an image of a shielding cap S1 that is disassembled and cut but not bent for fitting to the end of X-ray tube XT. FIG. 21 is an image of shielding cap S1 on an end of X-ray tube XT for the purpose of preventing the undesired emission of X-ray beams from the end of X-ray tube XT. Shielding cap S1 is a 1/8 inch lead sheet that is cut and bent in the shape of a cap for fitting to the end of X-ray tube XT.

Figure 22:
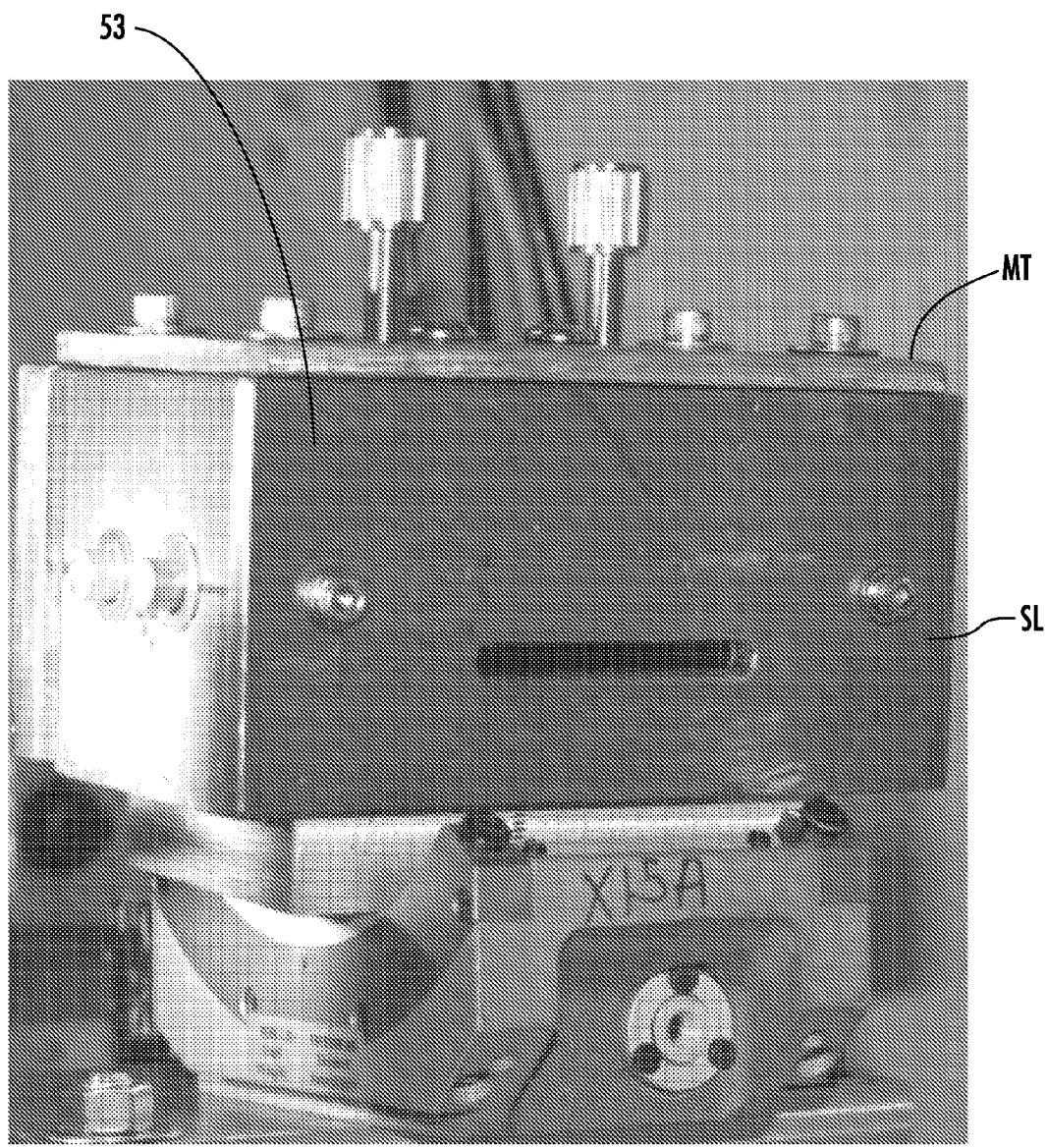
FIG. 22 is an image of the monochromator tank including lead shielding for preventing the undesired emission of X-ray beams from monochromator tank according to an embodiment of the subject matter described herein.

FIG. 22 is an image of monochromator tank MT including lead shielding S3 for preventing the undesired emission of X-ray beams from monochromator tank MT. Shielding S3 is about a ½ inch thick lead sheet and includes slit SL for the emission of a desired portion of X-ray beams. The X-ray beams emitted from X-ray tube exit monochromator tank MT via slit SL of shielding S3.

Figure 23:
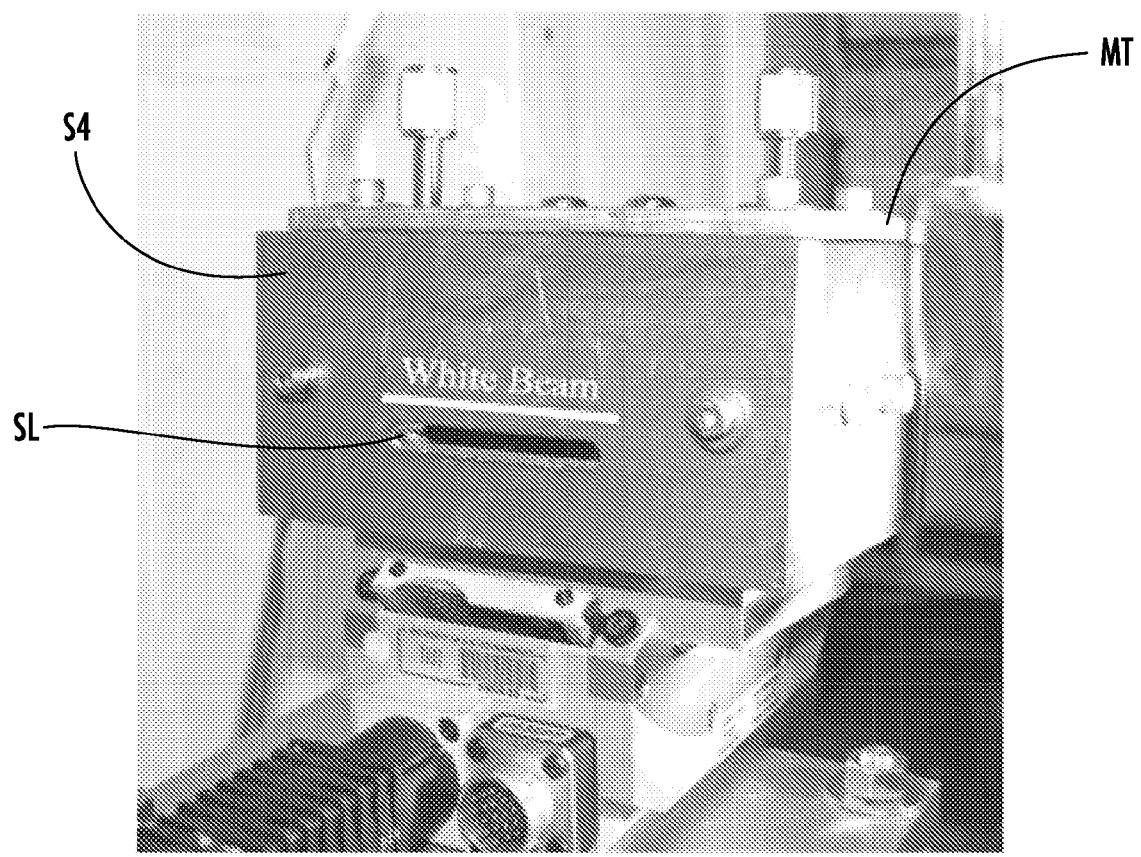
FIG. 23 is an image of a monochromator tank including lead shielding for preventing the undesired emission of X-ray beams from monochromator tank according to an embodiment of the subject matter described herein.

FIG. 23 is an image of monochromator tank MT including lead shielding S3 for preventing the undesired emission of X-ray beams from monochromator tank MT. Shielding S3 is about ¼ inch thick lead sheet and includes a slit SL for the emission of a desired portion of X-ray beams. The X-ray beams emitted from X-ray tube enter monochromator tank MT via slit SL of shielding S3.

Figure 24:
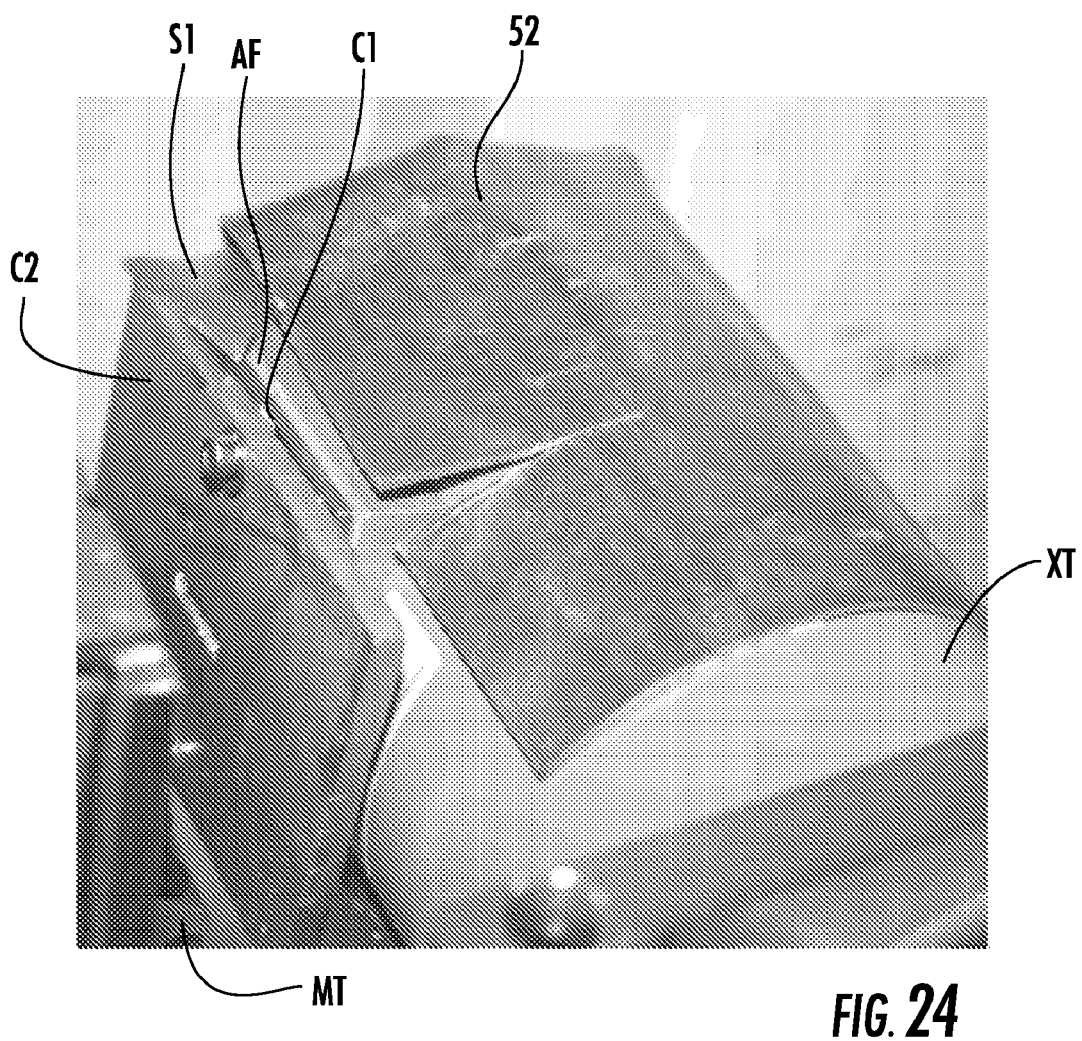
FIG. 24 is an image of another portion of shielding positioned near the end of the X-ray tube for preventing the undesired emission of X-ray beams from a side of X-ray tube according to an embodiment of the subject matter described herein.

FIG. 24 is an image of another portion of shielding S2 positioned near the end of X-ray tube XT for preventing the undesired emission of X-ray beams from a side of X-ray tube XT. Shielding S2 is a 1/16 inch lead sheet that is cut and bent into a shape for fitting to the side of X-ray tube XT. A ⅛ inch of lead sheet can reduce 150 keV X-rays by a factor of 1000.

Figure 25:
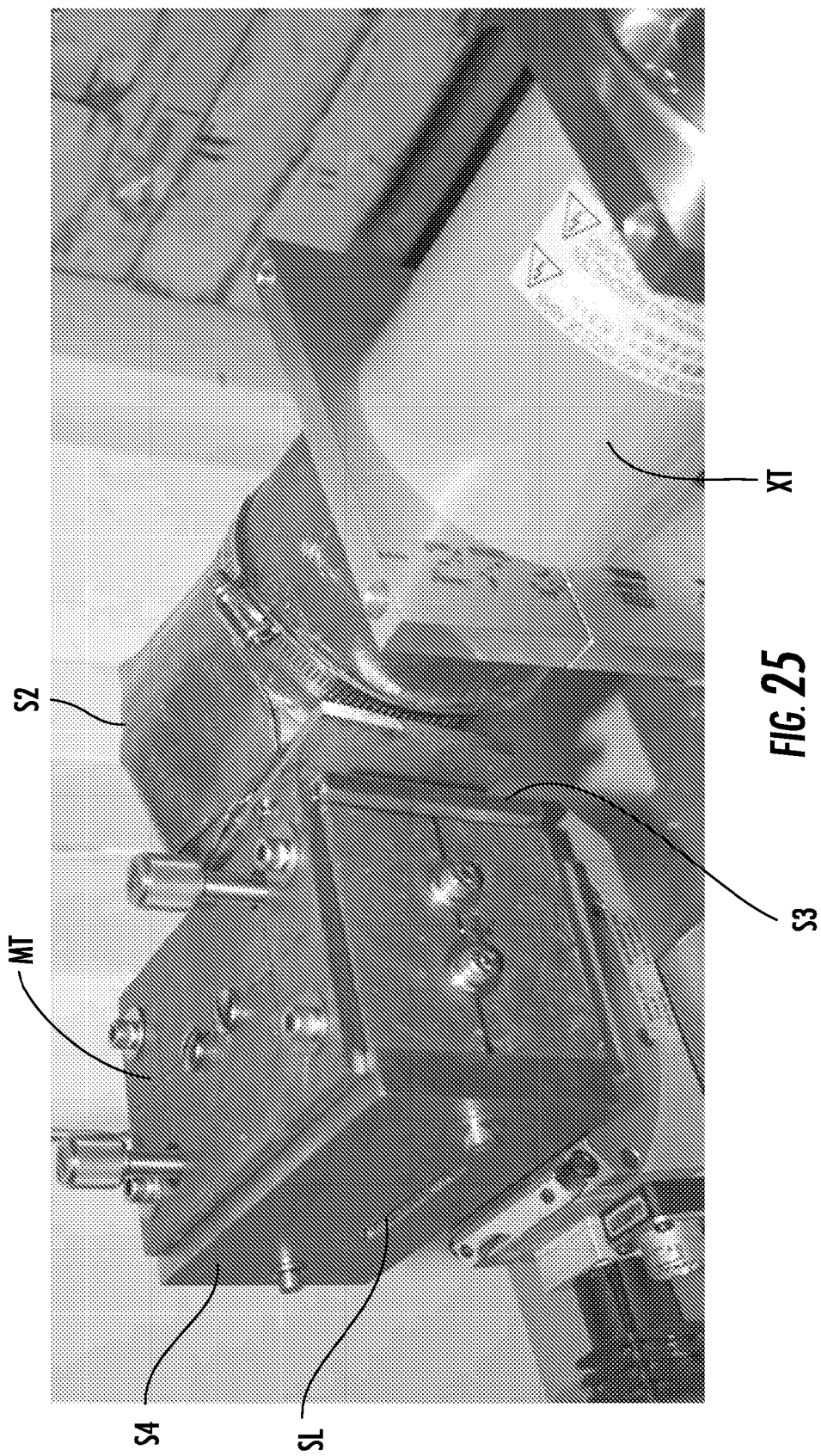
FIG. 25 is an image of an X-ray tube and a monochromator tank in an operational position with respect to one another according to an embodiment of the subject matter described herein.

FIG. 25 is an image of X-ray tube XT and monochromator tank MT in an operational position with respect to one another.

Figure 26:
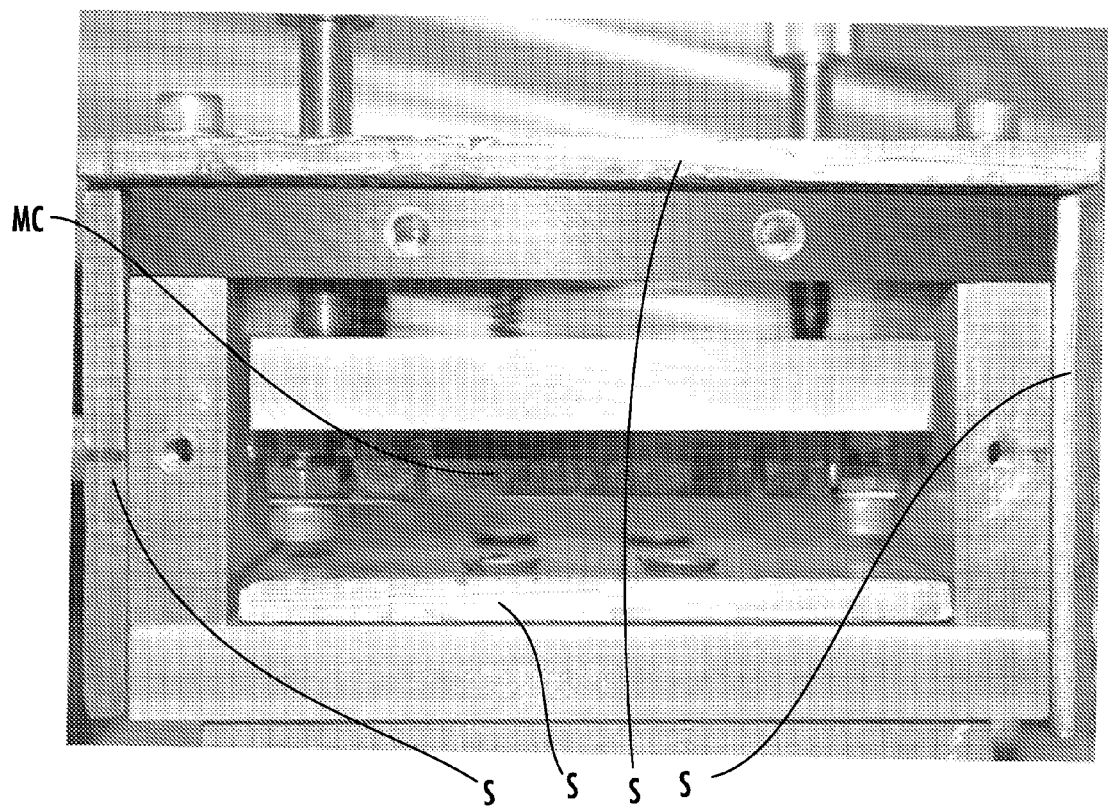
FIG. 26 is an image of a front view of internal components of monochromator tank according to an embodiment of the subject matter described herein.

FIG. 26 is an image of a front view of internal components of monochromator tank MT. In particular, monochromator crystal MC is shown. Further, shielding S is positioned on the sides of monochromator tank MT.

Figure 27:
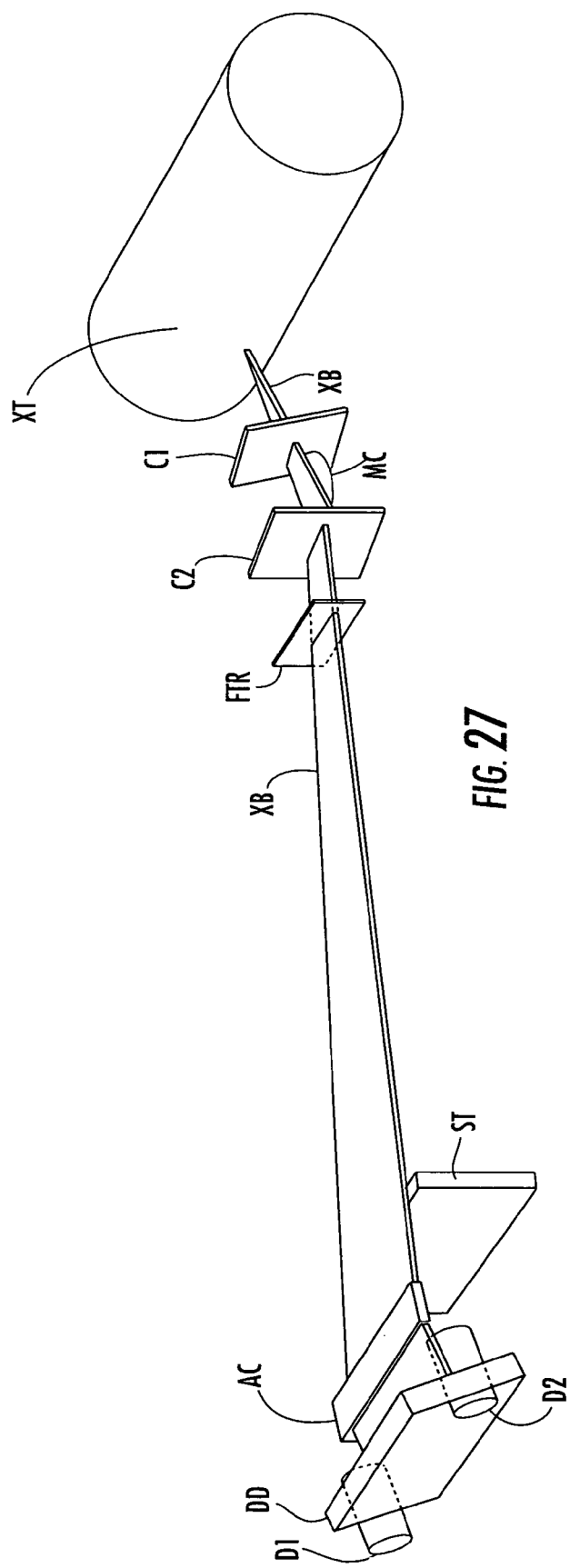
FIG. 27 is a top perspective view of an exemplary DEI system according to an embodiment of the subject matter described herein.

FIG. 27 is a top perspective view of an exemplary DEI system, generally designated 2700, according to an embodiment of the subject matter described herein. Referring to FIG. 27, DEI system 2700 can include X-ray tube XT having a tungsten anode for producing a plurality of X-ray beam XB. Collimator C1 can be positioned for blocking a portion of X-ray beam XB that fall outside an angular acceptance window of monochromator crystal MC. In this example, monochromator crystal MC is a silicon crystal. Collimator C2 can be positioned for blocking a portion of X-ray beam XB that falls outside an angular acceptance window of analyzer crystal AC.

The portion of X-ray beam XB passing through collimator C2 can be intercepted by a copper filter FTR configured to thermally isolate heat and equally as important attenuate 20 keV bremsstrahlung X-rays produced by the X-ray tube XT. For a given Bragg angle, there can be unwanted crystal reflections that are able to traverse the monochromator. One example using a Bragg angle of about 5.7 degrees to select a 59.13 keV [333] reflection is also the angle that allows 19.71 keV [111] X-rays to pass. If these X-rays are diffracted across monochromator crystal MC, they will induce blurring, image artifacts, and thus reduce overall image quality. A copper filter FTR is used to attenuate lower energy X-rays, specifically 19.71 keV bremsstrahlung, X-ray photons, emitted from the X-ray beam XB and diffracted across the monochromator MC.

Analyzer crystal AC can be positioned for intercepting at least a portion of X-ray beam XB passing through filter FTR. Further, an object can be positioned in the path of X-ray beam XB by a scanning stage ST for imaging of the object. During scanning of object O, X-ray beam XB can pass through object O and can be analyzed by analyzer crystal AC, which can be a silicon [333] crystal that matches monochromator crystal MC. X-ray beam XB incident on analyzer crystal AC can diffract for interception by digital detector DD. Digital detector DD can detect the intercepted X-ray beam XB and generate electrical signals representative of the intercepted X-ray beams. The electrical signals can be communicated to a computer for image analysis and display to an operator. The computer can be configured to generate an absorption image and an image showing refraction effects, the types of which are described in more detail below.

Figure 28:
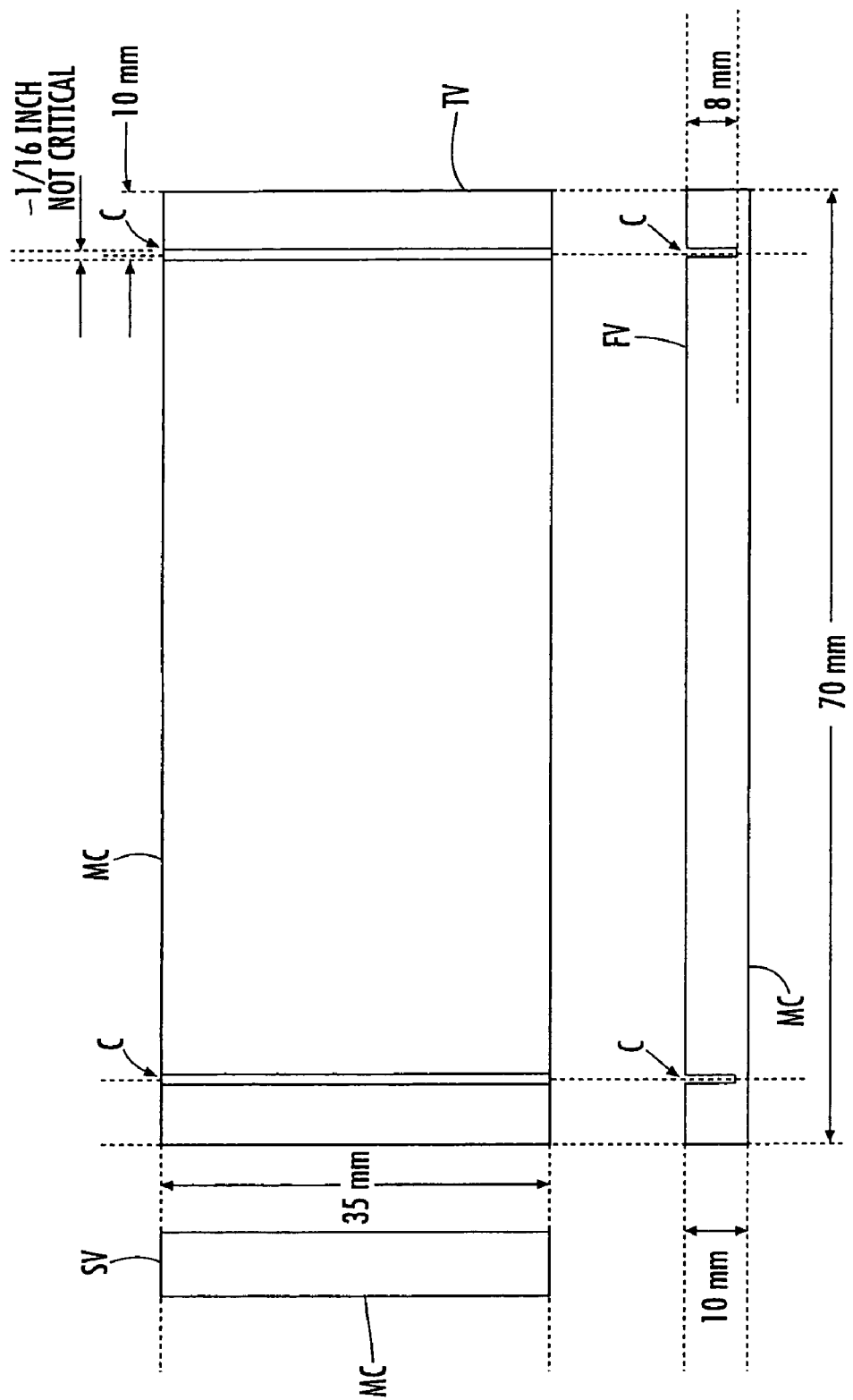
FIG. 28 is a schematic diagram including a side view, a top view, and a front view of an exemplary monochromator crystal according to an embodiment of the subject matter described herein.

FIG. 28 is a schematic diagram including a side view, a top view, and a front view of an exemplary monochromator crystal MC according to an embodiment of the subject matter described herein. Referring to FIG. 28, the side view, the top view, and the front view of monochromator crystal MC are designated SV, TV, and FV, respectively. The dimensions of monochromator crystal MC are shown in the figure and can be about ±0.5 mm. Alternatively, the monochromator crystal may have other suitable dimensions, which is in part determined by the imaging application. The surface orientation of monochromator crystal MC can be that of the lattice planes parallel to the large surfaces of the crystal. When fabricated, the orientation of the other smaller orthogonal surfaces may be noted for reference. Exemplary monochromator crystals can be a germanium [111] monochromator crystal and silicon [111] monochromator crystal of type A.

Monochromator crystal MC may include strain relief cuts, generally designated C, defined within a top portion of the crystal. The width of the cuts C are about 1/16 inch in thickness. Alternatively, the width can be any other suitable dimension. Cuts C remove the parts of the crystal used for attachment and allow the remaining portion of the analyzer crystal AC and monochromator crystal MC to be strain free. If any stress or strain is induced in the imaging portion of the analyzer crystal AC or monochromator crystal MC, it will alter the diffraction properties and adversely impact system performance.

Imaging Procedures and Quality Control for using DEI and DEI Systems

Image acquisition using a DEI system configured with a mismatch crystal design in accordance with the subject matter described herein can begin with the selection of an appropriate beam energy for a given experiment. In one example, the beam energy can be selected from a range between about 10 keV and about 60 keV. Selection of a particular energy for imaging can be accomplished by using Bragg's law to calculate the appropriate angle for the desired wavelength. In one example, the first crystal in the monochromator can have only one axis of movement which can be tuned to a particular angle to remove all energies from the incident X-ray beam except for the selected beam energy. Table 1 below shows exemplary angles of the first monochromator crystal for acquiring images between 18 keV and 60 keV. These angles for silicon, calculated using Bragg's law, $\lambda = 2d \sin(\theta)$, define the incident angle theta ($\theta$) and diffracted angle theta ($\theta$) of the X-ray beam as it diffracts across monochromator crystal MC. The detector is placed at an angle $2\theta$, twice that of the Bragg angle used in the first crystal for selecting the X-ray beam energy.

TABLE 1

Exemplary Angles for the Silicon [333] Reflection of the First Monochromator Crystal for Acquiring Images

| Energy (keV) | θ (degrees) | 2θ (degrees) |
|---|---|---|
| 18 | 19.23 | 38.46 |
| 19 | 18.19 | 36.38 |
| 20 | 17.25 | 34.50 |
| 21 | 16.41 | 32.82 |
| 22 | 15.64 | 31.28 |
| 23 | 14.94 | 29.88 |
| 24 | 14.30 | 28.60 |
| 25 | 13.72 | 27.44 |
| 26 | 13.18 | 26.36 |

TABLE 1-continued

Exemplary Angles for the Silicon [333] Reflection of the First
Monochromator Crystal for Acquiring Images

| Energy (keV) | θ (degrees) | 2θ (degrees) |
|---|---|---|
| 27 | 12.69 | 25.38 |
| 28 | 12.23 | 24.46 |
| 29 | 11.80 | 23.60 |
| 30 | 11.40 | 22.80 |
| 31 | 11.03 | 22.06 |
| 32 | 10.68 | 21.36 |
| 33 | 10.35 | 20.70 |
| 34 | 10.05 | 20.10 |
| 35 | 9.76 | 19.52 |
| 36 | 9.48 | 18.96 |
| 37 | 9.22 | 18.44 |
| 38 | 8.98 | 17.96 |
| 39 | 8.75 | 17.50 |
| 40 | 8.53 | 17.06 |
| 41 | 8.32 | 16.64 |
| 42 | 8.12 | 16.24 |
| 43 | 7.93 | 15.86 |
| 44 | 7.75 | 15.50 |
| 45 | 7.57 | 15.14 |
| 46 | 7.41 | 14.82 |
| 47 | 7.25 | 14.50 |
| 48 | 7.10 | 14.20 |
| 49 | 6.95 | 13.90 |
| 50 | 6.81 | 13.62 |
| 51 | 6.68 | 13.36 |
| 52 | 6.55 | 13.10 |
| 53 | 6.43 | 12.86 |
| 54 | 6.31 | 12.62 |
| 55 | 6.19 | 12.38 |
| 56 | 6.08 | 12.16 |
| 57 | 5.97 | 11.94 |
| 58 | 5.87 | 11.74 |
| 59 | 5.77 | 11.54 |
| 60 | 5.67 | 11.34 |

A DEI system configured with a mismatch crystal design include three crystals that should be tuned and carefully aligned, two crystals in the monochromator and the analyzer crystal. For example, DEI system 600 includes monochromator crystals MC1 and MC2 and analyzer crystal AC that can be tuned and aligned. The first crystal (e.g., monochromator crystal MC1 shown in FIGS. 6A and 6B) and the analyzer crystal (e.g., analyzer crystal AC shown in FIGS. 6A and 6B) can be tuned to an angle (theta angle) calculated for each energy. For example, to tune the system to 25 keV, the first monochromator crystal is set to 13.17 degrees and the analyzer crystal is set to 13.72 degrees. The digital detector assembly can be set at an angle twice that of the analyzer crystal, which is 27.44 degrees in this example.

Figure 29:
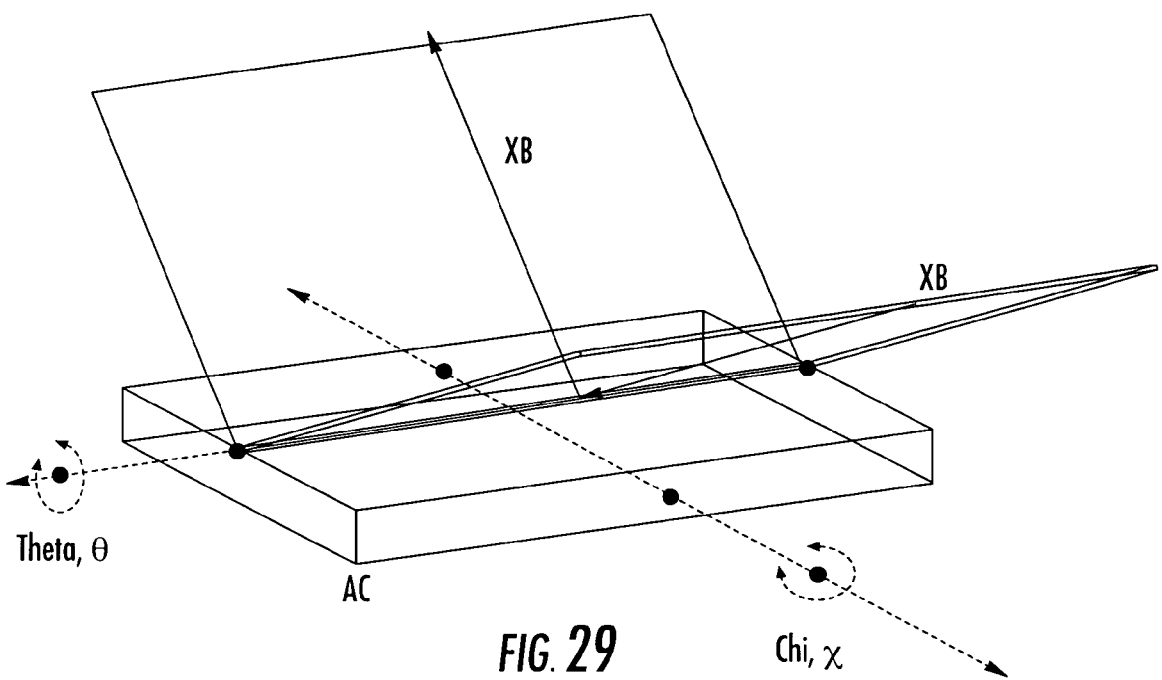
FIG. 29 is a perspective view of a monochromator crystal showing the inboard/outboard regions and chi and theta angles of rotation according to an embodiment of the subject matter described herein.

The second monochromator crystal (e.g., monochromator crystal MC2 shown in FIGS. 6A and 6B) can be adjusted in the horizontal direction, referred to as a chi angle. If the horizontal alignment is off between these crystals, there may be an intensity shift from left to right in the image. Two ion chambers can be used to measure the flux emitted from both the monochromator and the analyzer, which are both divided into an inboard and outboard region. If viewing the X-ray beam from the source to the detector assembly, the inboard region is on the right and the outboard region is on the left. The inboard and outboard regions can be sampled to make sure that the rocking curve peaks are aligned; if not, the chi angle can be adjusted. FIG. 29 is a perspective view of a monochromator crystal showing the inboard/outboard regions and chi and theta angles of rotation.

The dose applied by the DEI system can be adjusted in a number of ways. For example, the dose can be adjusted by changing an aluminum filter thickness and/or placing absorbers in the path of the X-ray beam. The dose can also be reduced by detuning the second monochromator crystal away from the peak of the rocking curve, dramatically reducing the diffracted intensity if needed. In one example, the X-ray tube can be replaced by a synchrotron, in which case the incident flux on the first monochromator crystal is determined by the ring current of the synchrotron.

Sample acquisition time can be determined by the incident flux, with the translation rate of the sample stage measured in steps/second. The scan speed can be increased or decreased by adjusting the dose, measured in steps/second. Scan speed may not be a critical factor when using image plates where the amount of noise is fixed, but it must be considered when using integrating digital detectors since the amount of noise is in part determined by acquisition time. When using a digital detector, the DEI system should be tuned so that the scan speed is as close to maximum as possible.

Once the DEI or DEI system is tuned for the proper energy and dose, the object to be imaged can be placed on the sample stage and aligned. In one example, the maximum width of the X-ray beam is 120 mm, which physically limits the width of the resulting image. Use of a digital detector or image plate with a width less than 120 mm can further limit the field of view. In one example, the sample stage has a maximum vertical displacement of about 200 mm. However, there are no physical limits to sample height. For imaging a particular region of an object, one must determine whether this region lies within the 200 mm range for the system. The position of the X-ray beam may be fixed, so the object vertical region of interest can be determined by its relative position to the beam.

The crystals used in a DEI system are considered to be homogenous in their ability to diffract photons over a given area of the crystal, but the structure of the crystal is such that there are minor regions of increased or decreased intensity. Since the object to be scanned through a beam of fixed dimension, these "glitches" can be smeared across the vertical dimension of the image. The term "glitch" is often applied to these vertical lines, but these affects are expected and should be considered a known and expected property of the system.

Experimentation with Respect to System
Performance Characteristics

Prior to constructing DEI and DEI systems including X-ray tubes as described herein, experiments were conducted using a synchrotron as an X-ray source for testing purposes. As an initial demonstration, imaging times and flux requirements using 18 keV and 59 keV X-rays were calculated, simulating molybdenum and tungsten based X-ray sources. Further, several assumptions were made in regards to the system configuration, such as the pixel size and the number of photons per pixel. Since these values can be scaled as needed, a pixel size of 100 microns with 1000 photons per pixel traversing 5 cm of tissue (water) will be used in this example.

The number of photons needed per 100 micron square pixel can be calculated by dividing the number of photons per pixel desired by the attenuation of the photons through the object, which in this case is 5 cm of water.

$$N_{18keV}^{Surface} = \frac{1000\,\text{photons/pixel}}{e^{-\mu_{tot}t}} = \frac{1000\,\text{photons/pixel}}{6.4\times10^{-3}} = 1.6\times10^5\,\text{photons}/100\,\mu m sq pixel$$

$$N_{59keV}^{Surface} = \frac{1000\,\text{photons/pixel}}{e^{-\mu_{tot}t}} = \frac{1000\,\text{photons/pixel}}{0.35} = 2.9\times10^3\,\text{photons}/100\,\mu m sq pixel$$

Thus, for an 18 keV X-ray source, approximately $1.6\times10^5$ incident photons would be required for each 100 micron square pixel. The attenuation of 59 keV X-rays is much less than at 18 keV, which results in a reduced incident photon demand of $2.9\times10^3$ photons per 100 micron square pixel.

Incident X-Ray Flux into Solid Angle Using an Emission Line Source

The crystal optics used in DEI and DEI systems act as a highly selective angular notch filter, which will eliminate photons from the X-ray beam that do not have the proper energy or angular divergence. For an X-ray tube-based source, photons are expected to radiate more-or-less into all solid angles. In order to determine the flux requirement, one must calculate the flux based on the solid angle subtended by the detector and the X-ray crystal optics. Any X-ray tube is going to have a polychromatic energy distribution, and the crystal system will select one of the emission lines as defined by Bragg's law.

With a perfect crystal, the peak reflectivity for a given reflection is expected to be very close to unity, making the integrated reflectivity close to the intrinsic reflection width in the Bragg-normal direction, or Darwin width. Assuming a silicon crystal with a Bragg [333] reflection, the Darwin width of 18 keV and 59 keV are as follows:

18 keV Si [333] DarwinWidth=$2.9\times10^{-6}$ radians, and 59.3 keV Si [333] DarwinWidth=$0.83\times10^{6}$ radians.

X-rays traveling in a direction parallel to the crystal lattice planes are known as Bragg-parallel, and the angular acceptance in the Bragg-parallel direction is not set by the crystal, but rather the detector resolution. If the object to be imaged is 1 meter from the X-ray source and a 100 micron spatial resolution is required, then the Bragg-parallel acceptance angle is 100 microradians. For a 100 microradian Bragg-parallel acceptance angle, the number of photons required per steradian at 18 keV and 59 keV are as follows:

$$N_{18keV}^{Required} = \frac{1.6\times10^5\,\text{photons/pixel}}{2.9\times10^{-6}\,\text{radians}\times100\times10^{-6}\,\text{radians/pixel}} = 0.55\times10^{15}\,\text{photons/steradian}$$

$$N_{59keV}^{Required} = \frac{2.9\times10^3\,\text{photons/pixel}}{0.83\times10^{-6}\,\text{radians}\times100\times10^{-6}\,\text{radians/pixel}} = 3.5\times10^{13}\,\text{photons/steradian}.$$

X-Ray Tube Flux

X-ray tube based sources can have two components to their X-ray spectrum, characteristic emission lines and bremsstrahlung. The crystal optics of DEI and DEI system allow for the selection of only one extremely narrow band of energies, which should be centered at the characteristic emission line of the tube target. In this case, the K$\alpha$1 of molybdenum (17.478 keV) and the K$\alpha$1 of tungsten (59.319 keV) can be used to determine the flux of these emission lines from each source.

Monte Carlo simulations of molybdenum and tungsten X-ray tubes at multiple voltage and current setting were generated to determine the flux that could be generated under realistic imaging conditions. For a molybdenum target using a 75 kV accelerating voltage with 10 kW of power, the flux emitted into the K$\alpha$1 is as follows:

$$n_{MoK\alpha1}^{Source} = 1.7\times10^{14}\,\text{photons/steradian/sec}.$$

The K$\alpha$1 emission using tungsten target with a 150 kV accelerating voltage and 50 kW of power is as follows:

$$n_{WK\alpha1}^{Source} = 1.56\times10^{14}\,\text{photons/steradian/sec}.$$

Estimated Image Acquisition Time

If the analyzer is detuned to a value (80%) from the peak position, one can acquire one exposure containing refraction contrast and some extinction contrast. These calculations assume a DEI system having a single monochromator crystal and analyzer crystal. The geometry of this simulation is consistent with that used at the National Synchrotron Light Source (NSLS) X15A beamline (located at Brookhaven National Laboratory, Upton, N.Y.), using a line source X-ray in which the object is scanned through the beam. For an object 10 cm in height and a 100 micron pixel size (0.1 mm), 1000 scan lines will be required.

$$T(\text{sec}) = \frac{N_{Energy}^{Required}\,(\text{photons/steradian})}{n_{Energy}^{source}\,(\text{photons/steradian})} \Big/$$

$$0.8(\text{det unelosses})\times1(DEI\text{images})\times1000(\text{scanlines})$$

For the 75 kV, 10 kW, molybdenum target case (approximately 18 keV):

$$T = \frac{0.55\times10^{15}\,\text{photons/steradian}}{1.7\times10^{14}\,\text{photons/steradian/sec}}\times1250 = 0.4\times10^4\,\text{sec} = 1.1\,hr$$

For the 150 kV, 50 kW, tungsten target case (approximately 59.3 keV):

$$T = \frac{3.5 \times 10^{13} \text{photons/steradian}}{1.56 \times 10^{14} \text{photons/steradian/sec}} \times 1250 = 0.28 \times 10^3 \text{sec} = 4.6 \text{ min}$$

For a single image at a point on the rocking curve with 80% of maximum reflectivity, the time required using a molybdenum target using the above parameters is about 1.1 hours. The time required using the same reflectivity for a tungsten tube is approximately 4.6 minutes. The imaging time may be further decreased by imaging variables such as the photons needed per pixel and changing the distance from the object to the source.

Figure 30:
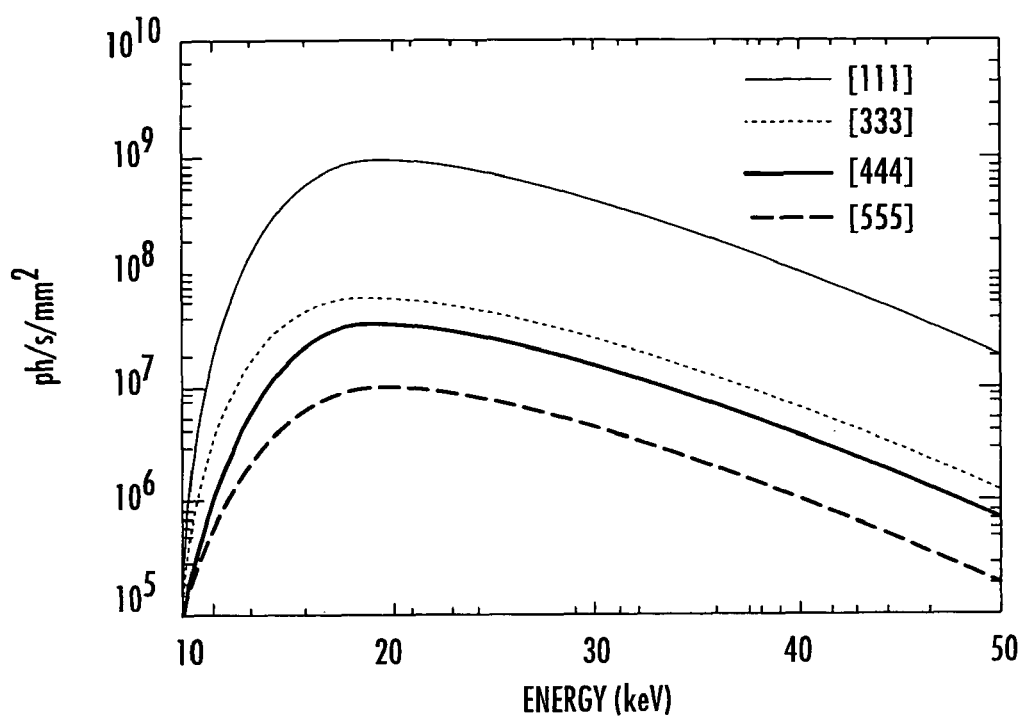
FIG. 30 is a graph of the monochromatic beam flux in a National Synchrotron Light Source X15A hutch using silicon [111], [333], [444], and [555] crystal diffraction planes.

Based on the data calculated using a Bragg [333] reflection with a source to object distance of 1000 mm, estimate imaging times can be estimated using other reflections and distances. There are two crystal reflections that may be used for DEI, the Bragg [333] and Bragg [111] reflections. Both refraction and extinction contrast in DEI are in large part determined by the slope of the analyzer reflectivity curve, with a steeper slope providing more contrast for a given change in angle. The Bragg [333] reflection may be superior to the Bragg [111] reflection in terms of refraction and extinction contrast, but the diffracted flux from the [333] reflection is approximately an order of magnitude less than the [111] reflection. FIG. 30 is a graph illustrating the monochromatic beam flux in the NSLS X15A hutch using silicon [111], [333], [444], and [555] crystal diffraction planes. A ten-fold increase in flux can reduce the imaging time by a factor of 10, making the [111] reflection advantageous for certain applications. Further reductions in imaging time can be achieved by reducing the distance from the source to object, which is calculated as described herein using a distance of 1000 mm. Photon intensity from the source to the object being imaged is proportional to $1/r^2$. If the object distance is decreased from 1000 mm to 500 mm, the intensity can be increased four-fold. There are many factors that can dictate the source-object distance, one of the most significant being object size. The analyzer/detector assembly can be moved closer or farther away from the source as required depending on the application.

The full width at half maximum (FWHM) of the analyzer rocking curve narrows as the energy is increased (e.g., 3.86 microradians at 18 keV and 1.25 microradians at 60 keV). An example of rocking curve widths versus energy is shown in Table 2 below. In particular, Table 2 below shows the measured and theoretical FWHM of the [333] analyzer rocking curves at 18, 30, and 60 keV. The [333] double-Bragg monochromator was tuned to the Bragg peak.

TABLE 2

Measured and Theoretical FWHM of the [333] analyzer rocking curves at 18, 30, and 60 keV

| X-ray Energy (keV) | Measured FWHM (μrad) | Theoretical FWHM (μrad) |
|---|---|---|
| 18 | 3.86 | 3.64 |
| 30 | 2.15 | 2.10 |
| 60 | 1.25 | 1.11 |

Figure 31:
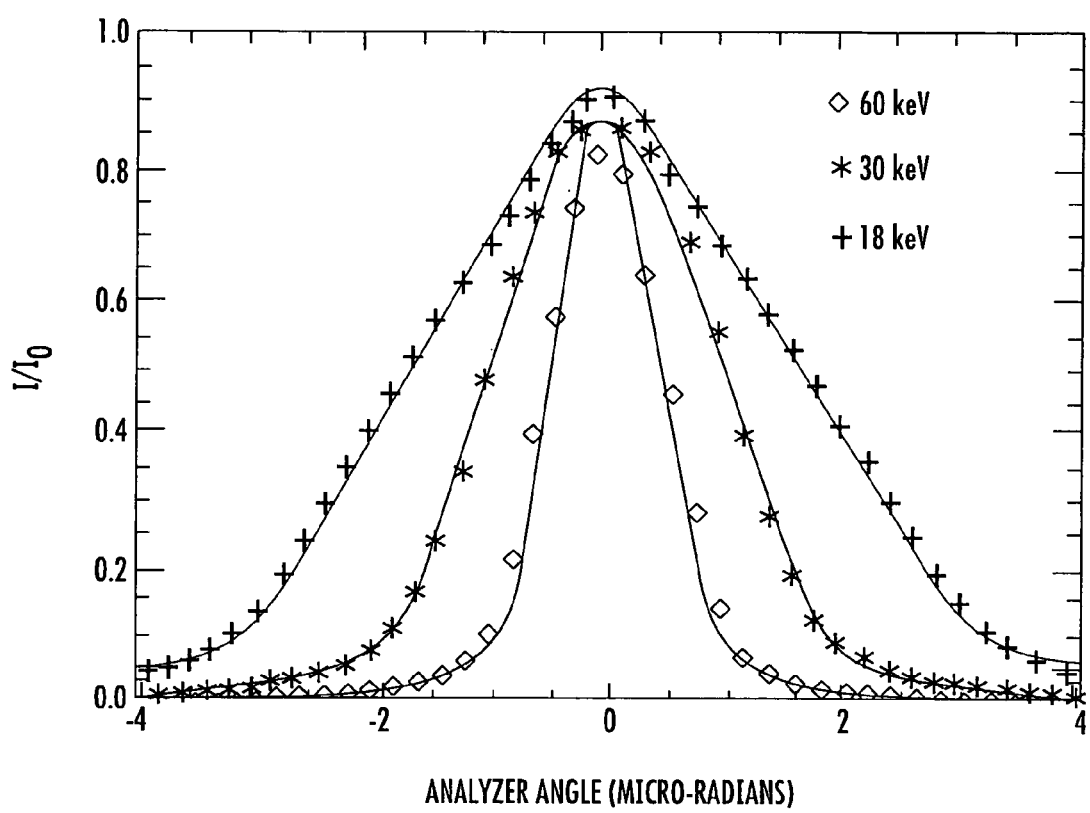
FIG. 31 is a graph illustrating that the reduction in the FWHM increases the slope of the rocking curve.

The reduction in the FWHM increases the slope of the rocking curve, further increasing refraction and extinction contrast. FIG. 31 is a graph illustrating that the reduction in the FWHM increases the slope of the rocking curve. Using the flux calculations for a 50 kW, Bragg [333] reflection, and source to object distance of 1000 mm, one can estimate the imaging times required for various distances and crystal reflections, as shown in Table 3 below. In particular, Table 3 shows the estimated imaging times based on crystal reflection and source-object distance.

TABLE 3

Estimated Imaging Times Based on Crystal Reflection and Source-Object Distance

| Crystal Reflection | Source to Object (mm) | Estimated Imaging Time (seconds) |
|---|---|---|
| Bragg [333] | 1000 | 280 |
| Bragg [333] | 500 | 70 |
| Bragg [111] | 1000 | 28 |
| Bragg [111] | 500 | 7 |

Synchrotron-Based DEI and DEI System Experimentation

As stated above DEI and DEI system experimentations were conducted using a synchrotron. In particular, the NSLS X-15A beamline was utilized for DEI and DEI experimentations as described herein. The synchrotron X-ray source used for experimentations as described herein can be substituted with an X-ray tube in accordance with the subject matter described herein for producing DEI or DEI images.

Figure 32:
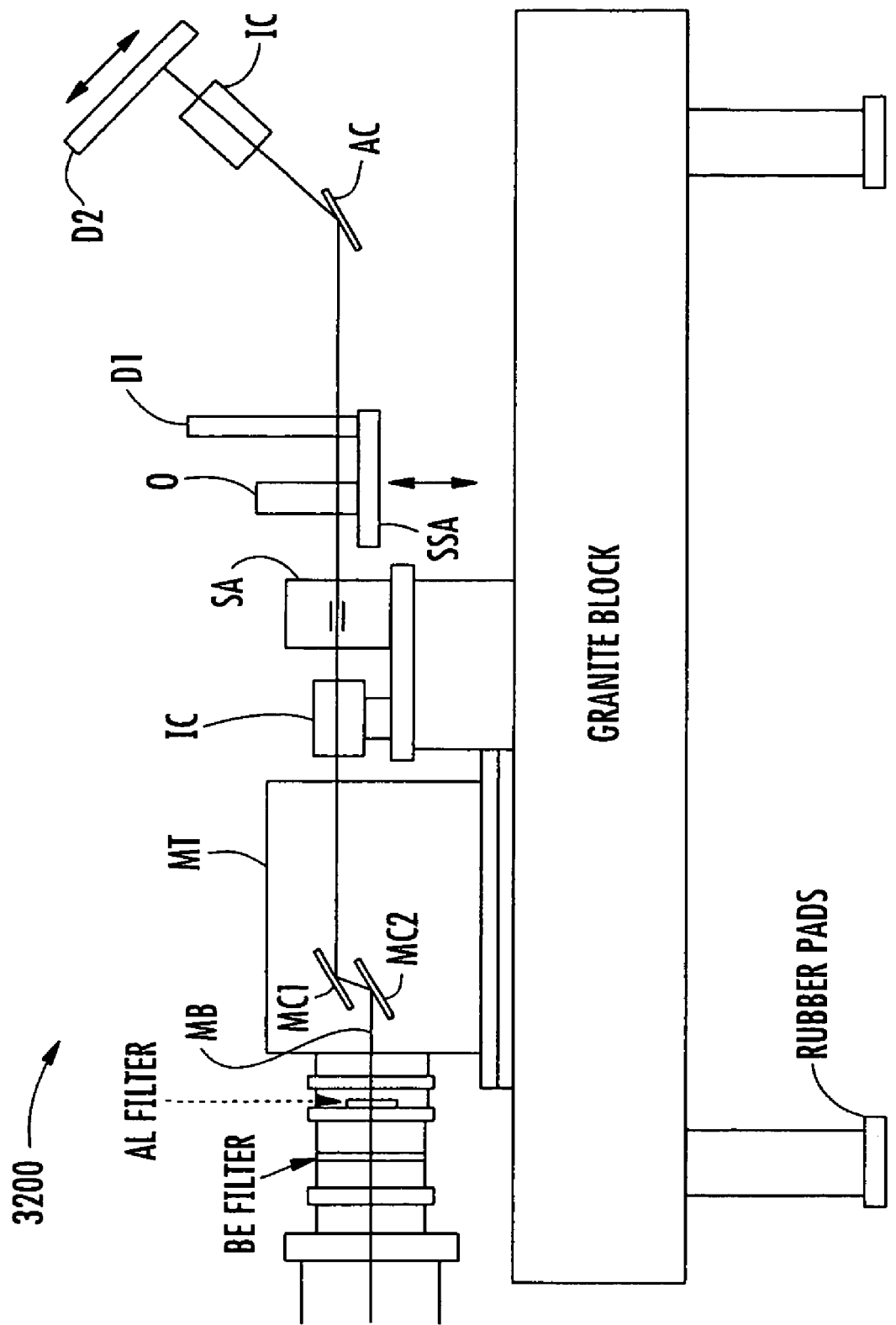
FIG. 32 is a schematic diagram of the experimental setup of a DEI system using a synchrotron X-ray beam according to an embodiment of the subject matter described herein.

The X-ray ring at the NSLS is a 2.8 GeV synchrotron, capable of producing high flux X-rays from 10 to 60 keV. FIG. 32 is a schematic diagram of the experimental setup of a DEI system, generally designed 3200, using a synchrotron X-ray beam according to an embodiment of the subject matter described herein. Referring to FIG. 32, an X-ray beam XB emitted from the synchrotron are highly collimated with a vertical divergence of approximately 0.2 milli-radians. A beamline pipe (not shown) 16.3 meters in length connects the experimental hutch to a synchrotron X-ray ring. The high intensity polychromatic X-ray beam XB enters the experimental hutch and is rendered monochromatic through the use of a double crystal monochromator tank MT. Monochromator tank MT includes two monochromator crystals MC1 and MC2 (each 150 mm wide×90 mm wide×10 mm high) that are both water-cooled to reduce thermal loading. X-ray beam XB exiting monochromator tank MT is monochromatic.

The monochromatic X-ray beams then proceed through an ion chamber IC and high speed shutter assembly SA to a sample stage assembly SSA, creating a line source X-ray beam with maximum dimensions of 120 mm in width and 3 mm in height. With the beam position fixed, a sample object O on assembly SSA is moved through the X-ray beam using a translation stage driven by a stepper motor.

Conventional radiographs can be obtained by placing a detector D1 (in radiography configuration) directly behind sample object O in the beam path, removing any effects of an analyzer crystal AC. Images acquired in this configuration are similar to conventional X-ray systems in that absorption is the primary contrast mechanism, but synchrotron radiographs have been shown to have better contrast when compared to images acquired using conventional X-ray systems. The conventional radiographs obtained during the experiments provided herein were used for comparison to DEI images.

DEI images can be acquired by placing detector D2 (in DEI configuration) after analyzer crystal AC at an angle twice that of the calculated Bragg angle. A summary of the angles used for imaging in the 18-60 keV range is presented in Table 1 above. The use of a line source X-ray makes it necessary to move the detector in a direction opposite that of the sample for DEI and in the same direction for obtaining synchrotron radiographs. In this experiment, DEI images were acquired using a Fuji BAS2500 image plate reader using Fuji HR V image plates (available from Fuji Medical Systems of Stamford, Conn.). The plates are approximately 0.5 mm in thickness composed of a flexible plastic plate coated with a photostimulable phosphor (BaFBR:Eu$^{2+}$) combined with an organic binder. Images are scanned using the FUJI BAS2500 at a resolution of 50 microns and 16-bit gray level.

Further, in another experiment, a digital detector was added to the system to enable DEI applications that were not practical or possible using image plates, including Diffraction Enhanced Computed Tomography and Multiple Image Radiography (MIR). An exemplary detector that may be used includes a Shad-o-Box 2048 (available from Rad-icon Imaging Corp of Santa Clara, Calif.) with a 50×100 mm active area and 12-bit output. This detector utilizes a photodiode array containing 1024 by 2048 pixels with 48 micron pixel spacing in direct contact with a Gd$_2$O$_2$S scintillator screen. Another exemplary detector includes a Photonic Science VHR-150 X-ray camera (available from Robersbridge of East Sussex, United Kingdom) with a FOV of 120 mm×80 mm and a 30 micron pixel size. Both of these exemplary detectors can be mounted in the same manner as the image plate, either in a radiography or DEI configuration.

Acquiring images across the analyzer crystal rocking curve without an object in the beam can generate an intrinsic rocking curve, which represents the convolution of the monochromator and analyzer crystal at different levels of analyzer reflectivity. The intrinsic rocking curve will not be altered by absorption, refraction, or ultra-small angle scatter, which can make it an excellent reference point. When an object is placed in the beam, changes in the rocking curve on a pixel by pixel basis can be use to determine which X-ray interactions are leading to contrast in a given pixel.

The model used in the ERA method models the rocking curve as a Gaussian distribution, which is an approximation, since the rocking curve is a convolution of the monochromator and analyzer, and is triangular. The formula for this model is provided by the following equation:

$$R(\theta_A) = e^{-\mu_T t} \int_{-\infty}^{\infty} \left\{ e^{-\chi_x t} \delta(\theta) + \frac{1}{\sqrt{2\pi} \, \omega_s} (1 - e^{-\chi_s t}) e^{\frac{-\theta^2}{2\omega_s^2}} \right\} \times R_{int}(\theta - (\theta_A - \theta_Z)) d\theta$$

where $\mu_T$ is the linear absorption coefficient, $\chi_s$ is the extinction coefficient, t is the object thickness, $\theta_z$ is the refraction angle, and $\omega_s$ is the Gaussian with of scatter distribution.

MIR is a more refined version of the ERA method. MIR addresses many of the problems present in prior processing techniques and allows for a more complete description of the image contrast components. As stated above, images processed using an MIR technique can generate not only an absorption and refraction image, but also generates an ultra-small angle scatter image. MIR has also been shown to correct for substantial errors present in the DEI apparent absorption and refraction images and is more robust to noise.

As with the ERA method, MIR uses the analyzer crystal rocking curve to generate images representing an object's absorption, refraction, and ultra-small angle scatter. If the intrinsic rocking curve is the baseline, then changes that decrease the area under the curve can be interpreted as absorption alone since photon absorption will decrease overall intensity. For a purely refractive event, the centroid of the rocking curve will be shifted, but the width of the rocking curve will remain constant. Interactions that lead to ultra-small angle scattering will scatter photons across the angular distribution of the rocking curve, which will cause the curve to widen. Assuming that photons are not scattered outside the acceptance window of the rocking curve, scattering effects will not affect the area under the curve, just the shape of the curve. If the rocking curve is assumed to be Gaussian in nature, then the variance of the curve can be used to represent the amount of scattering present.

The rocking curve width decreases as energy increases, which may make it necessary to modify the sampling procedures to account for this change. At 18 keV the rocking curve FWHM is 3.64 microradians, and decreases to 1.11 microradians at 60 keV. As the rocking curve narrows, the angular range over which refraction contrast is significant is reduced. To compensate for this, the angular sampling range and increment may be reduced. The increased slope of a 60 keV rocking curve is beneficial in that it generates a larger change in intensity per microradian. When using flux limiting x-sources such as an X-ray tube, these properties may be maximized to generate the most refraction possible for a given flux.

DEI System Stabilization

Use of the analyzer crystal to convert angular changes to intensity allows for exceptional contrast, but an assumption in this technique is that the analyzer crystal rocking curve position remains constant over time. In practice, this is not the case, and with such a narrow rocking curve width even small changes in the analyzer peak position can create significant errors in the acquired image. The application of processing algorithms, such as DEI apparent absorption and refraction images, MIR, and MIR-CT requires a high degree of system stability. Achieving the goal of determining the absorption, refraction, and scatter parameters in breast tissue required a systematic engineering analysis of the NSLS X-15A beamline to isolate the factors causing instability.

Stability for a DEI system in this case will be defined as the ability to maintain a constant peak position of the analyzer crystal rocking curve over an extended period of time. To review, the polychromatic X-ray beam is incident on the first crystal in the monochromator, which is tuned to a particular angle using Bragg's Law to select a single photon energy. The diffracted monochromatic beam then encounters the second monochromator crystal, the function of which is to redirect the beam to a direction parallel to the incident beam and aligned with the analyzer crystal. When tuning the system for a particular energy, the first monochromator crystal is aligned first, and then the second crystal is tuned to find the position of the beam. The monochromator tank is constantly flushed with helium to reduce the generation of ozone, which can quickly oxidize and damage critical components in the tank.

With the second monochromator crystal aligned, the analyzer is scanned to find the position of the beam on the crystal. Rocking the crystal to find the beam position is analogous to scanning a radio dial to find a particular station, generating a sharp rise in intensity when the angular position of the analyzer is in perfect alignment with the second monochromator crystal. Once the analyzer is aligned, the system is tuned and ready for use.

Factors that can create drift in a DEI system fall into three categories: vibratory, mechanical, and thermal. The optical portion of a DEI system is sensitive to vibrations, since even minor vibrations on the crystals can cause minor changes in angle, resulting in changes in contrast. A large granite slab was used at the NSLS X-15A beamline to dampen vibrations from the external environment. Measurements using an oscilloscope to monitor the post-analyzer X-ray beam indicate that there is approximately a 2-3% variation in intensity, which is attributed to vibrations from external drive fans and pumps at the beamline.

A plurality of motors were used to align the crystals, translate the sample stage and detector assembly. Picomotor drives can be used with the first monochromator crystal, second monochromator crystal, and the analyzer crystal to adjust the theta angle. The second monochromator crystal and the analyzer crystal use a second picomotor to adjust the chi angle. Any instability in these drive motors can create major deviations in the alignment of the system, and mechanical drift was initially thought to be a primary cause of DEI system instability. The motors used to drive the sample stage and detector assembly are important for image quality, but they do not contribute to the stability of the X-ray beam.

A third contributor to system instability is thermal, resulting from both the heat produced from the incident X-ray beam and the system drive motors and amplifiers. While thermal variations in the system were known to have some effect on system stability, it was not considered a primary destabilizing factor. The link between thermal variations and system instability became evident when a critical observation was made, drift in the analyzer was relatively consistent and periodic. In this example, there is only one variable in a DEI system that is periodic, and that is the heat generated and lost by opening and closing the main X-ray shutters.

Experimental tests and observations obtained to isolate sources of instability point to the expansion and compression of the silicon crystal structure as a primary source of drift. A simple explanation of these experimental observations can be found using Bragg's law ($\lambda = 2d \sin(\theta)$). Considering one crystal set to a given angle to diffract a desired energy, any change in the d spacing of the lattice structure can change the angle of the diffracted beam. The heat generated from the X-ray beam in the monochromator can cause the silicon crystal to expand in accordance with its coefficient of linear expansion, $\Delta d/d = 3 \times 10^{-6} \Delta T$ (° C.).

Using Bragg's law and solving for d, one obtains the following equations:

$$\lambda = 2d \sin\theta$$

$$d = \frac{\lambda}{2\sin\theta}.$$

Taking the derivative of the above equation yields $$\Delta d = -\left(\frac{\lambda}{2}\right)\left(\frac{1}{\sin^2\theta}\right)(\cos\theta)\Delta\theta.$$

Substituting for d and rearranging yields $$\frac{\Delta d}{d} = -\left(\frac{\cos\theta}{\sin\theta}\right)\Delta\theta = \frac{-\Delta\theta}{\tan\theta},$$

which can be rearranged to $$\Delta\theta = -\tan\theta\left(\frac{\Delta d}{d}\right).$$

Substituting the silicon linear expansion coefficient for $\Delta d/d$ yields the following equation:

$$\Delta\theta = -3 \times 10^{-6} \tan\theta \Delta T.$$

Using the Bragg angles for 18 keV and 40 keV, 19.2 and 8.4 degrees respectively, it may be expected to see an angular change of 1.05 microradians per degree Celsius at 18 keV and 0.44 microradians per degree Celsius at 40 keV. Using this calculation as a theoretical explanation of drift, it can be expected to see overall beamline stability increase and analyzer drift decrease with increasing beam energies.

Initial analyzer stability tests indicated that the system was highly unstable, with a stability of the peak analyzer position averaging less than 60 seconds. While this may be acceptable for single image scans, it was unacceptable for MIR and any CT applications. Multiple drift assessments measuring the change in analyzer position from a cold start through 12 hours of continuous operation were between 50 and 100 microradians. With an awareness of the importance of temperature on system stability, a comprehensive assessment of all systems components was performed to determine which heat sources could be moderated or eliminated.

Figure 33:
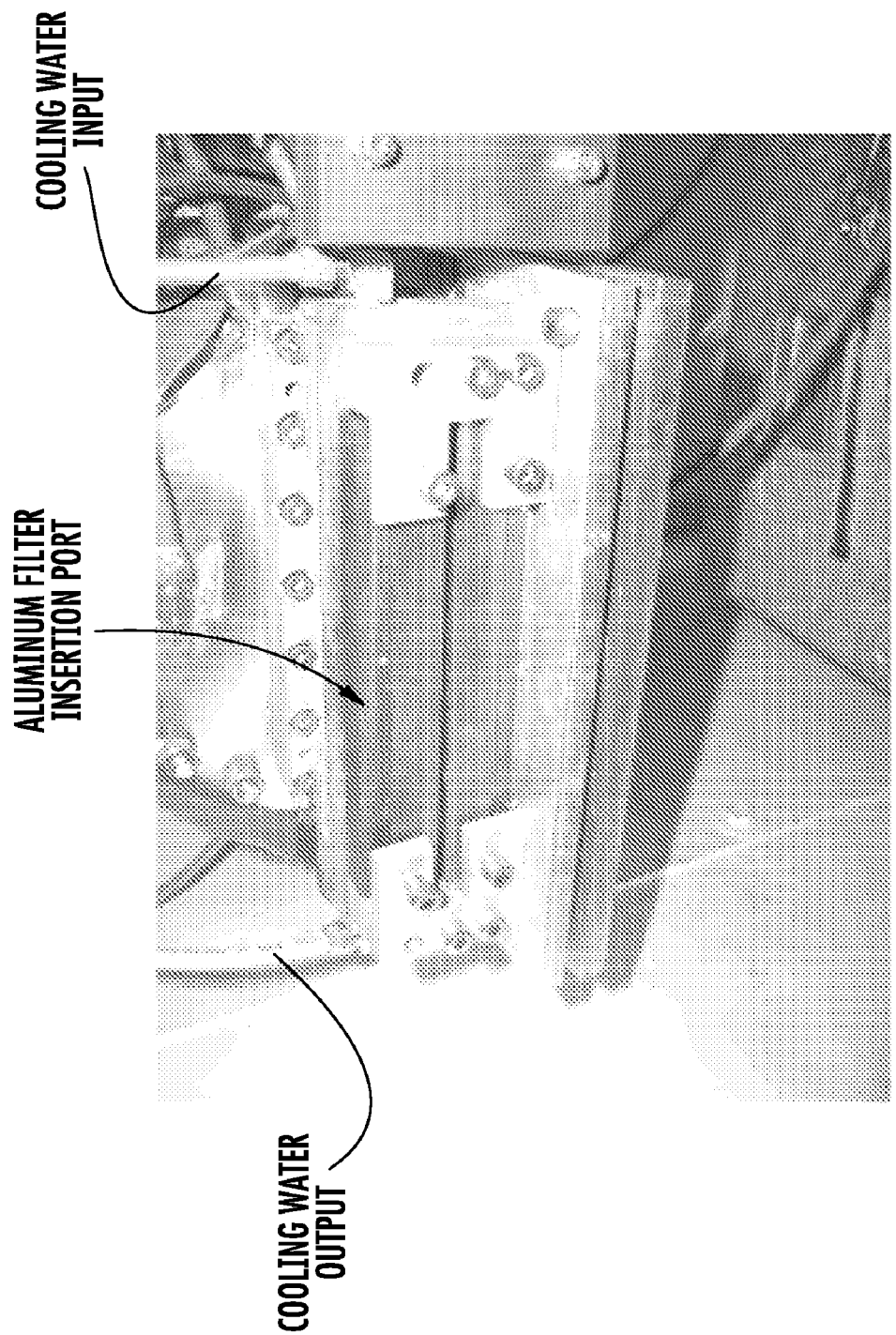
FIG. 33 is an image of an exemplary aluminum filter heat sink according to the subject matter described herein.

One system component that experiences large variations in temperature is the aluminum filter assembly, whose function is to attenuate unwanted low energy X-rays. These 0.5 millimeter thick aluminum sheets heat up quickly when exposed to the synchrotron white beam, and cool off rapidly when the beam is turned off. The proximity of the aluminum filter assembly to the thermally sensitive crystals in the adjacent monochromator tank made this a primary source of instability. A heat sink was needed to remove heat generated by the filters and thermally isolate the aluminum filter assembly. FIG. 33 is an image of an exemplary aluminum filter heatsink according to the subject matter described herein. Referring to FIG. 33, the aluminum filter insertion port and cooling water input/output tubes are indicated.

A copper filter assembly was configured in the system to thermally isolate the heat generated by the aluminum filters and transfer that heat to circulating, high-flow chilled water conduit. The aluminum filters were also reduced in size to limit the radiating surface area and increase contact with the copper heatsink. Stability tests acquired after instillation of the water cooled filter assembly indicated that the overall system drift was reduced by approximately an order of magnitude, with 12 hour continuous operation drift measurements averaging negative 6 microradians from a cold start.

The dramatic reduction in overall system drift after the addition of the water cooled filter heatsink made clear the importance of maintaining an isothermal environment for the analyzer and monochromator crystals. However, it should be anticipated to one of ordinary skill in the art that changes to other sources can be effected for further reducing heat. A systematic analysis of each system component and the periodic changes in the external environment was conducted to isolate the remaining sources of thermal drift.

Amplifiers and control systems can be removed from the experimental hutch for reducing heat. Drive motors may also be removed. However, in the present experiment, the drive motors that control the sample stage and detector assembly could not be removed. In addition, the hutch door can be closed to help maintain a constant ambient air temperature. Twelve hour measurements of the analyzer crystal temperature, ambient air temperature, and gravity cooling water temperature did not indicate any substantial changes in temperature. Continued experiments indicated that there were significant thermal variations in the aluminum base of the second monochromator crystal, which is in direct contact and heated by the second monochromator crystal.

A function of the second monochromator crystal is to diffract the monochromatic X-ray beam from the first monochromator crystal and horizontally align the beam with the analyzer crystal. In theory, the interactions of the X-rays with the crystal are elastic, so there should be no heat generation. This is not the case with the first monochromator crystal, since much of the high intensity, polychromatic synchrotron white beam is absorbed in the internal structure of the first crystal. To reduce vibrations, a gravity driven water cooling system was installed into the system for removing excess heat from the first monochromator crystal. Active cooling was not required for the second monochromator crystal, but temperature measurements acquired over a period of 24 hours indicated that modifications were necessary.

Figure 34:
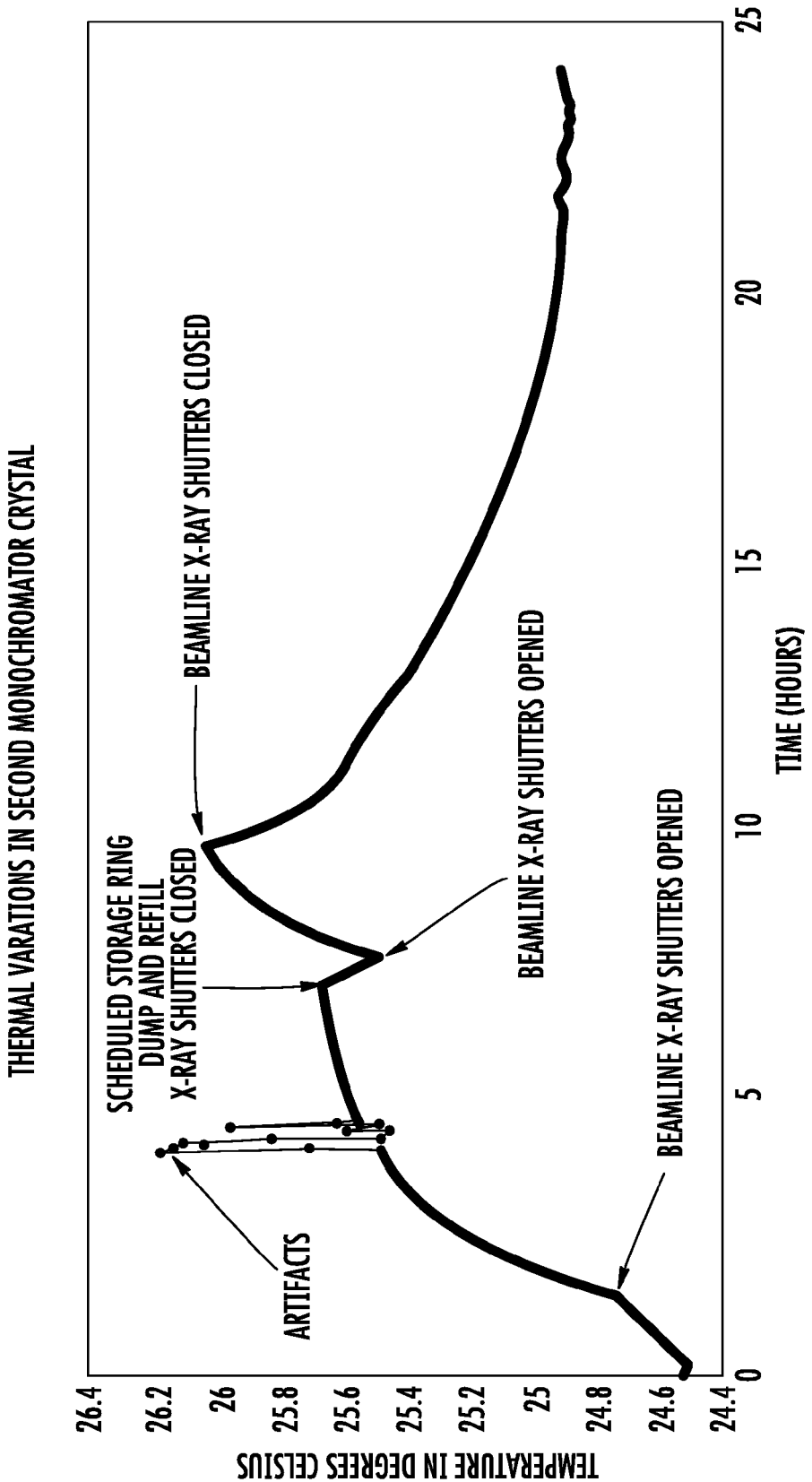
FIG. 34 is a graph of the temperature measured by the thermistor over the 24 hour period.
Figure 35:
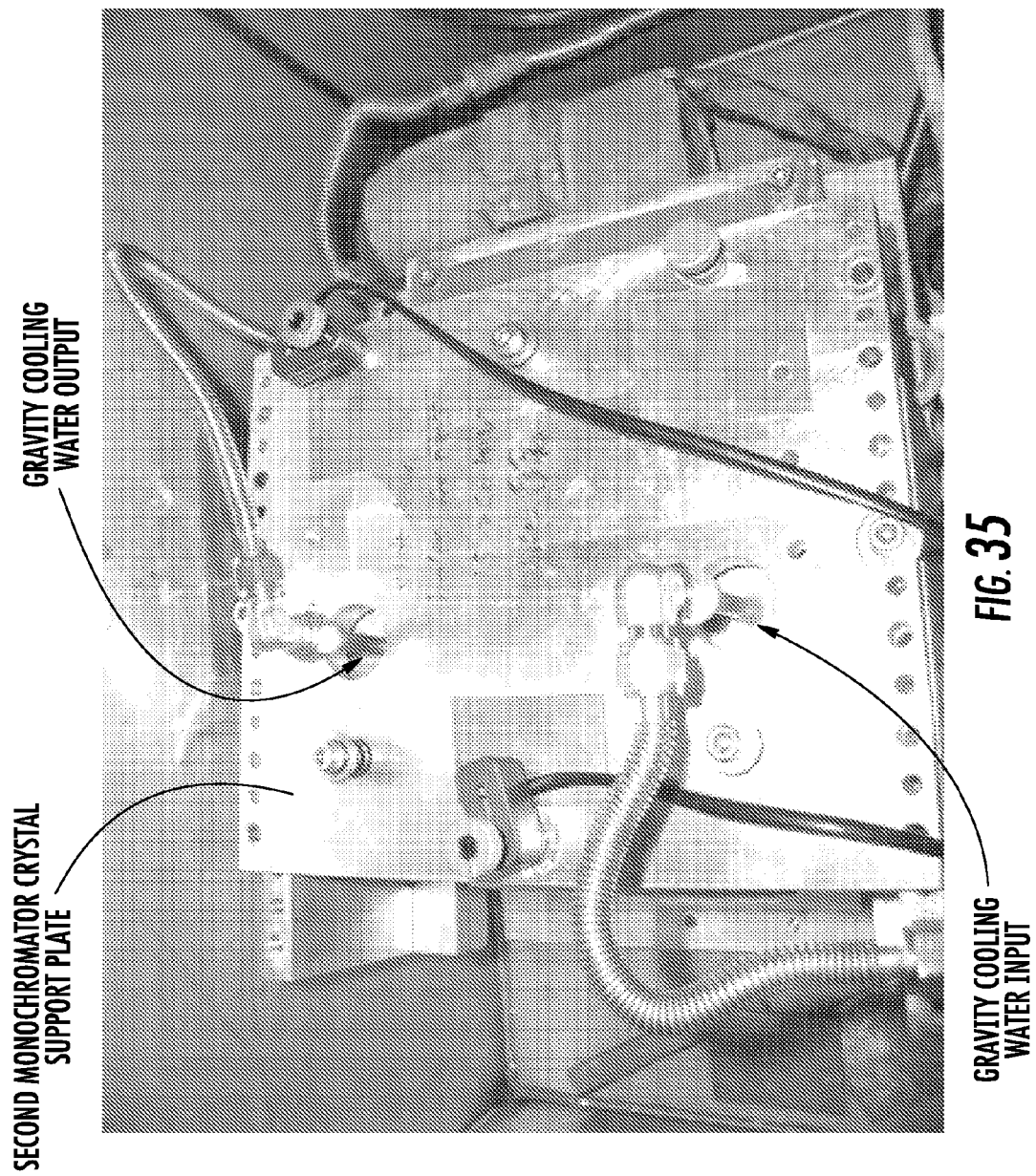
FIG. 35 is an image of an overhead view of an exemplary retrofitted second monochromator base and support plate with water cooling lines for reducing temperature according to an embodiment of the subject matter described herein.

A thermistor was placed on the aluminum support plate and the temperature was measured every 5 seconds over a typical operations period of 24 hours. FIG. 34 is a graph illustrating the temperature measured by the thermistor over the 24 hour period. The temperature of the support plate increased approximately 1.3° C. from the period where the beam was turned on and off. The current of the synchrotron storage ring falls off slowly with time and has to be dumped and refilled, which is evident in the temperature graphs. After 12 hours of continuous operations, the beamline was shut down to determine how long it takes for the temperature to return to baseline. An analysis of the data indicates that there was enough heating on the second crystal to justify retrofitting the support plate for active water cooling. The graph of FIG. 34 is annotated with text of how normal beamline operations influenced crystal temperature. With this source of thermal instability identified, a copper support plate was provided with an internal conduit for water flow and heat exchange. FIG. 35 is an image of an overhead view of an exemplary retrofitted second monochromator base and support plate with water cooling lines for reducing temperature.

After approximately 2000 hours of beamline operations, 1000 hours with the upgraded monochromator, a predictable trend in the stability of the beamline has been measured and evaluated. As predicted, the overwhelming factor in maintaining stability in the optics is temperature. The absolute value of the temperature is not as important as the changes in temperature over time. If an isothermal environment is maintained, then the system reaches equilibrium and there is little or no drift in both the monochromator and analyzer crystals. Imaging at the NSLS presents a unique problem since the ring current in the storage ring decreases slowly but predictably with time. The intensity of the incident X-rays on the first monochromator crystal will decrease in proportion with the ring current, causing the temperature of the first crystal to decrease with time. If no active feedback controls are placed on the crystal system, the first analyzer crystal may contract over time, slowly changing the d spacing and diffracted energy. A change in the Bragg angle on the first crystal will change the position of the beam on the second crystal, reducing the diffracted monochromatic photon flux emitted from the second crystal. This will both reduce the intensity of the X-ray beam incident on the analyzer crystal and change the position of the X-ray beam, resulting in analyzer drift.

The effect of analyzer drift is most clearly demonstrated during a cold startup of the beamline, where all of the beamline components have been at room temperature for at least 24 hours with the X-ray shutters closed. A series of stability tests were performed to test how the analyzer drifts within the first 100 minutes after startup, with the practical purpose of determining how long it takes the system to reach equilibrium. Short term stability testing of the analyzer was accomplished by aligning the system immediately after enabling the X-ray shutters and resetting the analyzer position to zero. The analyzer was then scanned every 100 seconds over a range of $-10$ to 10 microradians with a theta increment of 0.2 microradians. Each rocking curve was subsequently analyzed to determine the center of gravity for each rocking curve, which was recorded as the peak position and recorded along with its corresponding analyzer position. Once the system was initially tuned and the experiment initiated, no further tuning or adjustments were made.

Two photon energies were selected for testing, 18 keV and 40 keV, with all other beamline parameters and aluminum filtration set to the levels used under normal imaging conditions. Higher energy X-rays are far more penetrating than lower energy X-rays, and require more pre-monochromator filters to both reduce the flux to the desired level and attenuate lower energy X-rays that are present in the polychromatic synchrotron white beam. Increasing the amount of filtration increases the amount of absorption that occurs before the X-rays enter the monochromator, thus reducing the heat load on the first monochromator crystal. With the addition of a water cooled heatsink to remove the heat generated from X-ray absorption occurring in the filter assembly, the crystals experience less thermal effects from the synchrotron white beam. The combination of reducing the angular change per degree Celsius at higher energies and the reduction of heat load on the monochromator by increased filtration leads to a proportional increase in stability with increasing beam energy.

Stability experiments conducted from a cold startup of the beamline demonstrate this effect, with the analyzer drift closely following the decrease in ring current. The current theory hypothesizes that the powerful incident synchrotron white beam almost instantly deep heats the first monochromator crystal, quickly reaching a maximum temperature. As the ring current dissipates with time, the temperature slowly decreases, resulting in drift. The system eventually heats up the surrounding ambient air and system components, causing the amount of drift per unit time to stabilize. The increased amount of filtration at 40 keV helps to reduce the effects of thermal load, decreasing the amount of time for the system to reach thermal equilibrium. Once the beamline has been in continuous operation for 5-7 hours, the effects of heat load on each of the crystals were minimized and the beamline becomes ultra-stable with little to no analyzer drift.

Figure 36:
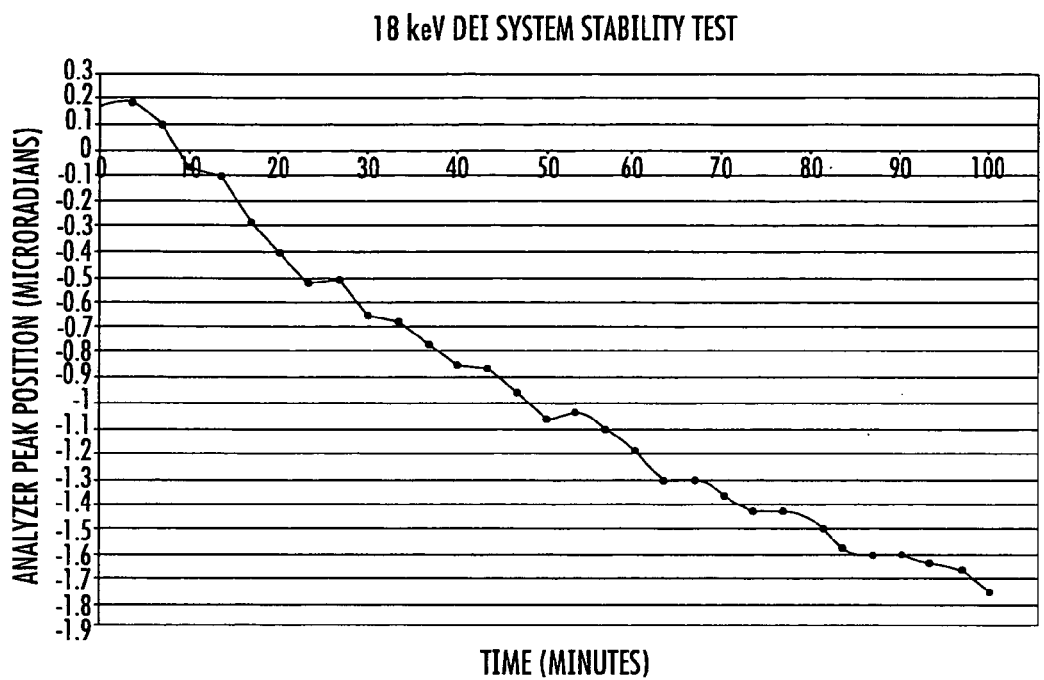
FIG. 36 is a graph of an 18 keV system stability test showing the analyzer peak position over a period of time.
Figure 37:
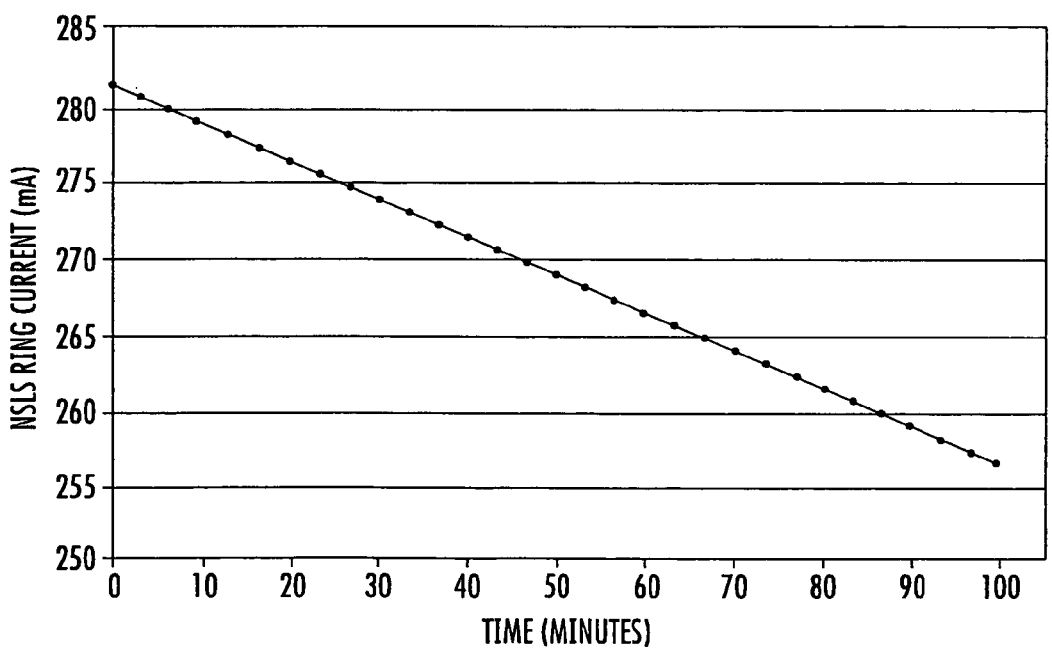
FIG. 37 is a graph of the National Synchrotron Light Source (NSLS) X-ray ring current during the 18 keV stability tests.
Figure 38:
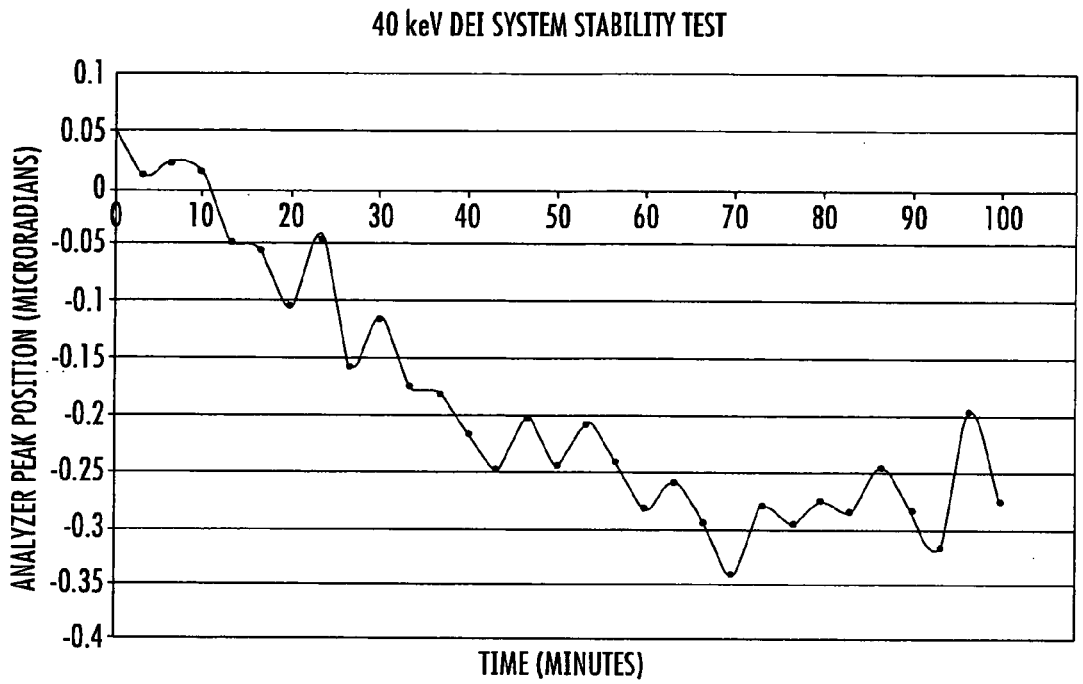
FIG. 38 is a graph of a 40 keV system stability test showing the analyzer peak position over a period of time.
Figure 39:
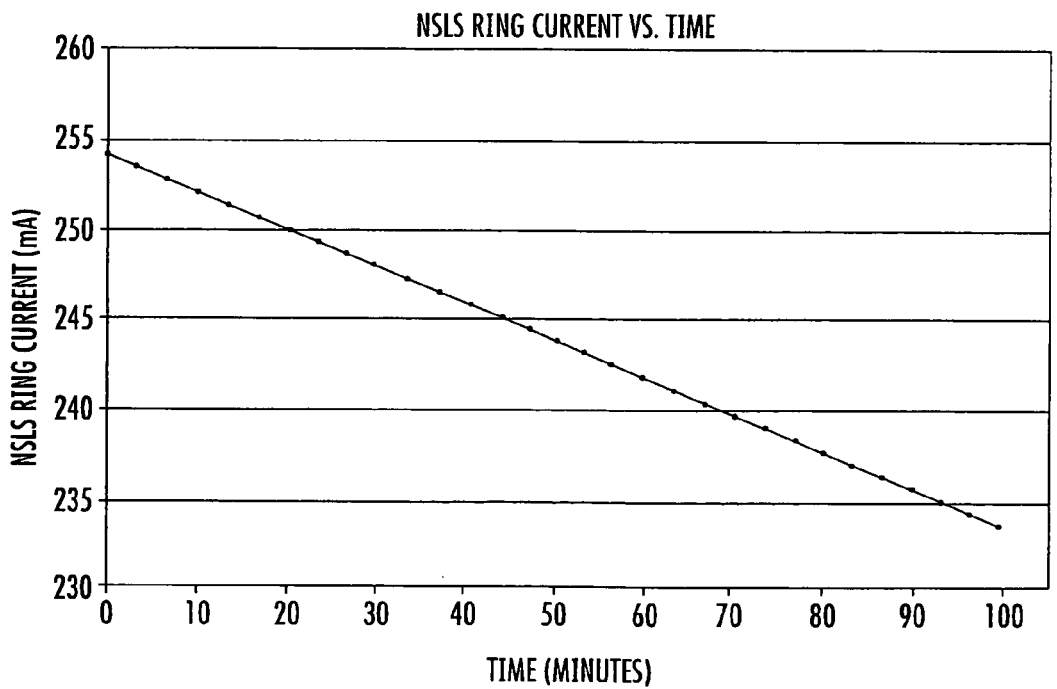
FIG. 39 is a graph of the NSLS X-ray ring current during the 40 keV stability test.

FIGS. 36-39 are graphs of stability test results. In particular, FIG. 36 is a graph of an 18 keV system stability test showing the analyzer peak position over a period of time. FIG. 37 is a graph of the NSLS X-ray ring current during the 18 keV stability tests. FIG. 38 is a graph of a 40 keV system stability test showing the analyzer peak position over a period of time. FIG. 39 is a graph of the NSLS X-ray ring current during the 40 keV stability tests.

The results of this experiment demonstrate that drift in the optics can be controlled by keeping the crystals in the optics isothermal, which can be achieved on both synchrotron and non-synchrotron based DEI systems using a precision heating system to maintain constant temperature. Through a systematic engineering analysis, the problem of analyzer/monochromator instability has been reduced from a fundamental limitation to a minor annoyance. With further refinement, the problem may be removed entirely, allowing for the full utilization of all computed tomography based DEI and MIR methods.

Reader Study Analysis of Mammography Phantoms to Determine Optimal Imaging Parameters for DEI and DEI As set forth above, DEI is a radiographic technique that obtains contrast from X-ray absorption, refraction, and ultra-small angle scattering (extinction contrast). DEI is a similar radiographic technique that obtains contrast from X-ray absorption and refraction. Conventional radiography systems, both planar and CT, produce images based on the attenuation of X-rays as they pass through matter. Since X-ray absorption is based on electron density and mean atomic number, contrast is obtained based on attenuation differences in an object or patient. Interactions of X-ray photons with matter can provide for more structural information than just the number of photons removed from the incident beam. DEI incorporates a silicon analyzer crystal in the path of the X-ray beam that acts as an exquisitely sensitive angular filter, facilitating the measurement of X-ray refraction and ultra-small angle scatter. Objects possessing nominal absorption contrast, either due to the properties of the object or its local environment, may have high refraction and ultra-small angle scatter contrast.

DEI can have tremendous potential in breast imaging given that the structures of interest in breast tissue typically have low absorption contrast, especially in the early stages of disease. DEI studies of malignant breast tissues have indicated a substantial increase in visualization of spiculations in breast tumors when compared with conventional mammography. Primary diagnostic structures of interest in the breast include calcifications, masses, and fibrils, all of which may have significant refraction and scatter signatures when compared to the surrounding adipose and glandular tissue. In order to properly investigate the utilization of DEI for mammography, the unique system parameters and configurations must be optimized to detect the features diagnostically important for breast imaging. An integral component of this study is to determine the potential decrease in radiation dose that can be achieved using absorption, refraction, and ultra-small angle scatter rejection (extinction). The primary DEI imaging components that must be specified in order to design and construct a clinically useful mammography system are beam energy, analyzer crystal reflection, and position on the analyzer crystal rocking curve.

Experiments for this study were carried out at the X-15A beamline at NSLS. In order to understand the parameters being analyzed, a brief description of the system is in order. The X-ray source for these experiments was an X-ray ring at the NSLS is a 2.8 GeV synchrotron, capable of producing high flux X-rays from 10 to 60 keV. A double crystal silicon monochromator was used to select a particular energy from the incident X-ray beam. DEI images were obtained by placing a silicon analyzer crystal behind the object which was tuned to select a particular angle. The analyzer is an angular filter with a resolution on the order of tenths of microradians, which facilitates the measurement of X-ray refraction and ultra-small angle scatter. Tuning the analyzer to different positions on its reflectivity curve can select discrete angles in the X-ray distribution, and some positions provided useful information for object and lesion detection.

There are multiple crystal reflections that can be used in DEI, such as the Bragg [111] and Bragg [333] reflections. DEI refraction contrast increases with the slope of the analyzer crystal rocking curve, with the Bragg [333] reflection having a much steeper slope than the Bragg [111] reflection. The Bragg [333] reflection can provide better contrast, but the number of X-ray photons that can be selected from the incident polychromatic X-ray beam by the crystal in the Bragg [333] reflection is roughly an order of magnitude less than the Bragg [111] reflection. Determining the relative difference in visualization between these reflections can be an important factor in the design on a clinically based DEI system.

X-ray tubes can use a cathode/anode configuration to produce X-rays, with the output spectrum and amplitude a function of the anode material, voltage, and amperage. Mammography systems can include an X-ray source having a molybdenum target at voltages ranging from 28 to 32 kVp for producing an X-ray beam. This configuration produces a polychromatic, diverging X-ray beam with an energy spectrum centered around the $K_\alpha$ of molybdenum, 18 keV. Absorption based X-ray systems are set to these relatively low energy X-rays for imaging soft tissue. While 18 keV X-rays provide great contrast in soft tissues, one drawback is the increased patient absorbed dose associated with lower energy X-rays. Some previous DEI breast imaging studies were based on an X-ray energy comparable to conventional mammography systems. While these techniques may have potential utility in measuring X-ray absorption, it does not adequately address the advantages of the additional DEI contrast mechanisms of refraction and ultra-small angle scatter.

There are several image processing techniques that can be applied to DEI, including the creation of apparent absorption and refraction images. Another evolving DEI based image processing method is MIR, which is a more accurate and detailed separation of the contrast components. Preliminary studies using MIR have demonstrated that this method is capable of operating at low photon count levels, and has potential use with conventional X-ray sources. Several groups working with DEI are in the process of applying the DEI method to CT, which combines the additional contrast mechanisms of DEI with spatial resolving capability of CT. While this study focused on planar imaging, the system parameters for planar imaging can also be applied to both synchrotron and non-synchrotron-based CT applications.

The experiments that will be described herein involve the careful variation of the acquisition parameters during the imaging of standard mammography phantoms. Images acquired for the study represent the raw image data acquired at each system configuration, without any secondary image processing. Expert readers scored the visibility of the known phantom features under all experimental conditions in order to assist in the specifications of an ideal DEI mammography unit.

From both an engineering and medical perspective, one of the most important system parameters is beam energy. In order to gain an understanding of how structural visualization changes as a function of energy in DEI the following energies were chosen for the study: 18 keV, 25 keV, 30 keV, and 40 keV. Selection of the desired energy from the incident synchrotron beam was accomplished by tuning the monochromator to the appropriate Bragg angle for the desired wavelength.

Three representative points across the analyzer crystal rocking curve may be used during analysis for obtaining diagnostically valuable information. The −½ Darwin Width (DW), peak, and +½ DW positions were selected for each beam energy/crystal reflection combination. A corresponding synchrotron radiograph was obtained for comparison.

Standardized breast imaging phantoms were used in this experiment to simulate the structural characteristics of breast tissue and breast cancer. Initial efforts involved actual breast tissue specimens, but the variation present in biological tissues and subjective evaluation of malignant features made the use of phantoms more appropriate for this study. Since DEI systems in accordance with the subject matter described herein are capable of obtaining contrast from multiple mechanisms, phantoms were selected with features amenable to each. In this experiment, a contrast-detail (CD) phantom (available from the Sunnybrook and Women's Research Institute at Toronto, Ontario, Canada) made of Lucite with a series of circular indentions of varying diameter and depth machined into the surface was selected. The variation in diameter and depth creates a gradient useful in assessing contrast and spatial resolution. Deeper indentations result in an increased difference in attenuation, and therefore increased contrast. The circular edges of the indentions provide an interface conducive to the refraction of X-rays. With a known radius and height, the volume of each cylinder was calculated to determine the total visible volume.

Figure 40C:
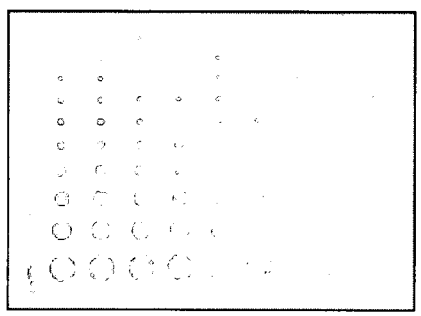
FIGS. 40A-40C are images of an exemplary CD phantom acquired at 18 keV according to an embodiment of the subject matter described herein.
Figure 40B:
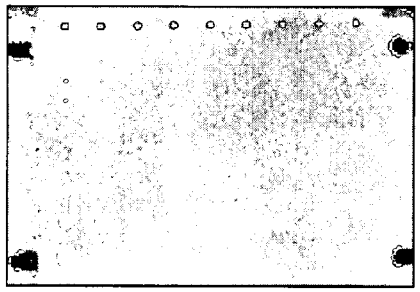
Figure 40A:
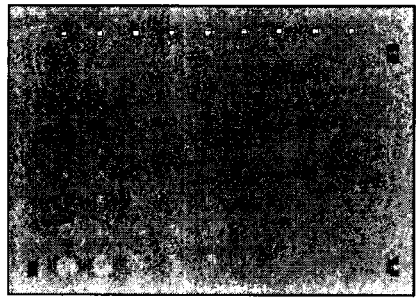

FIGS. 40A-40C and 41A-41C are images of an exemplary CD phantom acquired at 18 keV and 30 keV, respectively. In particular, FIGS. 40A-40C show images of an 18 keV synchrotron radiograph, an 18 keV DEI image acquired in the +½ Darwin Width (DW) analyzer crystal position, and an 18 keV DEI image acquired at the peak analyzer crystal position, respectively. The crystal reflection used in the DEI examples is the Bragg [333] reflection.

Figure 41C:
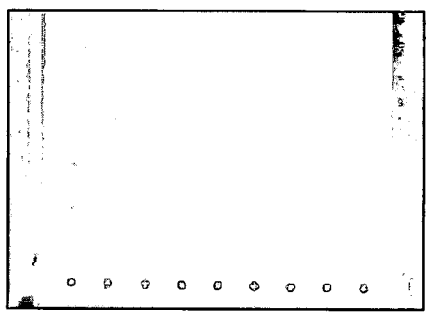
FIGS. 41A-41C are images of an exemplary CD phantom acquired at 30 keV according to an embodiment of the subject matter described herein.
Figure 41B:
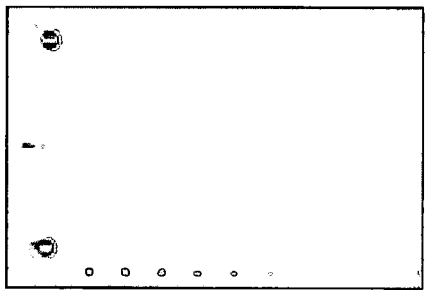
Figure 41A:
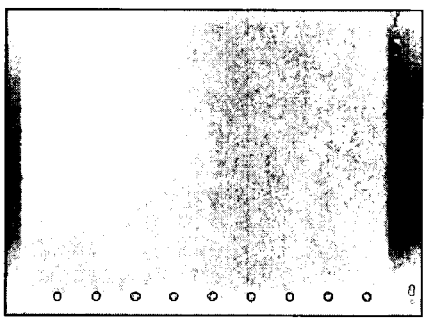

FIGS. 41A-41C show images of a 30 keV synchrotron radiograph, 30 keV DEI image acquired in the −½ Darwin Width (DW) analyzer crystal position, and a 30 keV DEI image acquired at the peak analyzer crystal position, respectively. The crystal reflection used in the DEI examples is the Bragg [333] reflection. Contrast is reduced in the 30 keV synchrotron radiograph as compared to the 18 keV synchrotron radiograph.

A second phantom was used for experimentation. The second phantom was designed for the International Digital Mammography Development Group (IDMDG) to test digital mammography systems. Specifically this phantom was developed for the Digital Mammography Imaging Screening Trial (DMIST) and is known as MISTY (available from the Sunnybrook and Women's Research Institute). The MISTY phantom contains a variety of regions that can be used to quantify mammographic image quality. Structurally the phantom is composed of polymethylmethacrylate (PMMA) with a mercury-intensified overlay containing several high resolution details that can be used to quantify system contrast and resolution.

Figure 42C:
FIGS. 42A-42C are images of the three different regions of the MISTY phantom acquired at 30 keV, Bragg [333], in the peak analyzer crystal position obtained with a system and method in accordance with the subject matter described herein.
Figure 42B:
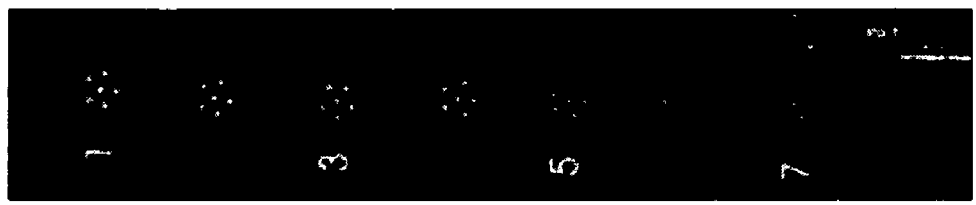
Figure 42A:
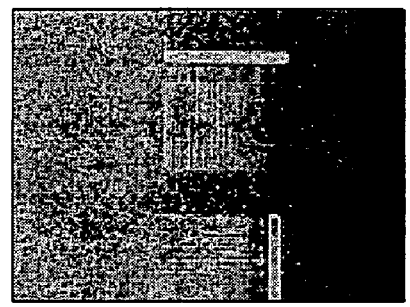

Three regions from the MISTY phantom were selected for use in experimentation. FIGS. 42A-42C are images of the three different regions of the MISTY phantom acquired at 30 keV, Bragg [333], in the peak analyzer crystal position. In particular, FIG. 42A is an image of a series of line pairs clusters, each cluster containing 4 lines, with the distance between the lines decreasing until they can no longer be resolved.

FIG. 42B is an image of a series of star clusters, which simulate calcifications in breast tissue. A column of seven clusters, each containing six stars, was used with each cluster of stars having one star with a missing point. As resolution and contrast decreases, the stars can no longer be visualized and appear only as specks. The calcification simulation was inverted for use in this experiment.

FIG. 42C is an image of a stepwedge. The stepwedge is used to measure absorption contrast. The stepwedge includes 6 well defined interfaces.

In this experiment, DEI images were acquired using the Fuji BAS2500 Image Plate Reader and Fuji HR V image plates. As stated above, the image plates are flexible plastic sheets, approximately 0.5 mm thick, coated with a photostimulable phosphor combined with an organic binder. Further, all images were scanned using a 50 μm pixel size and a 16-bit gray level. The surface dose used for image acquisition varied based on energy, but the same surface dose was used for both the radiograph and DEI images at each energy setting. A surface dose of 3.0 mGy was used for image acquired at 30 keV, 1.5 mGy for images acquired at 25 keV, and 0.2 mGy for images acquired at 40 keV.

Two study readers were involved in the experiment for analyzing the CD and MISTY phantom image results. The use of standardized phantoms combined with the dramatic differences between most of the DEI configurations indicated that two readers would be sufficient to achieve an appropriate level of statistical power. One expert breast imager and one medical physicist participated in the study. In order to optimize the viewing environment, the reader study was performed in a specially designed darkroom using a 5 megapixel CRT monitor with a peak luminance of 500 cd/m$^2$. Readers were allowed to adjust the gray scale of each image and were provided a magnifying glass for maximum visualization.

The ability to visualize the entire circumference of a lesion has diagnostic significance in mammography, an example being the difference between a benign fibroadenoma with well circumscribed borders and a potentially malignant mass with less well-defined borders with or without spiculations. Additionally, visualization of calcifications and their morphology can provide insight into underlying pathology. Questions reflecting the diagnostic application to clinical mammography were integral to the reader study design, separating the task into distinct confidence levels where appropriate.

In determining which factors give the highest performance, eight performance measurements were established for use by the readers:
1. The volume of the circles for which the entire circumference can be seen in the CD phantom;
2. The volume of the circles for which at least half of the circumference is visible in the CD phantom;
3. The volume of the circles for which any part of the circumference is visible in the CD phantom;
4. The number of line pair groups observed in the MISTY phantom;
5. The number of stars that are visible in the calcification simulation of the MISTY phantom;
6. The last cluster number with all points seen in the calcification simulation of the MISTY phantom;
7. The number of specs seen in the calcification simulation of the MISTY phantom; and
8. The number of clearly defined sections in the stepwedge of the MISTY phantom.

In order to facilitate the codification of the data in the images, a graphical depiction of each phantom with the corresponding performance task was provided to each reader to score the images. For the CD phantom, the reader was asked to indicate which circles were visible in each row and column of the image. To assess the MISTY phantom line pair region, the reader was asked to determine the highest cluster where all four lines could be clearly visualized. Scoring of the calcification simulation involved first counting the total number of stars that could be visualized, then counting the number of star points seen in each cluster out of a possible 29 points. In addition, the reader was asked to count the total number of specks that could be visualized. For the stepwedge region of interest, the reader was asked to mark which of the 6 interfaces could be clearly visualized. The order of image presentation was randomized for each reader for scoring.

A multi-way analysis of variance was used to fit all eight outcomes. Included in the analysis were all interactions among beam energy, crystal reflection, curve position, and reader. Box-Cox transformations were applied to some of the outcomes to ensure the validity of normality assumption. Since multiple outcomes were considered when comparing all the factors, a Bonferroni test was used to adjust the overall Type I error by setting 0.05/8 (0.00625) as the significance level. At this significance level, we used the Tukey test to compare the difference in performance among the combinations of all the factors.

CD Phantom Results

For volume of the circles with any part of the circumference visible, there was no significant difference between the two readers (p-value=0.0185) and among different energy levels (p-value=0.0176). However, both crystal reflection and rocking curve position, as well as their interactions, are significant (all three p-values<0.001). Tukey test analysis indicates that more volume can be seen with the Bragg [333] reflection. The radiograph has the least visible volume, and there is little difference among the −½ DW, +½ DW, and peak analyzer crystal positions.

When the outcome is the volume of the circles with at least half of the circumference visible, the main effects of all the factors are significant with p-values less than 0.001. Tukey test analysis indicates that 25 keV performed best, and that both 25 keV and 30 keV produce more visible volume than 18 keV and 40 keV. The data indicates that there is a significant interaction between crystal reflection and analyzer position (p-value<0.001). The combination of the Bragg [333] reflection and peak analyzer position produces the most visible volume, although there is not enough evidence to support that it performs better than the combinations Bragg [333], +½ DW and Bragg [333], −½ DW positions. The synchrotron radiograph produced the least visible volume.

For the volume of the circles with the entire circumference visible, only the main effects of reader, beam energy and rocking curve position are significant with p-values being less than 0.001, equal to 0.0027, and less than 0.001 respectively. Tukey test analysis did not find a difference among all the levels in beam energy, but trends in the data indicate that 25 keV performs better than 30 keV, and the latter performed better than both 40 keV and 18 keV. As with the other performance measurements, the synchrotron radiograph produced the least visible volume.

Misty Phantom

Analysis of the line pair groups indicate that the main effects of beam energy, crystal reflection, and analyzer rocking curve position are significant with all p-values less than 0.001. Moreover, there appears to be significant interactions between the crystal reflection and rocking curve position (p-value<0.001). The data indicates that the combinations of 18 keV, Bragg [333], in the peak analyzer position or 25 keV, Bragg [333], in the peak or +½ DW analyzer position performed well. The best performance for the line pair region is 30 keV, Bragg [333], at a rocking curve position of +½ DW.

Artifacts were present in many of the star cluster images generated by using a phantom designed for diverging X-rays in a system with a highly collimated X-ray beam. The data is presented for completeness and to demonstrate how the overall structural design of conventional phantoms can affect visualization. Analysis of the number of stars visualized indicates that only beam energy is significant, with a p-value of 0.0026. Test results indicate that 25 keV is the best choice, but not significantly different from 30 keV. None of the factors were significant for the last cluster number with all points seen. Data from the number of specks seen indicate that the best combinations are 18 keV and Bragg [111], 18 keV and Bragg [333], as well as 30 keV with either the Bragg [111] or [333] reflection.

For the stepwedge region, there appears to be a significant difference among the difference levels in beam energy and the different rocking curve positions. The data indicates that the beam energies of 18 keV, 25 keV, and 30 keV are roughly equivalent, but all perform better than images acquired at 40 keV. The performance results for the rocking curve position indicate that the positions of −½ DW, peak, and +½ DW are equivalent and equal to the performance of the synchrotron radiograph.

Analysis of all performance measurements indicate that the optimal DEI system configuration is 25 or 30 keV, using the Bragg [333] reflection in either the −½ DW or peak analyzer crystal position. Tables 4-6 show a summary of the reader study data. In particular, Table 4 shows a summary of reader study data with respect to X-ray beam energy. Table 5 below shows a summary of reader study data with respect to crystal reflection. Table 6 below shows a summary of reader study data grouped according to rocking curve position.

TABLE 4

Summary of Reader Study Data with Respect to X-ray Beam Energy

| | CD Phantom Entire Circumference | CD Phantom Half Circumference | CD Phantom Visualization Only | Misty Phantom Line Pairs | IDMDG Phantom Stars | IDMDG Phantom Star Points | IDMDG Phantom Star Specks | IDMDG Step-wedge |
|---|---|---|---|---|---|---|---|---|
| 18 | 127.96 ± 9.58 | 210.49 ± 68.98 | 241.43 ± 19.76 | 1.625 ± 1.147 | 2 ± 3.347 | 0.125 ± 0.341 | 38.562 ± 5.215 | 4.562 ± 0.964 |
| 25 | 185.63 ± 73.62 | 232.04 ± 38.16 | 247.96 ± 9.66 | 1.937 ± 1.181 | 5.187 ± 6.295 | 0.375 ± 0.719 | 41.875 ± 0.341 | 4.312 ± 1.014 |
| 30 | 169.36 ± 96.80 | 227.56 ± 48.73 | 245.16 ± 13.87 | 1.812 ± 1.223 | 3 ± 3.483 | 2.687 ± 10.486 | 39.400 ± 4.702 | 4.687 ± 1.250 |
| 40 | 134.24 ± 107.30 | 198.31 ± 67.93 | 237.85 ± 23.65 | 0.375 ± 0.619 | 0.375 ± 0.885 | 0 ± 0 | 14.937 ± 12.615 | 0.562 ± 1.093 |

TABLE 5

Summary of Reader Study Data with Respect to Crystal Reflection

| | CD Phantom Entire Circumference | CD Phantom Half Circumference | CD Phantom Visualization Only | Misty Phantom Line Pairs | IDMDG Phantom Stars | IDMDG Phantom Star Points | IDMDG Phantom Star Specks | IDMDG Step-wedge |
|---|---|---|---|---|---|---|---|---|
| 111 | 150.96 ± 95.99 | 214.98 ± 46.73 | 242.89 ± 10.74 | 0.969 ± 0.897 | 2.031 ± 3.605 | 1.437 ± 7.414 | 33.935 ± 13.394 | 3.687 ± 2.086 |
| 333 | 157.96 ± 102.42 | 219.22 ± 67.90 | 243.31 ± 22.64 | 1.906 ± 1.328 | 3.250 ± 4.833 | 0.156 ± 0.448 | 33.281 ± 13.056 | 3.375 ± 1.996 |

TABLE 6

Summary of Reader Study Data Grouped According to Rocking Curve Position

| | CD Phantom Entire Circumference | CD Phantom Half Circumference | CD Phantom Visualization Only | Misty Phantom Line Pairs | IDMDG Phantom Stars | IDMDG Phantom Star Points | IDMDG Phantom Star Specks | IDMDG Step-wedge |
|---|---|---|---|---|---|---|---|---|
| Radiograph | 110.61 ± 85.90 | 147.10 ± 72.48 | 218.21 ± 18.46 | 0.5 ± 0.632 | 0.375 ± 0.806 | 0 ± 0 | 29.375 ± 13.490 | 2.875 ± 1.668 |
| Negative ½ DW | 162.24 ± 104.75 | 241.13 ± 21.21 | 251.24 ± 5.32 | 1.687 ± 1.078 | 2.812 ± 4.037 | 2.750 ± 10.478 | 35.667 ± 9.155 | 3.937 ± 1.948 |
| Positive ½ DW | 165.51 ± 102.42 | 238.35 ± 32.28 | 252.28 ± 3.80 | 1.687 ± 1.250 | 3.187 ± 5.128 | 0.250 ± 0.577 | 31.187 ± 18.605 | 3.375 ± 2.094 |
| Peak | 178.83 ± 95.13 | 241.82 ± 18.43 | 250.67 ± 5.60 | 1.875 ± 1.360 | 4.187 ± 5.009 | 0.187 ± 0.403 | 38.312 ± 7.208 | 3.937 ± 2.351 |

With respect to beam energy, the reader study data for both phantoms indicates that energies greater than 18 keV may be optimal for DEI. Since absorption contrast decreases as $1/E^3$, soft tissue absorption contrast decreases rapidly with increased energy for conventional X-ray systems. The reader study results indicate that for higher beam energies the loss of information from absorption is compensated for by information from DEI-specific contrasts. For structures that are primarily refractive, DEI sensitivity is proportional to $1/E$, with the potential for image acquisition in soft tissue at energies at or above 40 keV. The rejection of scattered photons that contributes to extinction is energy independent, but the scattering intensity will decrease as energy increases. Since most key diagnostic structures in breast tissue are believed to have significant refractive and scatter properties, imaging at higher energies may be facilitated by moving away from absorption and focusing on refraction and ultra-small angle scatter contrast.

Increases in visualization for the Bragg [333] reflection are evident in the CD phantom, especially at higher performance levels. The Bragg [333] reflection was superior in the majority of performance measurements, but the difference between this reflection and the Bragg [111] is less than expected. While this may indicate that the Bragg [111] reflection is acceptable given the engineering considerations of flux, the more likely explanation is that the design of the phantoms was inappropriate for measuring contrast mechanisms that are based on X-ray refraction and extinction.

The same reasoning can be applied to the analyzer crystal position, in which the peak analyzer position was superior in the majority of performance measurements. Absorption contrast and resolution is going to be highest when the intensity of undeviated photons is greatest, which is at the peak of the analyzer rocking curve. Extinction effects also play a role at the peak position in that structures that scatter photons to the tails of the rocking curve will be eliminated, resulting in extra contrast. Since these phantoms were designed to test X-ray absorption based imaging systems, it is expected that the peak position would perform best in this type of study. Refraction contrast is not present at the peak of the rocking curve, and the generally equivalent or decreased performance of the −½ DW and +½ DW indicates the absence of structures in the phantom that are highly refractive.

This study was designed to gain insight into the effect each system component has on image quality, not on the image processing method that is most useful. As a first step in narrowing the total imaging parameter space, an analysis of the raw data at each configuration is thus more appropriate than processing DEI image pairs to create apparent absorption and refraction images.

One of the most encouraging outcomes is the ability to use higher energy X-rays, potentially as high as 40 keV. The rapid decrease in the photoelectric effect at higher energies corresponds to a reduced number of photons absorbed in the patient, resulting in a dramatically reduced radiation dose. For the same number of photons reaching the detector ($10^7$ ph/cm$^2$), surface absorbed dose through 5 cm of water at 18 keV is 3.3 mGy, 0.045 mGy at 30 keV, and 0.016 mGy at 40 keV. This represents a 73 fold reduction in dose at 30 keV compared to 18 keV, and a 206 fold reduction at 40 keV. Since absorption increases with tissue thickness, this reduction in dose is even greater for thicker specimens.

Analysis of Breast Cancer Contrast Mechanisms Using Multiple Image Radiography

Breast imaging studies using DEI and MIR techniques have demonstrated improvements in visualization when compared to conventional mammography. In particular, studies using DEI techniques to analyze the underlying contrast mechanisms in breast cancer fibrils demonstrate that X-ray extinction plays a large role in image contrast. Further, studies of breast cancer spiculations have demonstrated an 8 to 33 fold increase in the DEI peak image when compared to a corresponding radiograph. MIR allows for a more complete and rigorous assessment of these properties through the addition of an image representing an object's ultra-small angle scatter.

This study addresses extending the usable energy range of an X-ray source and decreasing or eliminating the need for X-ray absorption. The underlying X-ray contrast mechanisms in breast tissue become critical non-synchrotron based DEI systems, since absorption contrast in soft tissue decreases rapidly with increasing photon energy. Utilizing higher energy X-rays increases the efficiency of a DEI system by increasing the number of incident photons reaching the detector, and a reduction in X-ray absorption reduces both the surface and absorbed radiation dose. However, if absorption is a key contrast mechanisms for breast tissue visualization, then any DEI system may use lower energy X-rays in a range similar to conventional X-ray systems. This experiment compares the system features at 18 keV and 60 keV.

In order to assess the energy dependence absorption, refraction, and scatter in breast tissue, four breast tissue specimens with characteristic features were imaged at multiple X-ray energies and processed using MIR to separate the individual contrast components. The energy range used in the study was determined based on the energies used in conventional molybdenum and tungsten X-ray tubes, 18 keV and 60 keV, respectively. Beam energies of 25 keV, 30 keV, 40 keV, and 50 keV were also selected to closely follow the decrease in contrast for each MIR contrast mechanism.

In one experiment, three breast cancer specimens were selected for imaging at the NSLS X-15A beamline. MIR image sets and synchrotron radiographs were acquired using the X-15A beamline at the NSLS. A Photonic Science VHR-150 X-ray camera was used for image acquisition, with a FOV of 120 mm×80 mm and a 30 micron pixel size.

Figure 43:
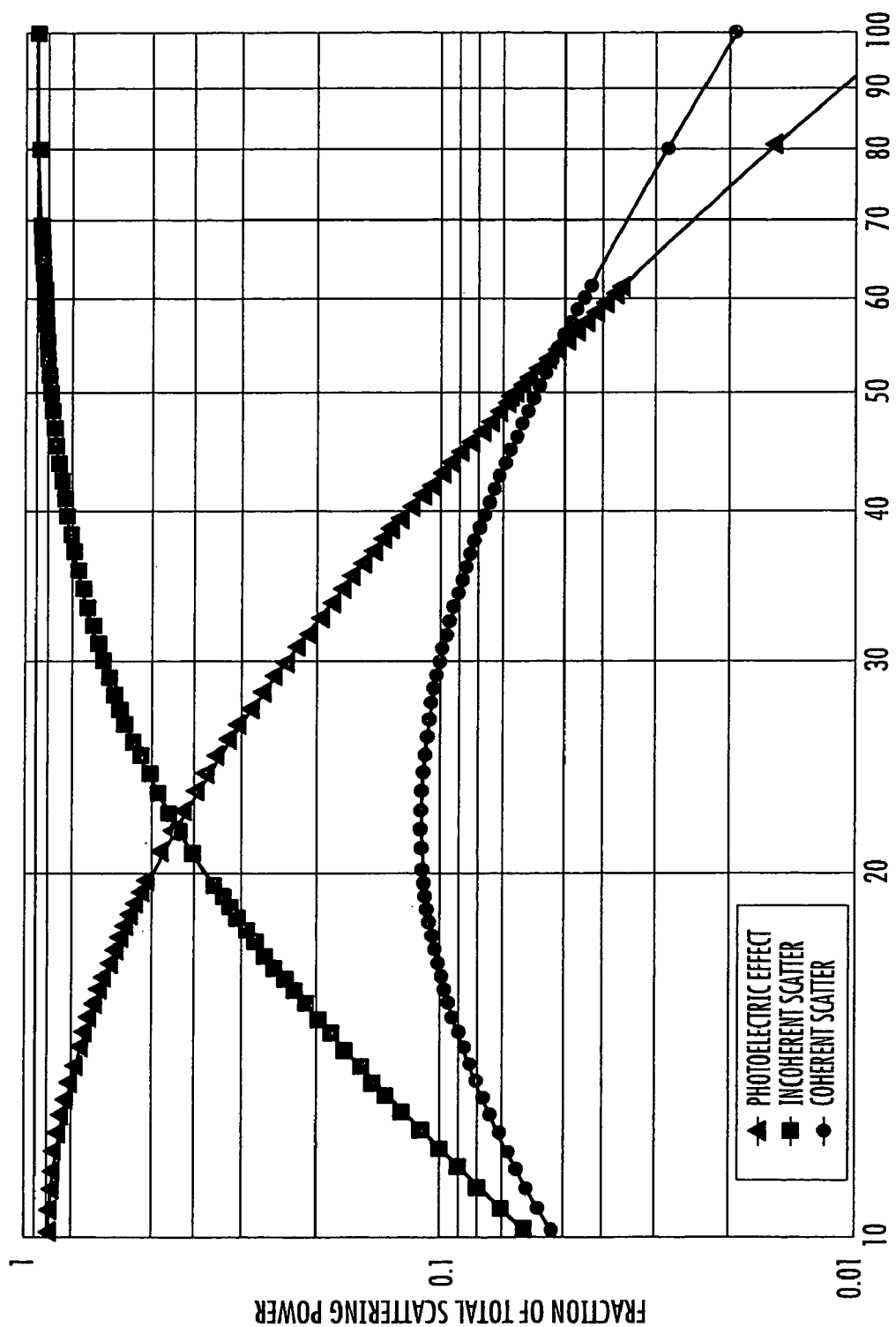
FIG. 43 is a graph of the contributions of absorption, incoherent scatter, and coherent scatter in breast versus energy.

The rapid decrease in the photoelectric effect in relation to X-ray refraction and scatter makes maintaining a constant surface dose challenging. For example, an image acquired using a surface dose optimized for X-ray absorption at 18 keV would be severely overexposed at higher beam energies, such as 60 keV, due to a decrease in photon absorption. A balance was found by tuning the monochromator to the middle of the energy range to be used for MIR imaging, 40 keV, and selecting a surface dose to make the average exposure was approximately half the dynamic range of the detector. A surface dose of 350 mrad was selected for MIR and radiograph imaging at 18 keV, 25 keV, 30 keV, and 40 keV. The surface dose used at 50 keV and 60 keV was reduced due a sharp decrease in photon flux at those energies from a bending magnet X-ray source, with a surface dose of 20 mrad at 50 keV and 4 mrad at 60 keV. The full width at half maximum (FWHM) of the analyzer crystal rocking curve decreases as the energy increases. Refraction contrast is dominant in the shoulders of the rocking curve, requiring minor modifications in the sampling parameters for each energy. Twenty-one images were acquired for each MIR set regardless of rocking curve width, and the angular range and theta increment were reduced at higher energies to adjust for a reduction in the FWHM. FIG. 43 is a graph illustrating the contributions of absorption, incoherent scatter, and coherent scatter in breast versus energy.

Four breast specimens were selected for imaging at the NSLS. MIR images acquired at 18 keV and 25 keV were acquired over a range of −5 to 5 microradians from the peak, sampled every 0.5 microradians. The sampling range was decreased for MIR imaging at 30 keV and 40 keV to ±4 microradians, with a theta increment of 0.4 microradians. An angular range of ±3 microradians was used at 50 keV with a theta increment of 0.3 microradians, and an angular range of ±2 microradians with a theta increment of 0.2 microradians for MIR imaging at 60 keV. Corresponding synchrotron radiographs were acquired at each energy and dose. In addition, breast specimens were imaged using a General Electric Senographe 2000D (available from General Electric Company of Fairfield, Conn.). The dose used for a single image at each energy was measured using thermolumiscent detectors to determine the mean glandular dose, distribution through the sample, and the flux required to generate the image.

Figure 44:
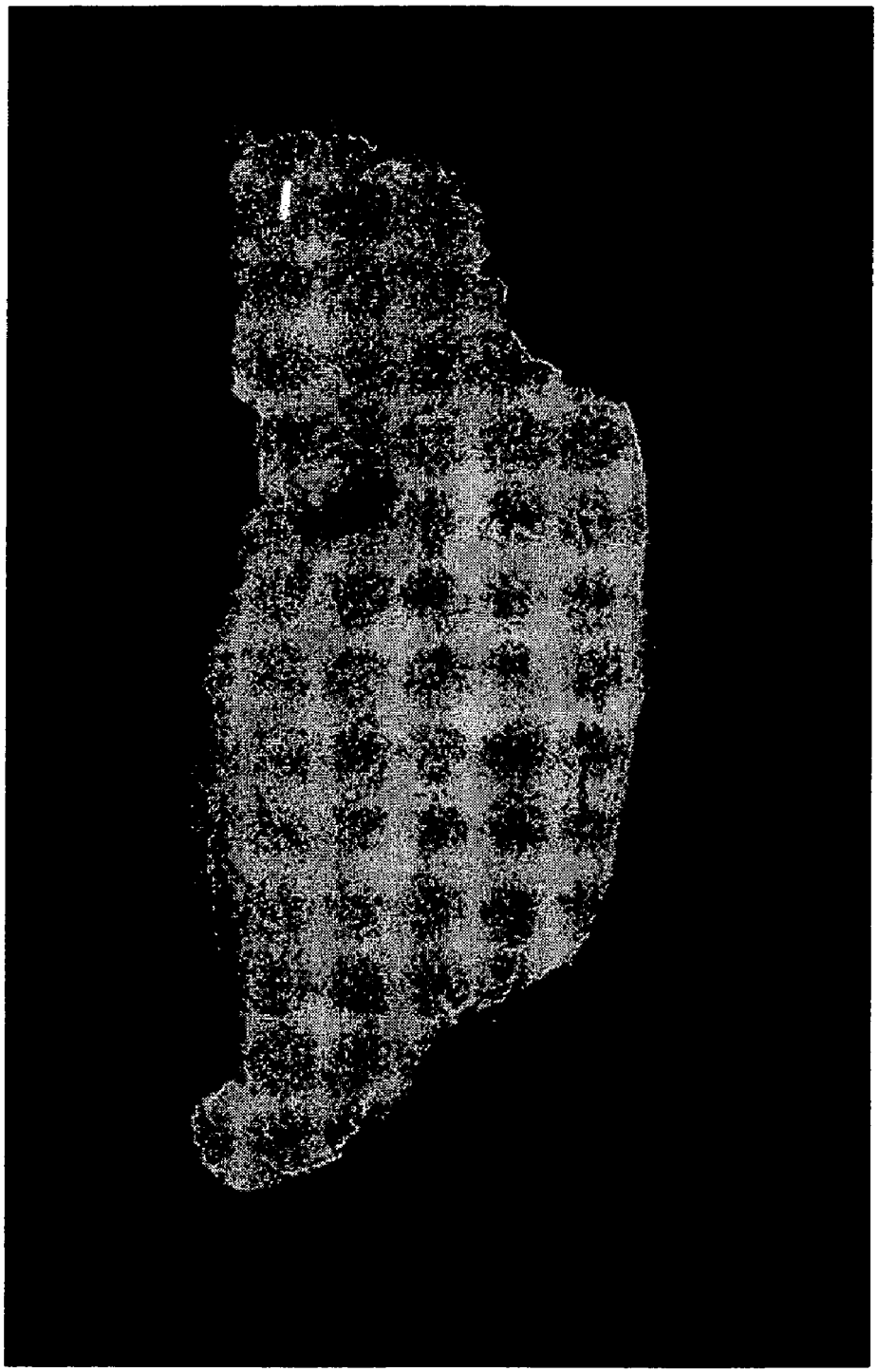
FIG. 44 is an image of an exemplary breast specimen imaged on a conventional radiography system.
Figures 45A, 45B, 45C, 45D, 45E, 45F:
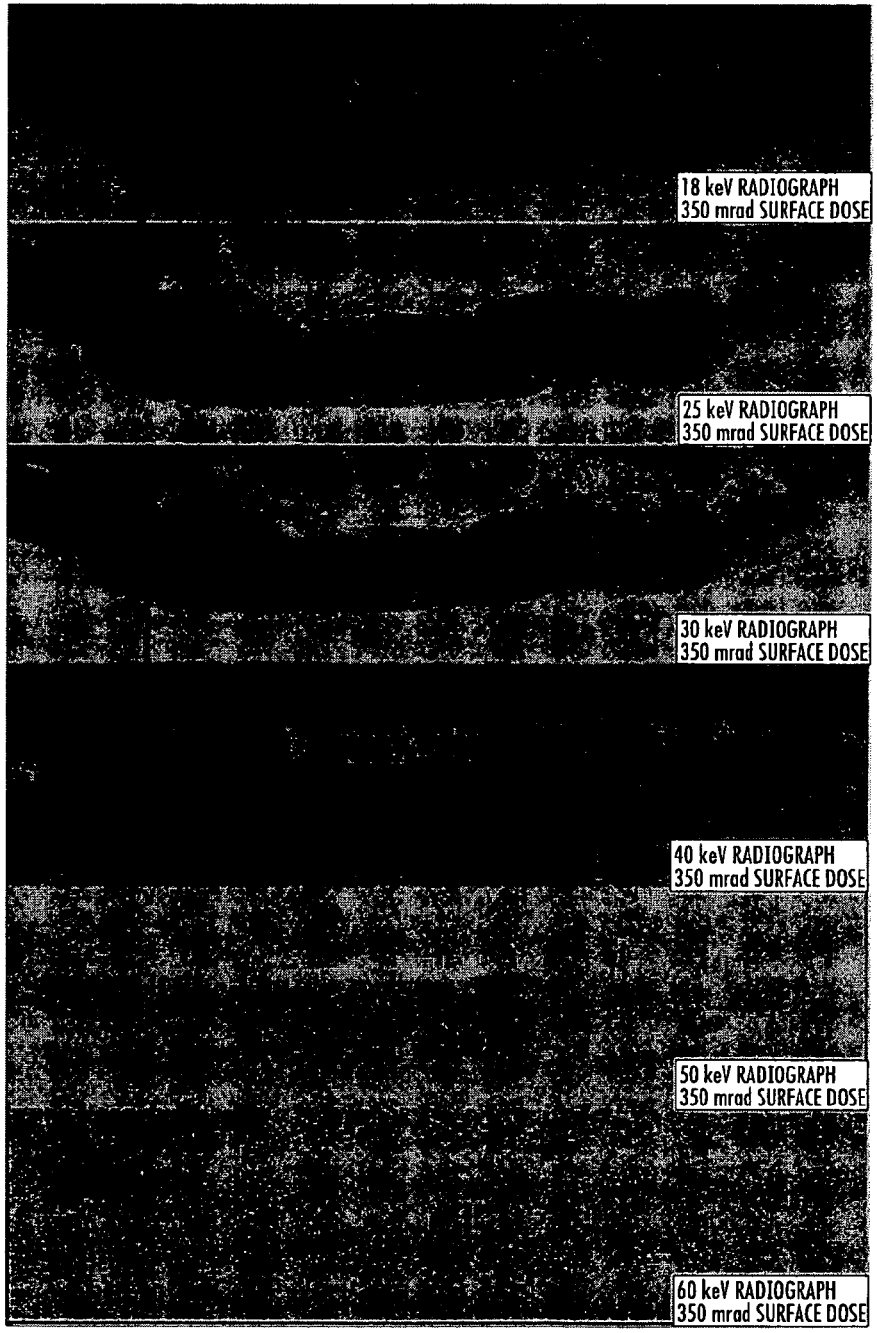
FIGS. 45A-45F are synchrotron radiographs of the same sample at beam energies of 18 keV, 25 keV, 30 keV, 40 keV, 50 keV, and 60 keV, respectively, using techniques in accordance with the subject matter described herein.

For purposes of comparison to conventional techniques, FIG. 44 is an image of an exemplary breast specimen imaged on a conventional radiography system. This specimen was imaged in air using a GE Senographe 2000D with a 100 micron pixel resolution. FIGS. 45A-45F are synchrotron radiographs of the same sample at beam energies of 18 keV, 25 keV, 30 keV, 40 keV, 50 keV, and 60 keV, respectively, using techniques in accordance with the subject matter described herein. These images were acquired in air with a level of compression comparable to that used for imaging at the NSLS.

Figure 46A:
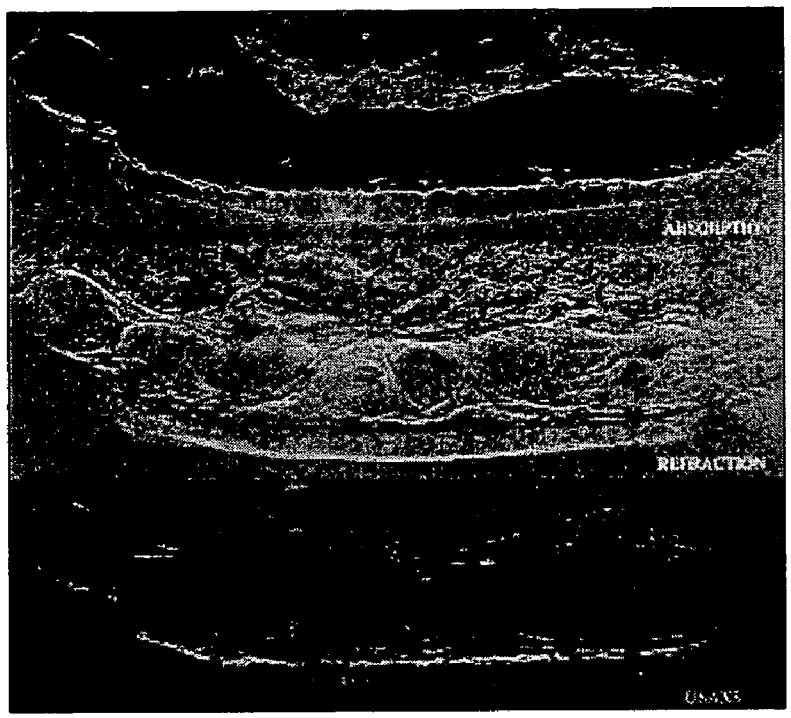
FIGS. 46A-46F are images of a breast specimen using MIR beam energies of 18 keV, 25 keV, 30 keV, 40 keV, 50 keV, and 60 keV, respectively.
Figure 46B:
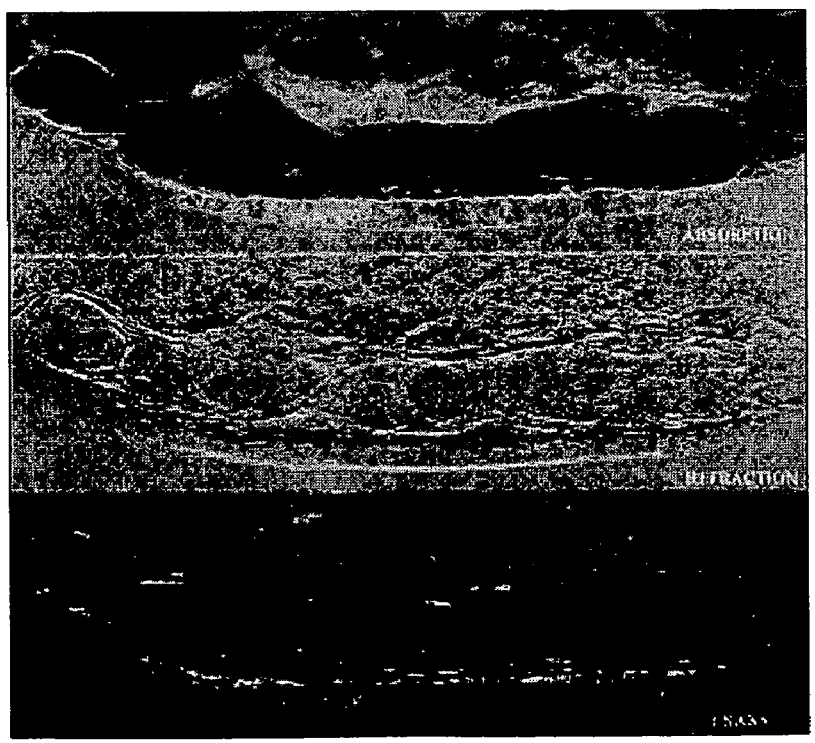
Figure 46C:
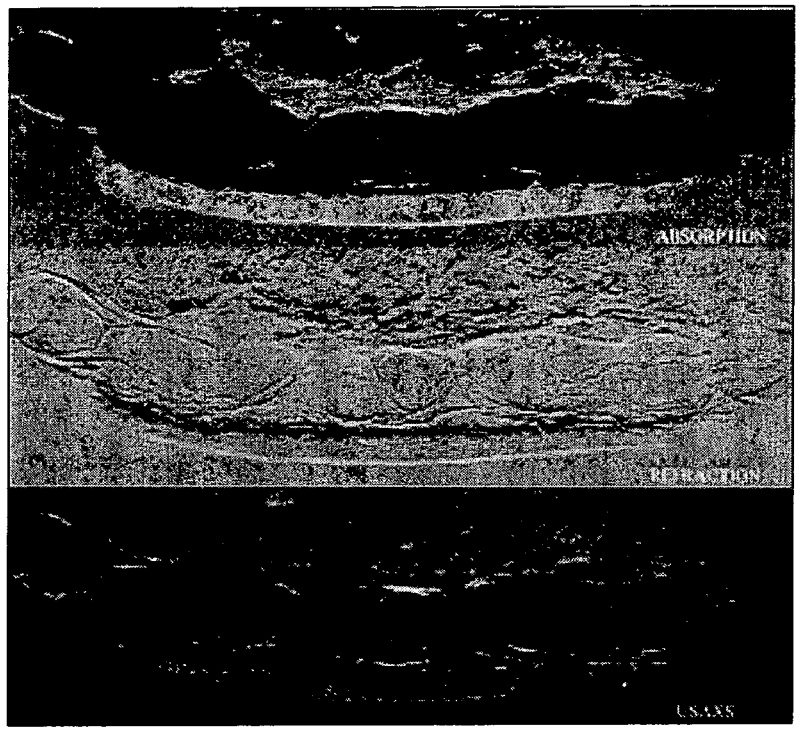
Figure 46D:
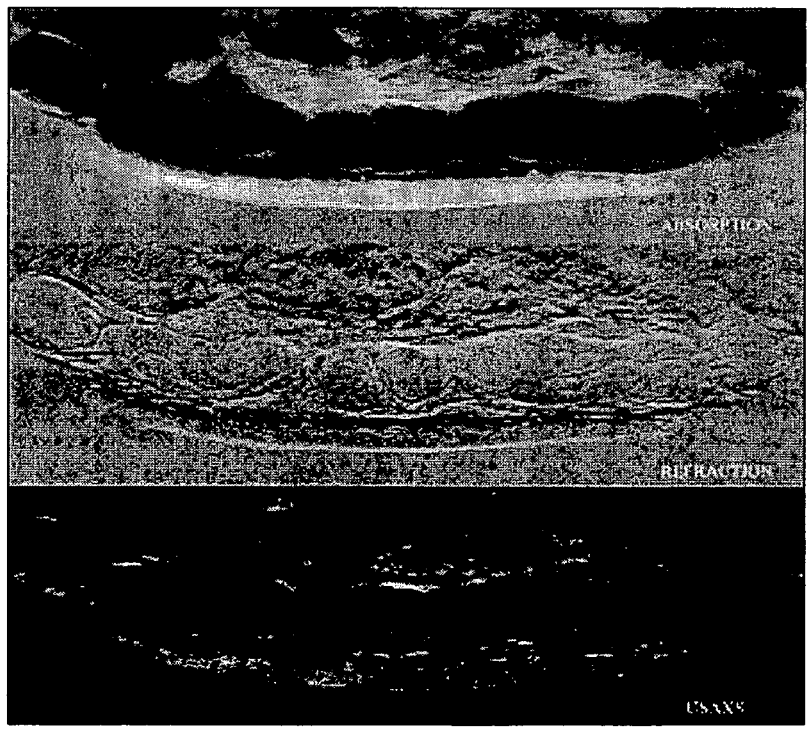
Figure 46E:
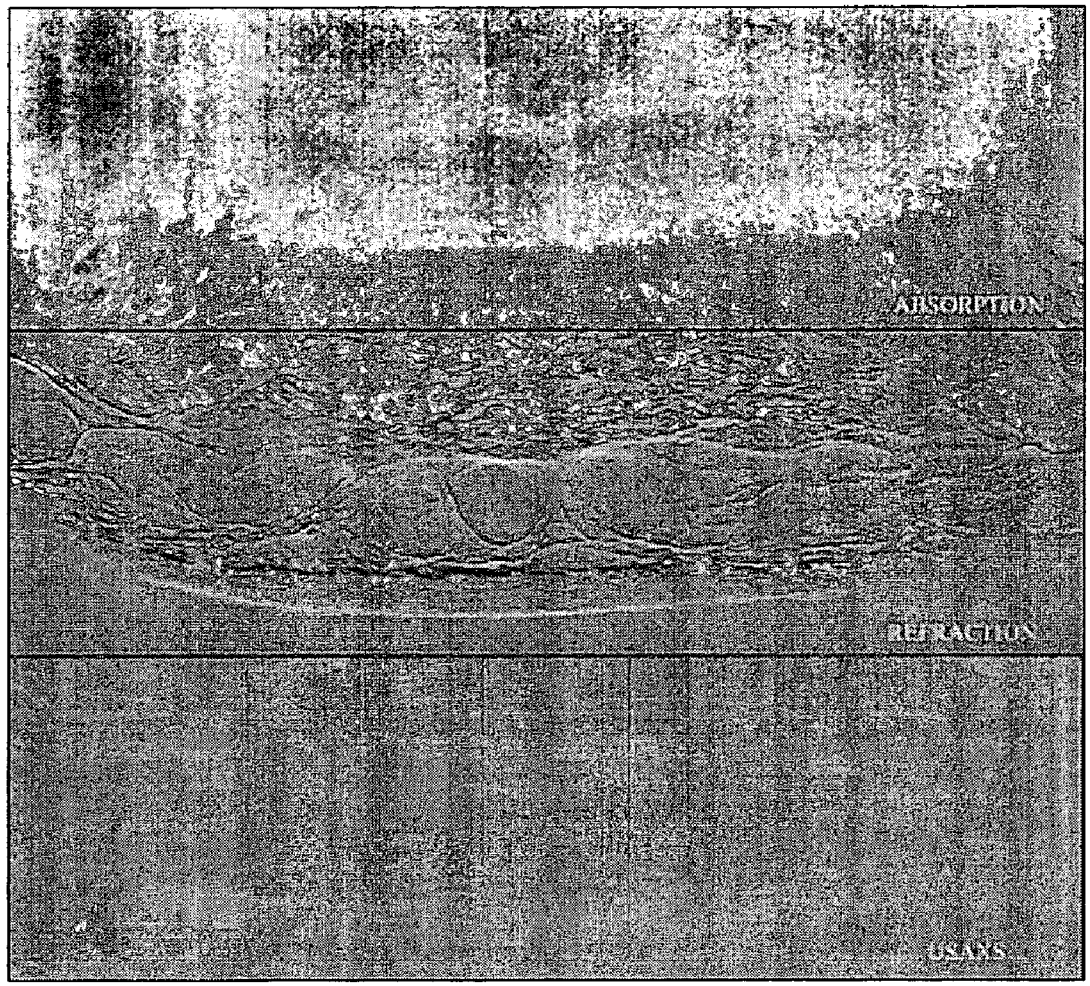
Figure 46F:
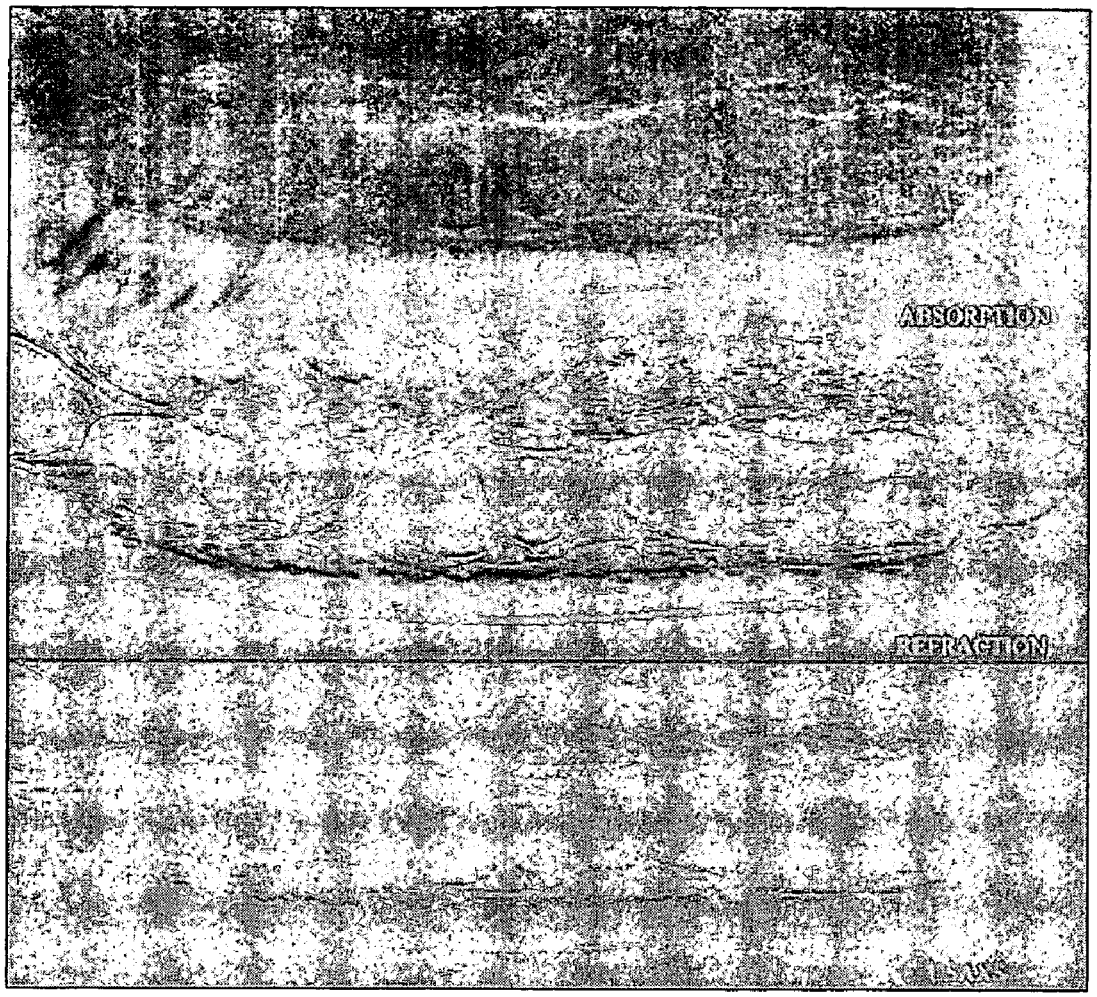
Figure 47A:
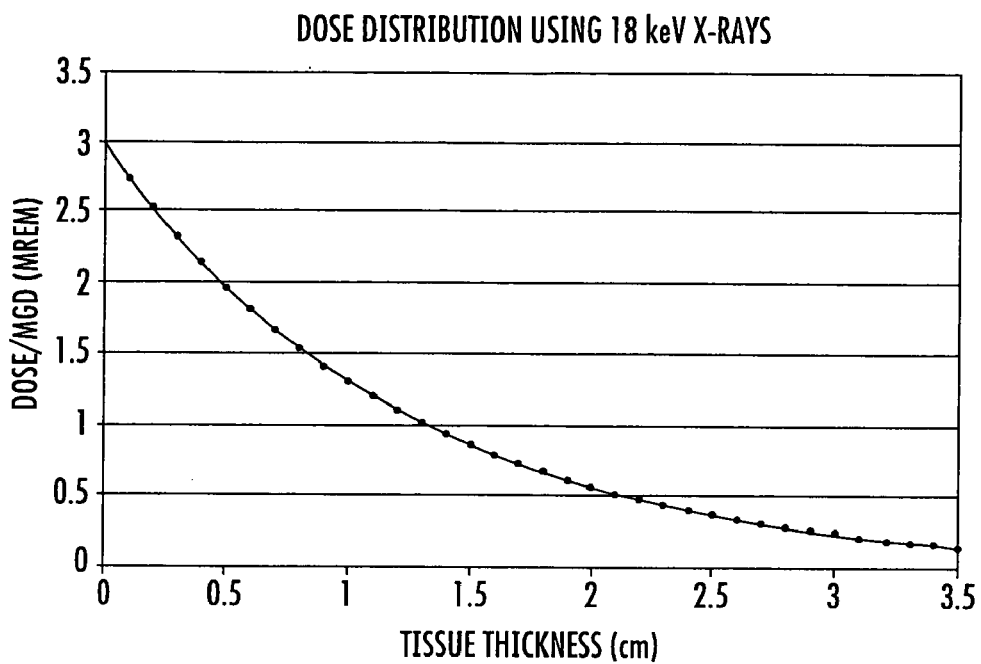
FIGS. 47A-47F are graphs of the mean glandular dose and distribution for beam energies of 18 keV, 25 keV, 30 keV, 40 keV, 50 keV, and 60 keV, respectively.
Figure 47B:
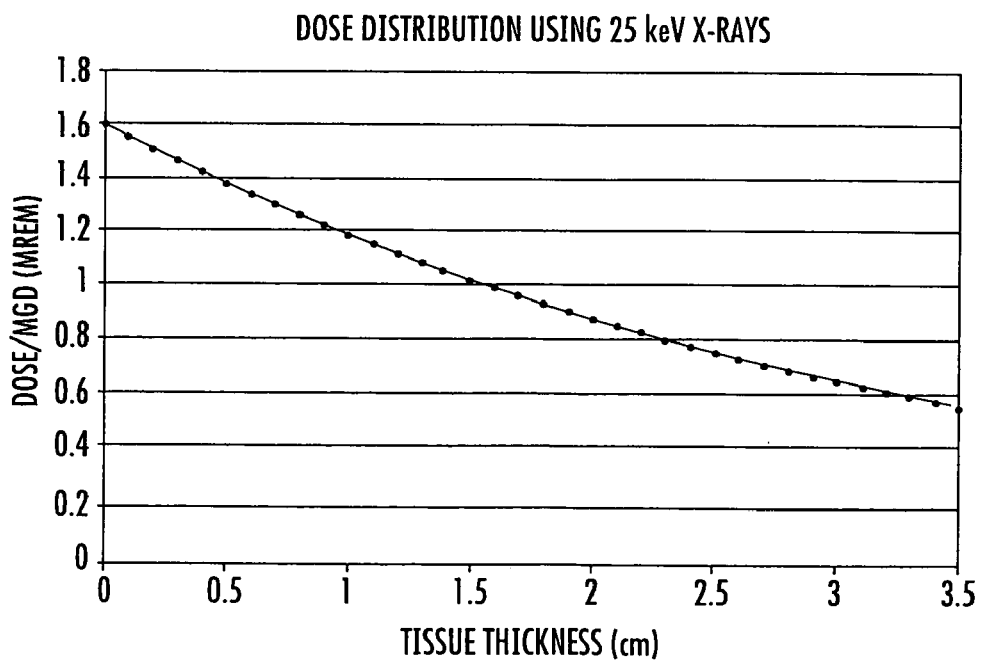
Figure 47C:
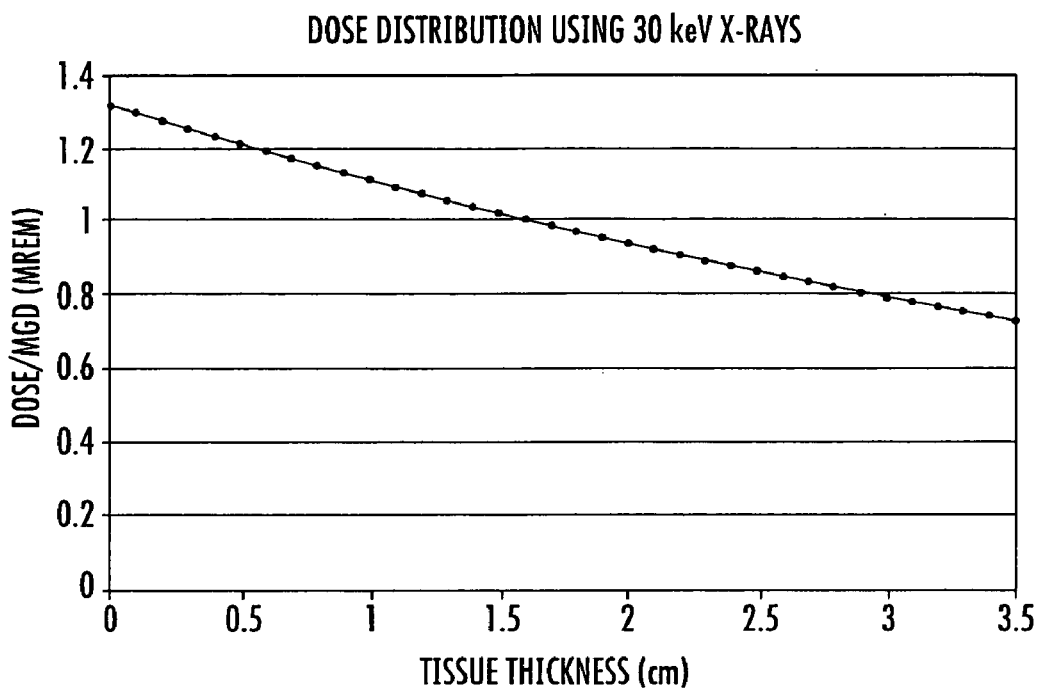
Figure 47D:
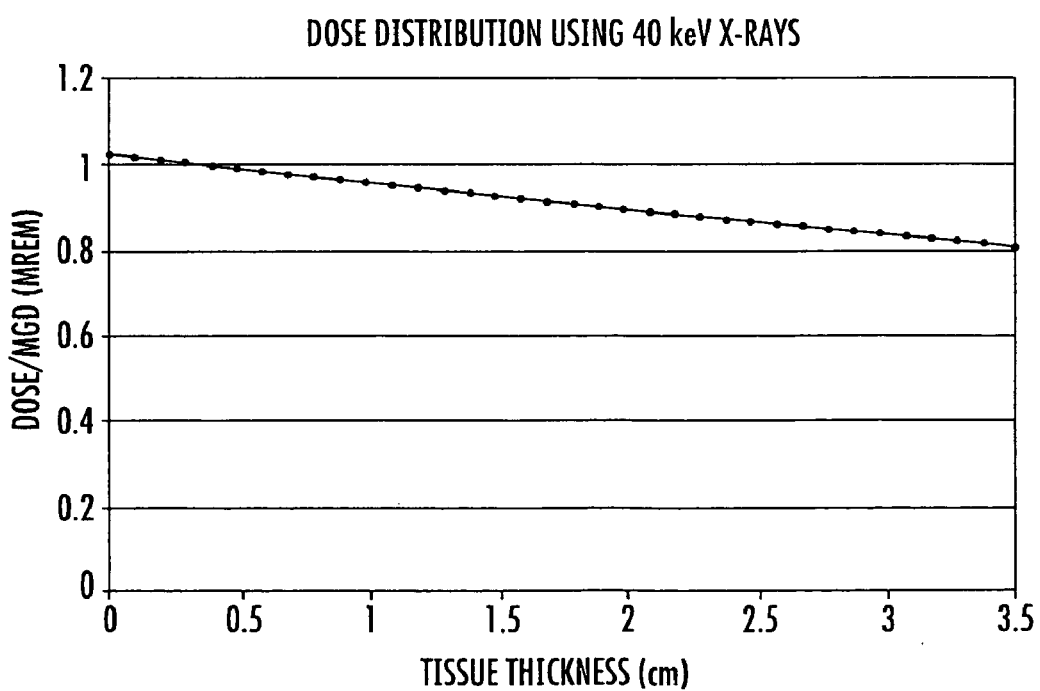
Figure 47E:
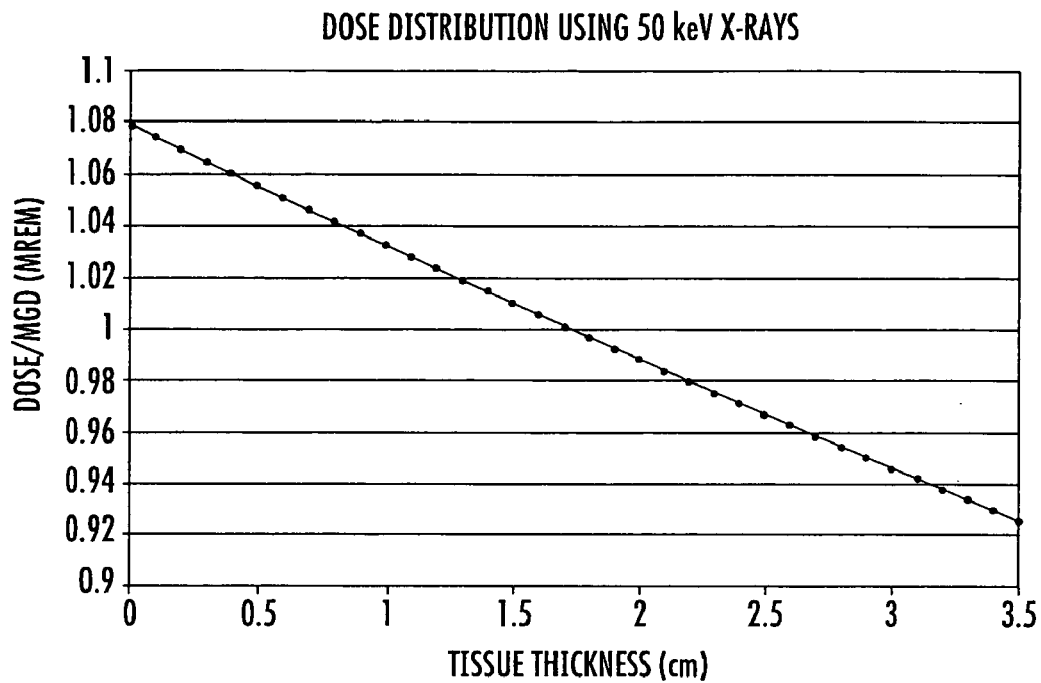
Figure 47F:
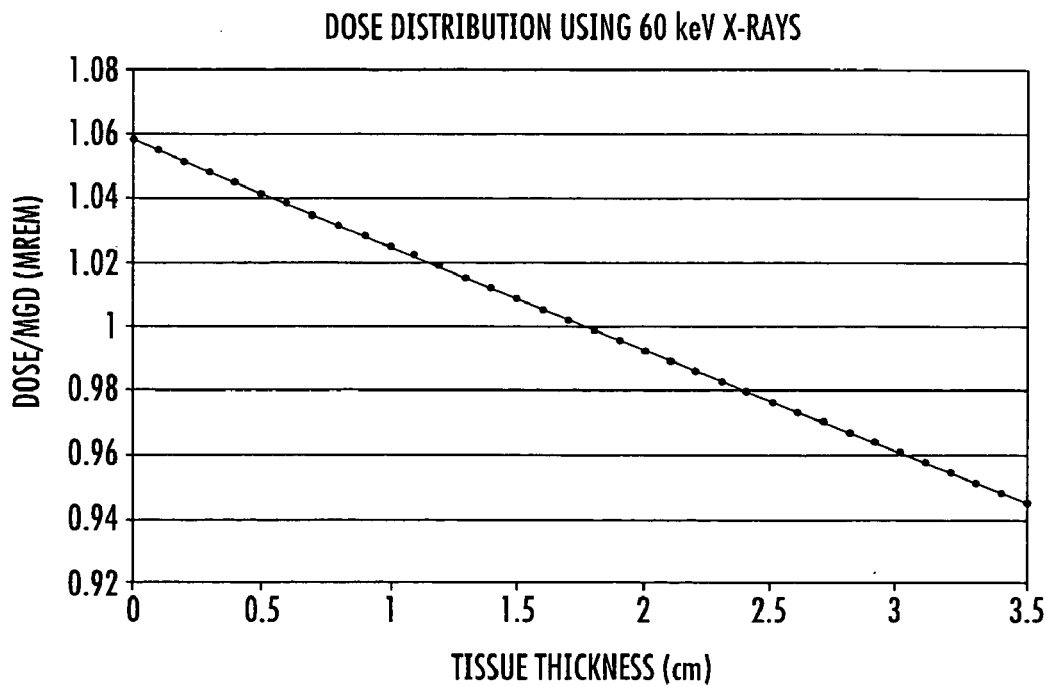

FIGS. 46A-46F are images of a breast specimen using MIR beam energies of 18 keV, 25 keV, 30 keV, 40 keV, 50 keV, and 60 keV, respectively. In particular, FIG. 46A is a breast specimen image using MIR at 18 keV with sampling parameters of ±5 microradians with a theta increment of 0.5 microradians. FIG. 46B is a breast specimen image using MIR at 25 keV with sampling parameters of ±5 microradians with a theta increment of 0.5 microradians. FIG. 46C is a breast specimen image using MIR at 30 keV with sampling parameters of ±4 microradians with a theta increment of 0.4 microradians. FIG. 46D is a breast specimen image using MIR at 40 keV with sampling parameters of ±4 microradians with a theta increment of 0.4 microradians. FIG. 46E is a breast specimen image using MIR at 50 keV with sampling parameters of ±3 microradians with a theta increment of 0.3 microradians. FIG. 46F is a breast specimen image using MIR at 60 keV with sampling parameters of ±2 microradians with a theta increment of 0.2 microradians.

The mean glandular dose and distribution was measured using thermoluminescent detectors. FIGS. 47A-47F are graphs illustrating the mean glandular dose and distribution for beam energies of 18 keV, 25 keV, 30 keV, 40 keV, 50 keV, and 60 keV, respectively.

Figure 48:
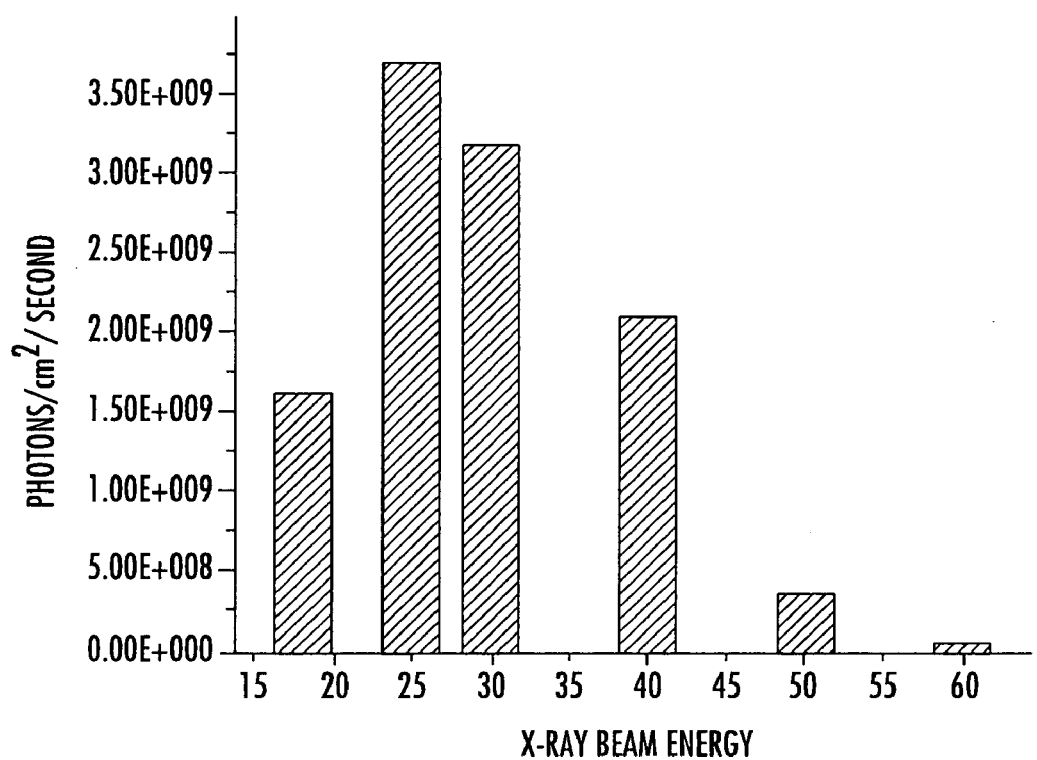
FIG. 48 is a graph of X-ray beam energy versus energy used for MIR in accordance with the subject matter described herein.

FIG. 48 is a graph illustrating X-ray beam energy versus energy used for MIR in accordance with the subject matter described herein. Using the dosimetry data obtained at each energy, the flux used for acquiring each radiograph and component of DEI sets was calculated and is presented in the figure.

The above experimentation results demonstrate how breast imaging using MIR performs across a wide range of energies. If considering absorption alone, one would expect contrast in soft tissue to fall off dramatically with an increase in energy, with little absorption contrast at energies at or above 40 keV. The synchrotron radiographs at each energy illustrate the reduction in contrast, especially at 60 keV where there is essentially zero absorption contrast in soft tissue.

Image acquisition times based conventional X-ray tubes using molybdenum sources can be as high as 10,000 seconds, well beyond the time window needed for clinical imaging. Molybdenum X-ray tubes have a stationary anode that limits heat dissipation and places significant engineering limitations on the flux that can be generated per unit time. Tungsten X-ray tubes have large, rotating anodes and can tolerate much higher voltages and amperages. While tungsten X-ray tubes offer many advantages in flux and heat dissipation, the characteristic X-rays generated by tungsten are too high to generate absorption contrast in soft tissue. However, this experiment has demonstrated that the MIR specific contrast mechanisms of refraction and scatter can generate excellent soft tissue contrast without the need for X-ray absorption.

The reduction of photons at higher energies is evident in the dose distribution curves, where there is marked difference between the distributions at 18 keV and 60 keV. At 18 keV, there is a large drop in flux due to absorption in the tissue. This drop in flux is reduced with increasing energy, with the highest transmission of photons occurring at 50 keV and 60 keV. A decrease in absorption translates to an increase in efficiency, which is evident in the flux measurements presented in FIG. 48.

In order to calibrate a fitting algorithm for the experiment, multiple nylon monofilament fibers and Lucite rods of known diameter and index of refraction were selected for analysis. The smaller nylon fibers were selected to approximate the diameter and geometry of the breast cancer spiculations. Each specimen and corresponding synchrotron radiograph were acquired using a 40 keV X-ray beam energy and a 350 mrad surface dose. For MIR an angular distribution of ±4 microradians was selected with a theta increment of 0.4 microradians, producing 21 images. These images were processed using the MIR method to generate images representing the contrast generated from X-ray absorption, refraction, and scatter.

Extracting three-dimensional information from a two-dimensional image presents a significant challenge, especially for non-uniform objects. Breast cancer spiculations are cylindrical in nature, which allows for approximations to be made regarding their material properties. In order to extract information about breast cancer spiculations, it is first necessary to design and calibrate an analysis method. A suitable MIR based analysis method can used to determine the diameter and index of refraction of both nylon and Lucite fibers and breast cancer spiculations. With these two critical properties, many other aspects of the fibers and spiculations can be analyzed and modeled. While there are three contrast components present in an MIR image, the refraction image will most likely be the most important for a clinical imaging system. If higher energy X-rays are utilized for imaging, then the absorption image will be poor when compared to the refraction image. With a major reduction in flux at the tails of the rocking curve, the scatter image will also lay a secondary role to the refraction image. Calculating and comparing the index of refraction across multiple breast cancer specimens can provide some level of assurance that the material properties generating refraction contrast is consistent and not an anomaly.

Figure 49:
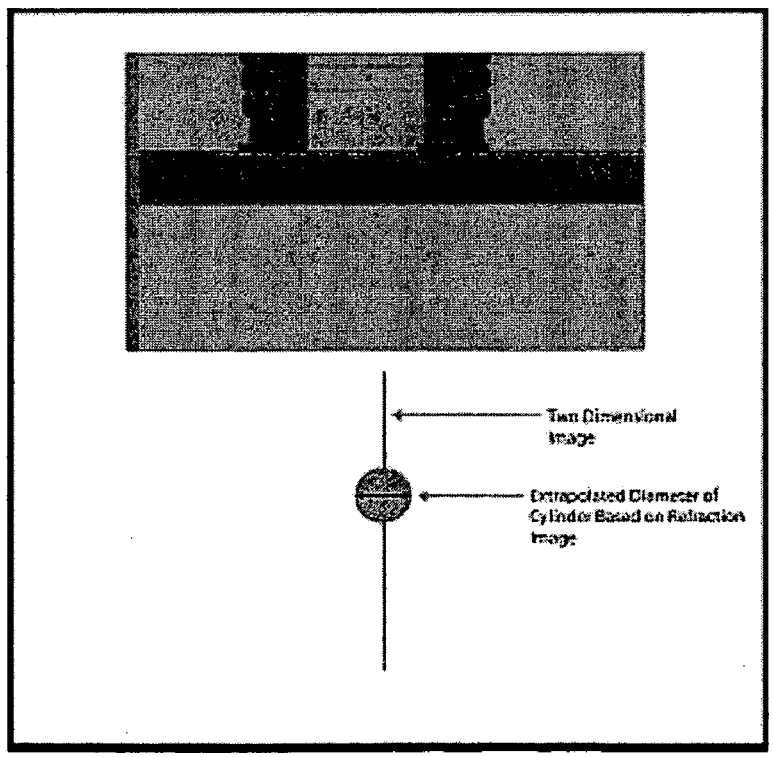
FIG. 49 is an image indicating an estimation of fiber diameter using MIR.

Calibration of the method was performed using nylon and Lucite fibers of varying diameter. Nylon fibers with diameters of 200 microns, 360 microns, and 560 microns were imaged using MIR at 40 keV with a sampling range of −4 to 4 microradians and theta increment of 0.4 microradians. These fibrils were selected to approximate the geometry and diameter of clinically significant spiculations. Larger Lucite rods with diameters of 13,000 microns and 19,000 microns were selected to assess the algorithm for larger diameter objects. FIG. 49 is an image indicating an estimation of fiber diameter using MIR. Nylon fibers are weakly absorbing, and are thus a perfect phantom material for assessing DEI and MIR contrast. The phantom in FIG. 49 was designed to measure the contrast and resolution of MIR and DEI using nylon fibrils of decreasing diameter. The smaller the diameter, the more difficult the imaging challenge.

Figure 50:
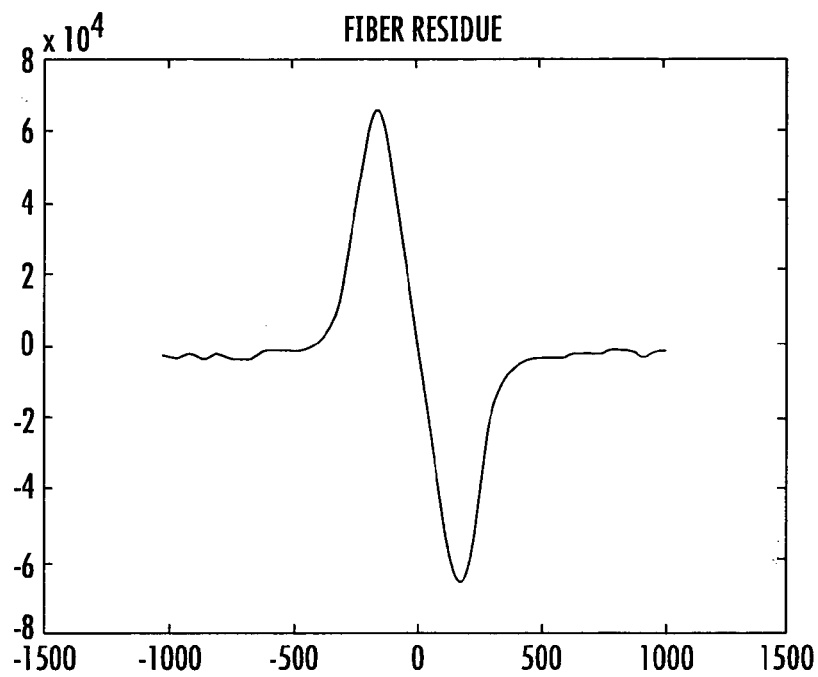
FIG. 50 is a graph illustrating nylon fiber refraction profile obtained with techniques in accordance with the subject matter described herein.

Cylindrical objects such as nylon fibers and breast cancer spiculations exhibit a characteristic refraction profile as shown in FIG. 50, which is a graph illustrating nylon fiber refraction profile. Refraction will be the highest at the edges of the rod, and zero in the middle. If the object is assumed to be cylindrical, then one can use the refraction signature from an MIR or DEI refraction image to extrapolate the diameter. With a cylinder of known diameter, the index of refraction of the fiber or fibril can be extrapolated.

Tables 7 and 8 below include nylon and Lucite diameter and index of refraction information.

TABLE 7

MIR Diameter Calibration

| Material | Energy (keV) | Measured Diameter (microns) | Calculated Diameter (microns) | Percent Error |
|---|---|---|---|---|
| Nylon | 40 | 200 | 208.96 | 4.48% |
| Nylon | 40 | 360 | 387.36 | 7.60% |
| Nylon | 40 | 560 | 617.90 | 10.30% |
| Lucite | 40 | 13000 | 14210 | 9.31% |
| Lucite | 40 | 19000 | 20938 | 10.20% |

TABLE 8

MIR Index of Refraction Calibration

| Material | Energy (keV) | Diameter (microns) | Density (g/cm$^3$) | Refractive Index | Calculated Refractive Index | Percent Error |
|---|---|---|---|---|---|---|
| Nylon | 40 | 200 | 1.14 | $1.49 \times 10^{-7}$ | $2.16 \times 10^{-7}$ | 37.3% |
| Nylon | 40 | 360 | 1.14 | $1.49 \times 10^{-7}$ | $1.89 \times 10^{-7}$ | 26.8% |
| Nylon | 40 | 560 | 1.14 | $1.49 \times 10^{-7}$ | $1.77 \times 10^{-7}$ | 18.9% |
| Lucite | 40 | 13000 | 1.19 | $1.42 \times 10^{-7}$ | $2.01 \times 10^{-7}$ | 41.5% |
| Lucite | 40 | 19000 | 1.19 | $1.42 \times 10^{-7}$ | $2.00 \times 10^{-7}$ | 39.9% |

Figure 51:
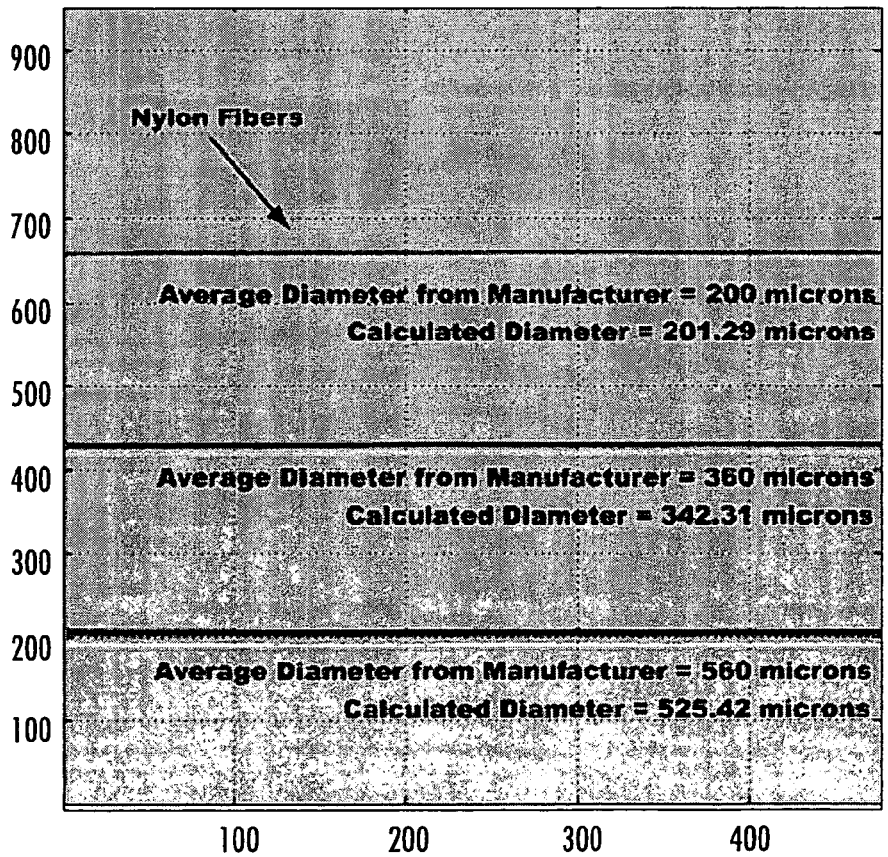
FIG. 51 are graphs of MIR refraction fitting diameter calibration.

FIG. 51 are graphs illustrating MIR refraction fitting diameter calibration. Fibrils of known dimension were imaged and an algorithm was used to calculate the index of refraction and diameter. The reasoning being that the spiculations seen in breast cancer have similar properties to nylon fibers, so the nylon phantom was used for system calibration.

Figure 52A:
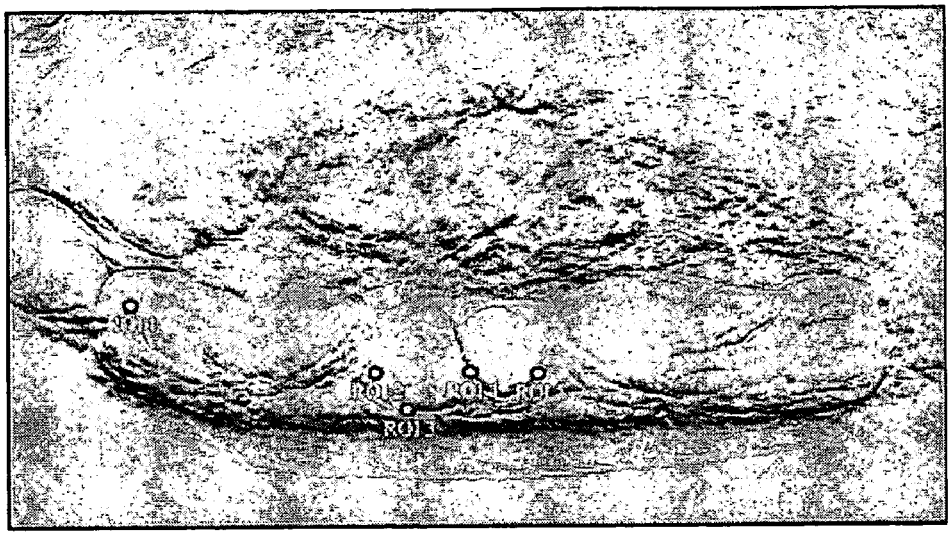
FIGS. 52A-52C are MIR refraction images of breast cancer specimens obtained with techniques in accordance with the subject matter described herein.
Figure 52B:
Figure 52C:
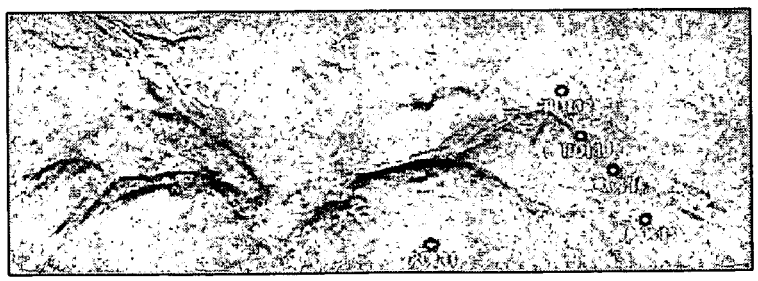

In this experiment, the same method used for extracting the diameter and index of refraction for the nylon and Lucite fibers was applied to 5 regions of interest in three separate breast cancer specimens. FIGS. 52A-52C are MIR refraction images of the breast cancer specimens. Table 9 below shows the calculated spiculation diameter and index of refraction.

TABLE 9

Fibril index of refraction

| ROI | Fibril Diameter (micrometers) | Index of Refraction |
|---|---|---|
| 1 | 125.14 | $1.91 \times 10^{-7}$ |
| 2 | 152.1 | $1.16 \times 10^{-7}$ |
| 3 | 112.24 | $2.23 \times 10^{-7}$ |
| 4 | 106.32 | $1.72 \times 10^{-7}$ |
| 5 | 121.84 | $3.64 \times 10^{-7}$ |
| 6 | 253.44 | $1.75 \times 10^{-7}$ |
| 7 | 212.1 | $2.19 \times 10^{-7}$ |
| 8 | 95.96 | $1.48 \times 10^{-7}$ |
| 9 | 178.02 | $2.71 \times 10^{-7}$ |
| 10 | 148.9 | $2.50 \times 10^{-7}$ |
| 11 | 111.5 | $1.84 \times 10^{-7}$ |
| 12 | 91.18 | $2.00 \times 10^{-7}$ |
| 13 | 104.78 | $2.14 \times 10^{-7}$ |
| 14 | 205.82 | $5.22 \times 10^{-8}$ |
| 15 | 126.8 | $1.05 \times 10^{-7}$ |

Figure 53:
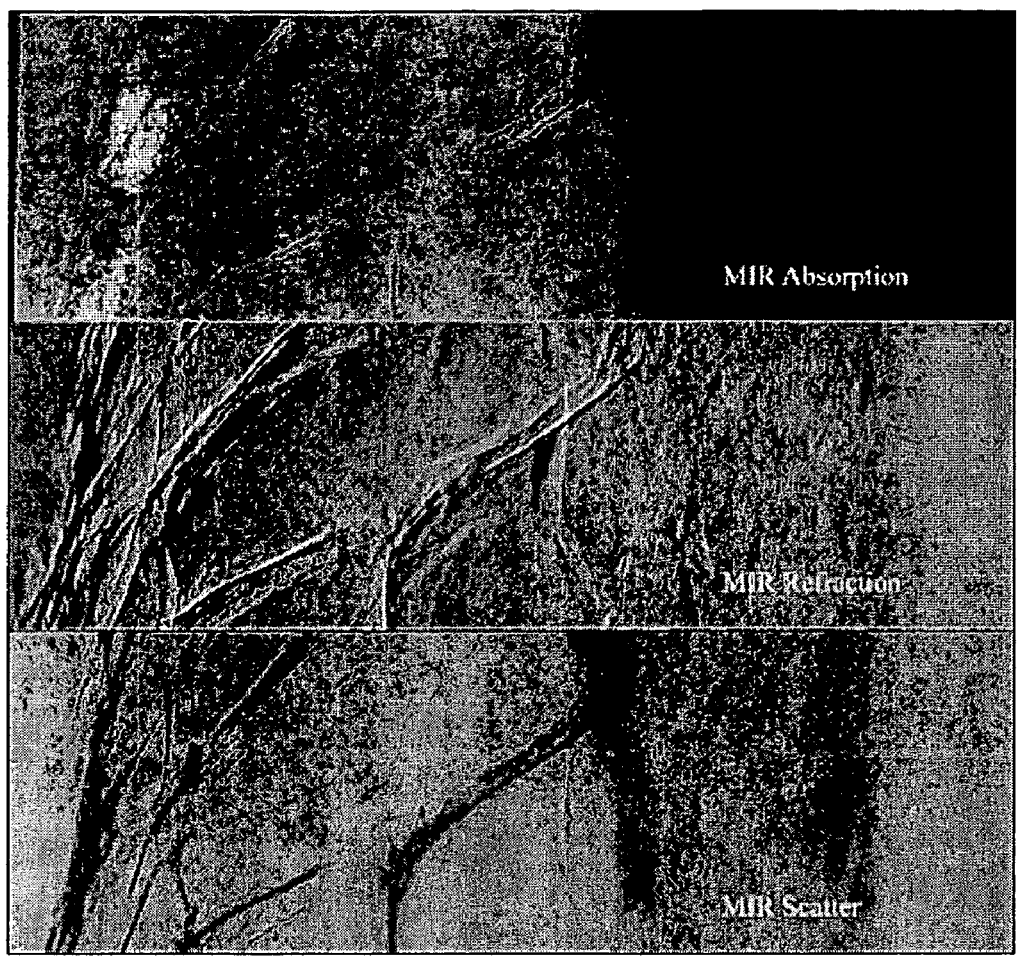
FIG. 53 is an image of an MIR set of a localized breast cancer mass and spiculation obtained by a DEI system in accordance with the subject matter described herein.

Average Index of Refraction = $1.92 \times 10^{-7}$
Standard Deviation = $7.40 \times 10^{-8}$ FIG. 53 is an image of an MIR set of a localized breast cancer mass and spiculation obtained by a DEI system in accordance with the subject matter described herein.

FIGS. 54A-54E are images illustrating the visualization of fibrils with DEI as compared to a conventional radiograph. In particular, FIG. 54A is an image of a conventional radiograph of a breast tissue specimen that contains invasive lobular carcinoma. The sample has undergone histologic evaluation to confirm that the fibrils in the 1-cm white box correspond to fingers of tumor extending from the surface of the tumor. FIG. 54B is a conventional radiograph image illustrating an expanded view of the region designated by the 1-cm white box in FIG. 54A. FIGS. 54C-54E are DEI images illustrating an expanded view of the region designated by the 1-cm white box in FIG. 54A. In these expanded views, it is evident that tissue contrast is higher in the DEI images than in a conventional radiograph, where the structures of interest are barely visible.

To quantify the improved contrast of DEI, contrast measures of the fibrils were computed along the image profiles shown as vertical white lines in FIGS. 54B-54E. The computation was repeated for other regions of the tissue sample. A statistical analysis showed that the DEI refraction image had 8-14 times more contrast than a conventional radiograph, while the peak image had 12-33 times more contrast than a radiograph.

The underlying physics of X-ray refraction and scatter imaging is still in an early stage of investigation, especially when compared to the 100 plus year history of absorption based X-ray imaging. Given the inherent inhomogeneity of biological tissues, an analysis of the roughly cylindrical breast cancer spiculations provides a diagnostically useful feature than can be reliably compared with multiple tissue specimens.

The use of multiple standardized homogenous cylinders imaged in air allows for an accurate calibration of the refraction based fitting algorithm. Use of this algorithm for analyzing biological tissues can introduce errors into the calculation due to the non-homogenous nature of biological tissues, but the properties of breast tissue and the diagnostic application reduce the importance of these errors in the absolute calculation.

The fundamental problem with conventional mammography is the difficulty in visualizing low contrast objects immersed in highly absorbing background of adipose tissue. Neoplastic lesions increase in size and density with time, eventually becoming large and dense enough to rise above the background and become visible using conventional methods. Since breast cancer mortality is directly related to the size and progression of a lesion, reducing the time between the generation of a malignant lesion and detection is a goal of all new breast imaging modalities.

DEI and MIR improves upon conventional radiography by utilizing the differences in multiple X-ray contrast mechanisms to help differentiate between benign and malignant structures. Adipose tissue may have an X-ray attenuation similar to a small malignant lesion, but they do not have the same refraction signatures. Adipose tissue has very little refraction and scatter contrast, but the small cylindrical spiculations of a breast cancer lesion has a large refraction and scatter signatures. At 40 keV, absorption contrast in soft tissue is minimal, further increasing the overall contrast gradient between the lesion of interest and the background tissue.

Further gains in refraction contrast for spiculations come from their geometry, which is ideal for the refraction of X-rays. For a collimated X-ray beam incident on a cylindrical object, refraction contrast will be the greatest at the top and bottom of the cylinder, with minimal refraction contrast at the center. As the diameter of a cylinder decreases, refraction contrast can remain due to the geometry of the object even after the level of absorption contrast fades into the background. The index of refraction values obtained across multiple breast cancer specimens indicates that the materials properties are similar, and the increase in contrast should be observed in most similar cancer specimens.

Determining the underlying contrast mechanisms providing enhanced visualization in breast tissue is a paramount step in designing a non-synchrotron based DEI/MIR system. This study demonstrates that the MIR specific contrast mechanisms of refraction and scatter play a major role in structural visualization, further reducing the dependence on X-ray absorption for lesion visualization. A reduction in X-ray absorption translates to a reduction in patient absorbed dose, which is of tremendous benefit when considering the relatively high dose required for conventional mammography.

The use of nylon in these experiments indicates a potential use for future modeling and simulation experiments. With a similar geometry, diameter, and index of refraction, nylon monofilament can provide insight into why these diagnostically important structures generate high contrast.

Computer Simulations

Computer simulation software was developed for the purpose of testing DEI designs. The developed software uses optical ray tracing to calculate patient dose and track X-ray fluence through a DEI system, based on a specified arrangement and specification of the source, crystals, object, and detector. Because the crystal optics reject X-rays traveling in undesired directions, the main feasibility hurdle DEI is to obtain sufficient numbers of photons surviving to reach the detector plane.

A list of the system parameter specifications and results of a simulation for one design is provided in Tables 10 and 11, respectively, below.

TABLE 10

System Parameter Specifications

| | |
|---|---|
| Pixel Size | 50 µm × 50 µm |
| Source to Pre-Mono | 15 cm |
| Source to Object | 83 cm |
| Source to Detector | 100 cm |
| Si (4, 4, 0) Bragg Angle | 6.25 degree |
| Min Crystal Length | 9.2 cm |
| Min Take-Off Angle | 1 degree |
| Electron Spot Size | 12 mm × 0.8 mm |
| Est Flux from W Target | 435 $K_{\alpha 1}$ photons/mA-s @ 150 kVp |
| Charge Required | 120 mA-sec |
| Energy Required | 400 mA @ 150 kVp |
| Image Size | 20 cm × 25 cm |
| Imaging Time | 6 seconds |

TABLE 11

System Parameter Results

| 5 cm Breast Compression | |
|---|---|
| Fluence at Detector | 564 photons/pixel |
| Mean Glandular Dose | 0.004 mGy* |
| 10 cm Breast Compression | |
| Fluence at Detector | 200 photons/pixel |
| Mean Glandular Dose | 0.012 mGy* |

Figure 55A:
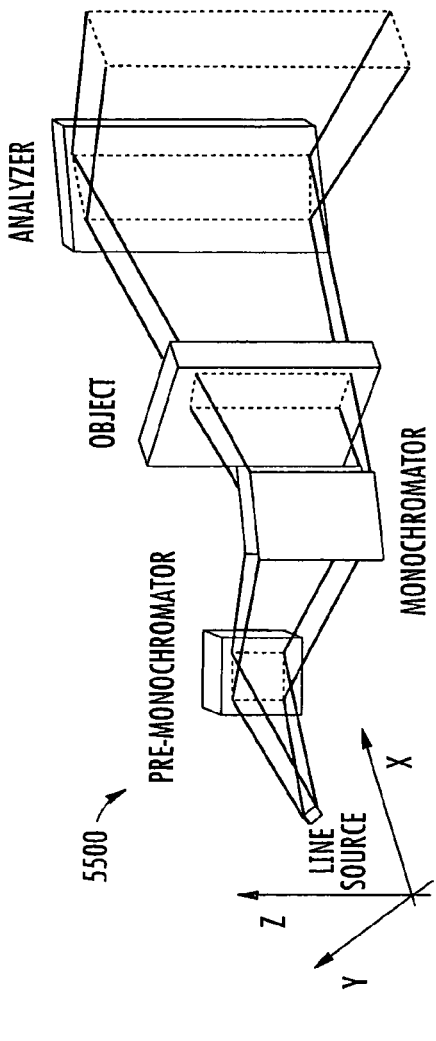
FIGS. 55A-55C are schematic diagrams of a DEI system simulated using the computer simulation software according to an embodiment of the subject matter described herein.
Figure 55B:
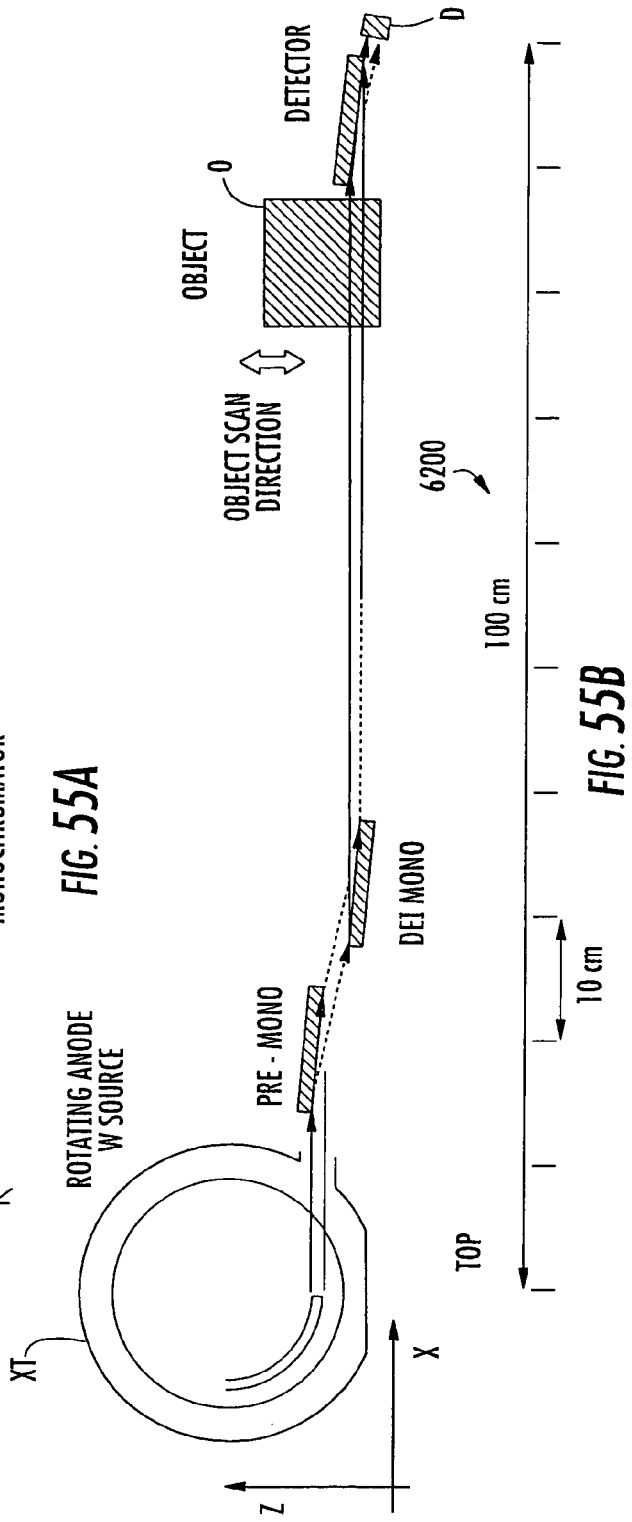
Figure 55C:
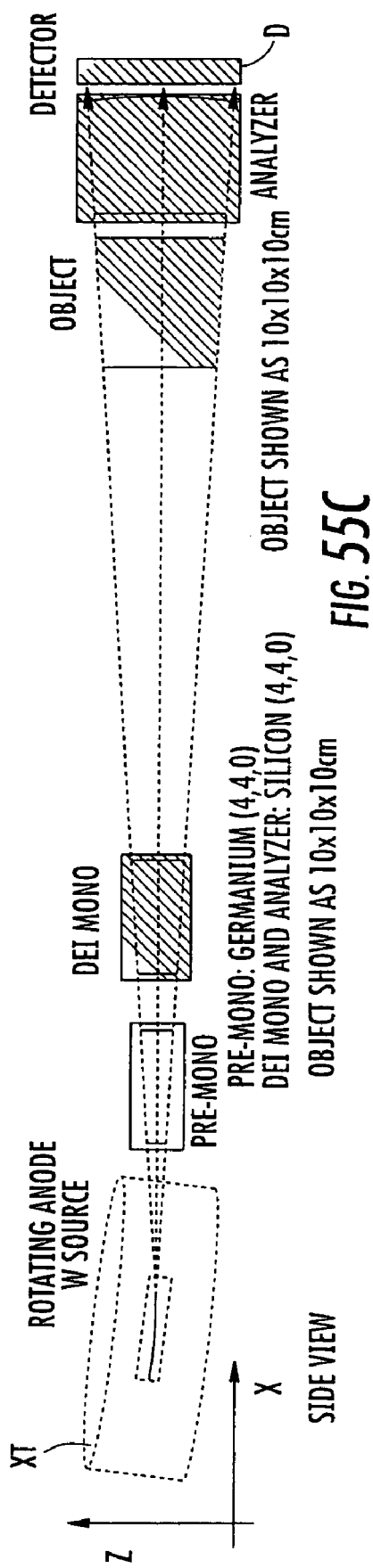

*Worst-case estimate, which assumes that all attenuation leads to energy deposition in tissue FIGS. 55A-55C are schematic diagrams of a DEI system, generally designated 5500, simulated using the computer simulation software according to an embodiment of the subject matter described herein. In particular, FIGS. 55A-55C are a perspective view, a side view, and a top view of the DEI system. Referring to FIGS. 55A-55C, X-ray beams are generated by an X-ray tube XT having a line source. In one simulation, X-ray tube XT was simulated as a Siemens DURA® Akron B X-ray tube (available from Siemens Medical Solutions USA, Inc. of Malvern, Pa.). The Siemens X-ray tube includes a tungsten target, thus it produces $K\alpha 1$ X-rays at 59.3 keV. Therefore, X-ray tube XT was simulated to produce $K\alpha 1$ X-rays at 59.3 keV. A powerful tube may be needed for DEI to achieve the flux needed to overcome the losses in the crystal optics system before the beam strikes the patient. The Siemens X-ray tube has a rotating anode which dissipates heat, and permits the tube to run at high power (60 kW). The simulated DEI system uses a line-source port on the tube.

Figure 56:
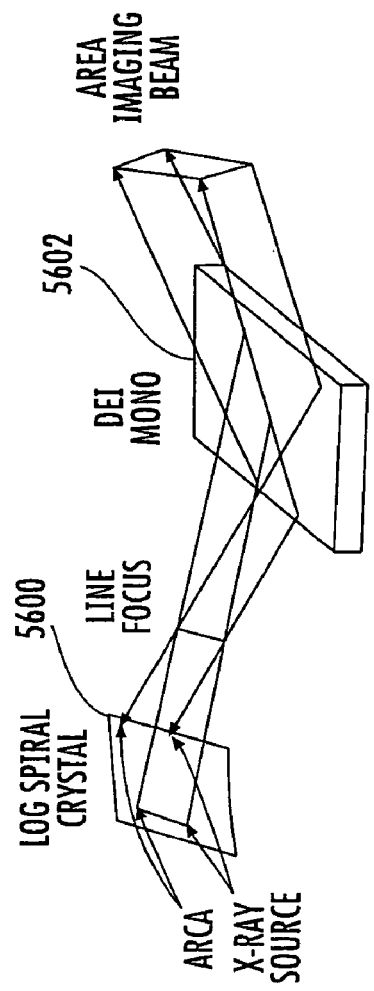
FIG. 56 is a perspective view of a log-spiral focusing element coupled to a DEI monochromator crystal according to an embodiment of the subject matter described herein.

FIG. 56 is a perspective view of a log-spiral focusing element 5600 coupled to a DEI monochromator crystal 5602 according to an embodiment of the subject matter described herein. Referring to FIG. 56, element 5600 can be a bent diffraction crystal configured to boost photon flux. Element 5600 provides a large target area for the X-ray source, which can achieve high power, and focus the emitted radiation to form a thin, virtual line source. The virtual line source can be small and very bright. Further, the bent diffraction crystal 5600 has a surface which is a portion of a logarithmic spiral.

FIG. 57 is a perspective view illustrating the focusing effect of a log-spiral element, with a source at caustic. The surface shape makes the Bragg-diffracting element behave as a focusing device. The log-spiral element has the following properties: (1) it collects light emitted from a large target area at a fixed take-off angle where brightness is at a maximum; (2) it monochromates the beam; and (3) it focuses the radiation to form a high-brightness, virtual line source. FIGS. 58A and 58B are a plan view and an elevation view, respectively, of a characterization system for experimental studies. Referring to FIGS. 58A and 58B, the figures illustrate the log spiral element focusing the radiation to form a high-brightness, virtual line source.

DEI system 5500 includes three crystals: a pre-monochromator, a monochromator, and an analyzer. All three crystals are silicon and are tuned for the [440] reflection order. Large crystals can be made by slicing along this direction. Such crystals are readily available.

The scan protocol in the simulation of DEI system 5500 was set to six seconds for a detector D. In one example, detector D can be a single line device that is read out once per image line. In another example, detector D can be a full-field device that is scanned in synchrony with the motion of an object O across the X-ray beam. In either a single line detector or a full-field detector, one line or strip of image data is acquired at a time.

Figure 59:
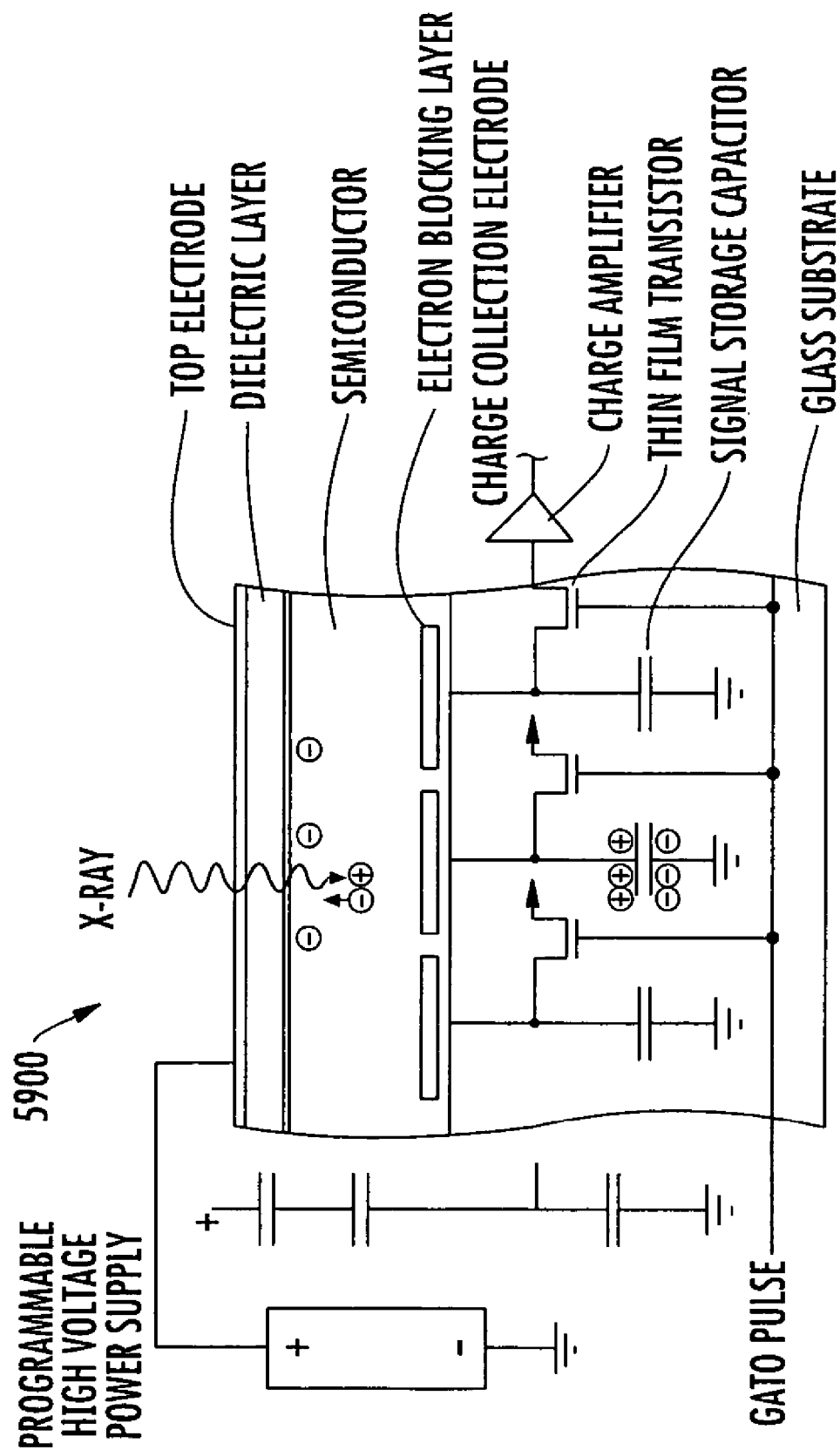
FIG. 59 is a schematic diagram of a direct X-ray-to-charge conversion detector.

In another example, detector D may be a direct X-ray-to-charge conversion detector, which allows the use of thick absorbers to achieve efficiency at higher energies without significant loss of spatial resolution. FIG. 59 is a schematic diagram of a direct X-ray-to-charge conversion detector, generally designated 5900. Detector 5900 can provide good spatial resolution and stopping power at high X-ray energy, such as that produced by a tungsten X-ray tube. Detector materials with higher Z and density could be employed such as CZT, $IbI_2$, or $HgI_2$ to improve high energy performance.

Simulation results indicated that fluence at the detector is about 600 photons per pixel, which is about ⅓ to ⅑ that of a conventional mammogram. Thus, the simulation results indicate that the noise level of the simulated MIR system would be approximately 1.7 to 3 times greater than in a conventional mammogram. However, at low noise levels, the refraction contrast can be 8-33 times higher than in a conventional mammogram.

Further, for the simulated DEI system, the mean glandular dose is about 0.004 mGy, which is about 250-750 times lower than in a conventional mammogram at 5 cm compression. At 10 cm compression, absorbed dose in MIR would be 0.019 mGy, which is thousands of times lower than that obtained in a conventional mammogram at the same compression.

Exemplary Imaging Results

Figure 60A:
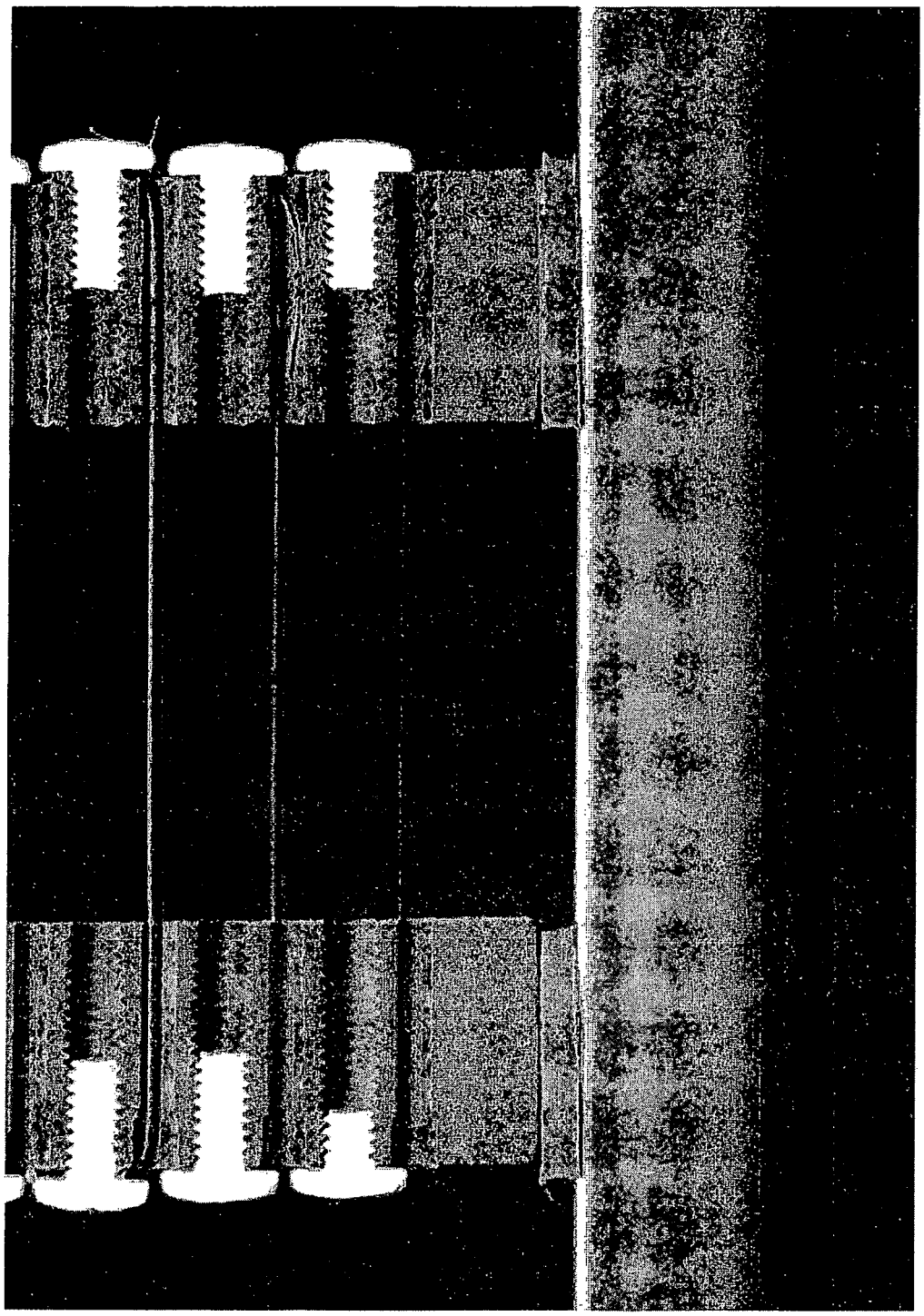
FIGS. 60A and 60B are images produced of the same nylon fibril phantom by a synchrotron-based system and an X-ray tube-based system, respectively, in accordance with the subject matter described herein.
Figure 60B:
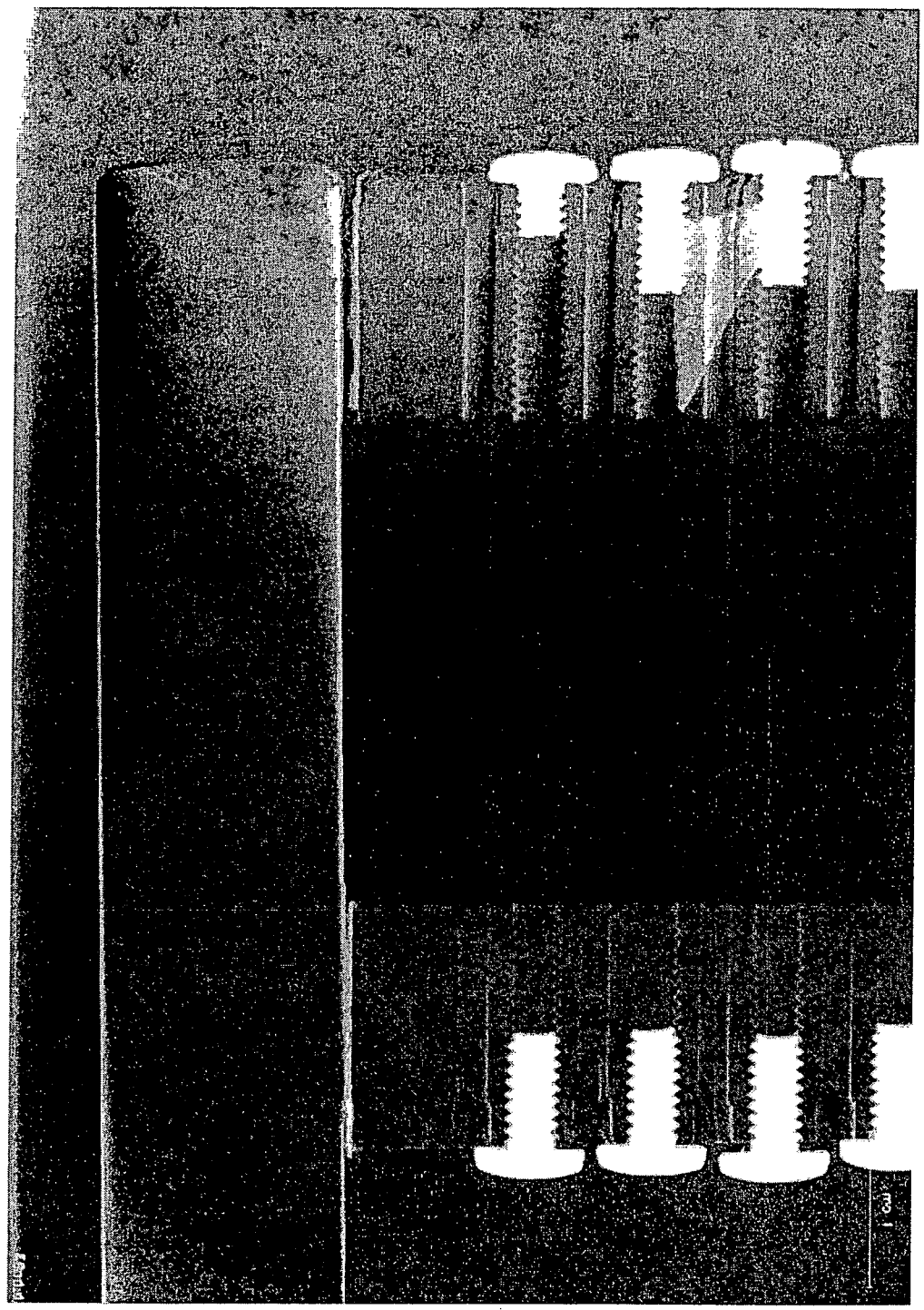

As set forth above, synchrotrons and X-ray tubes are two suitable types of X-ray sources for producing DEI images in accordance with the subject matter described herein. For comparison purposes, FIGS. 60A and 60B are images produced of the same nylon fibril phantom by a synchrotron-based system and an X-ray tube-based system, respectively, in accordance with the subject matter described herein. The image of FIG. 60A was produced by a synchrotron-generated, X-ray beam at 60 keV and acquired at an analyzer rocking curve position of +0.4 microradians with a dose of 4.0 mrad. The image of FIG. 60B was produced at an analyzer rocking curve position of +0.4 microradians with a dose of 0.4 mrad and tube settings of 160 kV and 6.2 mA. The imaged nylon fibers have diameters of 560 microns (top fiber), 360 microns (middle fiber), and 200 microns (bottom fiber).

Nylon fibers are very weakly absorbing, thus these images show an example of the advantage of using refraction imaging for viewing such weak absorbing materials. In particular, for example, it is important to note that these results indicate that images of soft tissue can be obtained with an X-ray tube using a voltage of 160 kV in accordance with the subject matter described herein.

Figure 61:
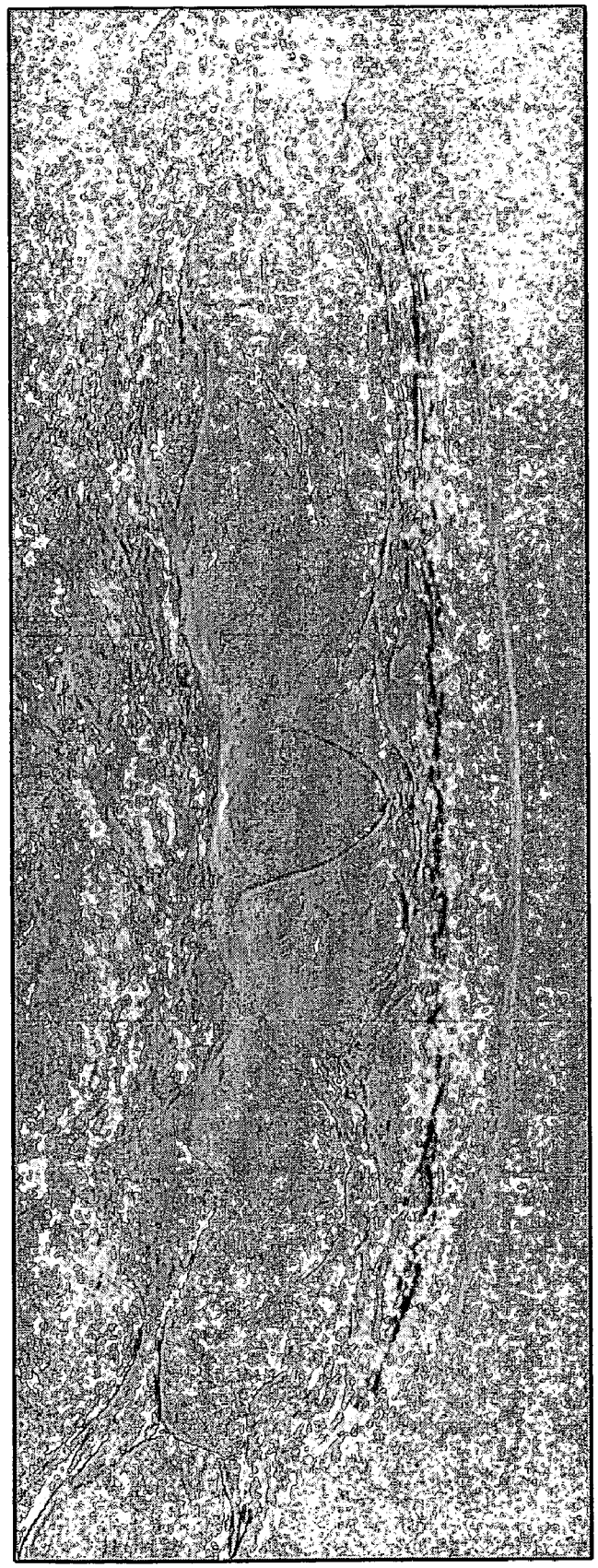
FIG. 61 is a synchrotron refraction image of the same breast specimen shown in FIGS. 44 and 45A-45F using techniques in accordance with the subject matter described herein.

FIG. 61 is a synchrotron refraction image of the same breast specimen shown in FIGS. 44 and 45A-45F using techniques in accordance with the subject matter described herein. In this example, the beam energy was 60 keV with a dose of 4 mrad.

Figure 62A:
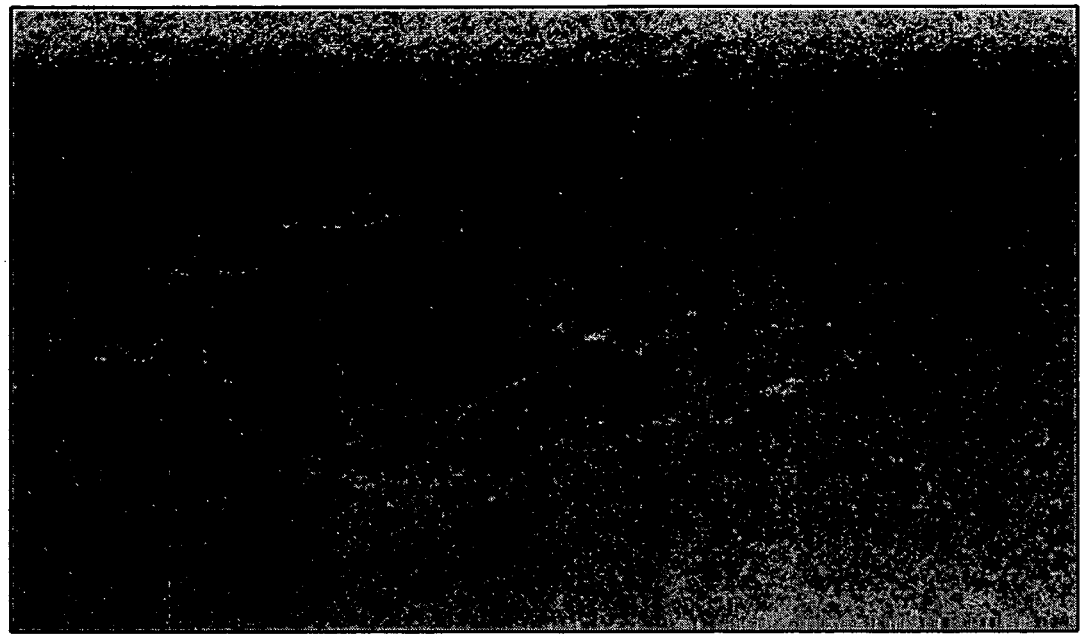
FIGS. 62A and 62B are images of the same area of a breast tissue specimen obtained using an X-ray tube and a synchrotron, respectively, in accordance with the subject matter described herein.
Figure 62B:
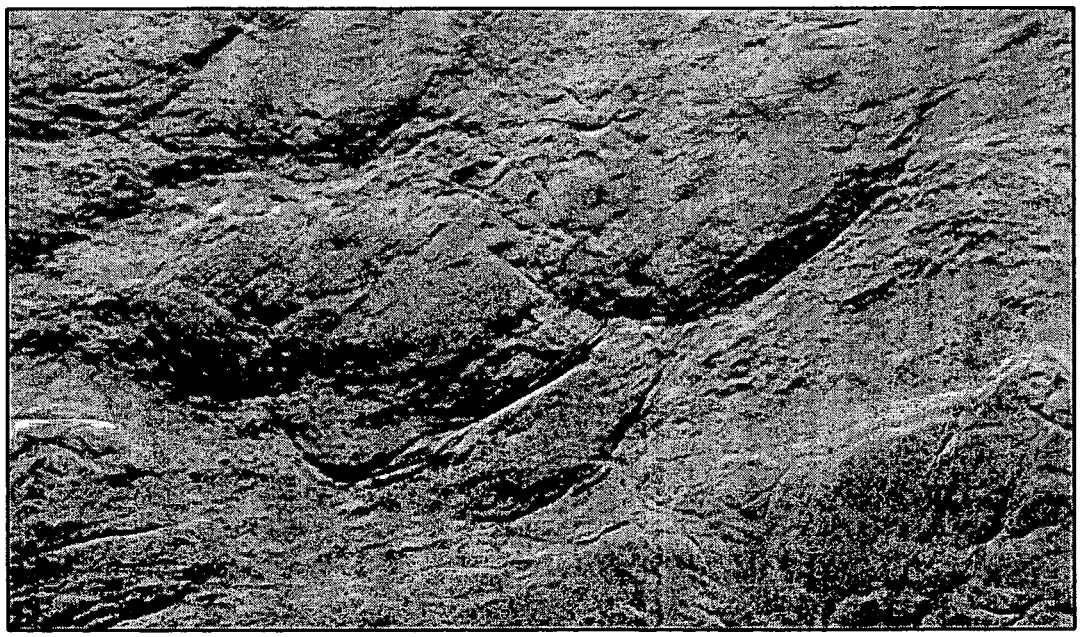

For purposes of comparison, FIGS. 62A and 62B are images of the same area of a breast tissue specimen obtained using an X-ray tube and a synchrotron, respectively, in accordance with the subject matter described herein. The image shown in FIG. 62A was acquired using an X-ray tube with a dose of 0.4 mrad. The image shown in FIG. 62B was acquired using a 40 keV synchrotron at an analyzer position of +0.4 microradians and a dose of 350 mrad. The breast tissue specimen was immersed in 4.5 cm of water.

Figure 63:
FIG. 63 is an image of a breast cancer mastectomy specimen obtained using an X-ray tube in accordance with the subject matter described herein.

FIG. 63 is an image of a breast cancer mastectomy specimen obtained using an X-ray tube in accordance with the subject matter described herein. The image was acquired through a 7.0 cm, full thickness, minimally-compressed breast with a dose of 0.4 mrad. Less than or equal to about 0.5 mrad can be applied to other objects or tissue for achieving suitable images. This image shows diagnostic features in full thickness breast tissue at a dose several hundred times less than in a conventional mammogram. The subject matter described herein is advantageous because it can achieve images of soft tissue objects of high thickness. Previous synchrotron-based devices have been unable to achieve such images. Further, for example, the subject matter described herein can be used to acquire such high-quality images while applying very low doses to objects, such as soft tissue objects. The subject matter described herein can use X-ray beams having higher energy than conventional radiography for achieving high-quality images, thus the subject matter described herein can require a lower dosage to be used because of patient safety concerns.

Exemplary Applications

The systems and methods in accordance with the subject matter described herein can be applied to a variety of medical applications. As set forth above, the systems and methods described herein can be applied for breast imaging. Further, for example, the systems and methods described herein can be applied to cartilage imaging, neuroimaging, cardiac imaging, vascular imaging (with and without contrast), pulmonary (lung) imaging, bone imaging, genitourinary imaging, gastrointestinal imaging, soft tissue imaging in general, hematopoietic system imaging, and endocrine system imaging. In addition to image time and dose, a major advancement of using higher energy X-rays is the thickness of the object that can be imaged. For applications such as breast imaging, the system described allows for imaging full thickness breast tissue with a clinically realistic imaging time. The same can be said for other regions of the body, such as the head, neck, extremities, abdomen, and pelvis. Without the limitations of X-ray absorption, utilization of DEI with higher energy X-rays dramatically increases the penetration ability of X-rays. For soft tissue, only a small portion of the X-ray photons incident on the object are absorbed, which greatly increases efficiency of emitted photons from the X-ray tube reaching the detector.

With respect to pulmonary imaging, DEI techniques as described herein can produce excellent contrast in the lungs and can be used heavily for diagnosing pulmonary conditions such as pneumonia. Fluid collections in the lungs generate a marked density gradient that could be detected easily with DEI. The density gradient, characteristics of the surrounding tissue, and geometric differences between normal lung tissue and tissue with a tumor can be large, producing good contrast. Further, DEI techniques described herein can be applied to lung cancer screening and diagnosis.

With respect to bone imaging, DEI techniques as described herein can produce an excellent image of bone in general. High refraction and extinction contrast of DEI can be especially useful for visualizing fractures and lesions within the bone.

Further, the systems and methods in accordance with the subject matter described herein can be applied to a variety of inspection and industrial applications. For example, the systems and methods can be applied for meat inspection, such as poultry inspection. For example, the systems and methods can be used for viewing sharp bones, feathers, and other low contrast objects in meats that required screening and/or removal. The systems and methods described herein can be applied for such screening.

The systems and methods described herein can also be applied for manufacture inspection. For example, the systems and methods can be used for inspecting welds, such as in aircraft production. DEI techniques as described herein can be used to inspect key structural parts that undergo heavy wear and tear, such as jet turbine blades. Further, for example, the systems and methods described herein can be used for inspecting circuit boards and other electronics. In another example, the systems and methods described herein can be used for tire inspection, such as the inspection of steel belts and tread integrity.

Further, the systems and methods in accordance with the subject matter described herein can be used for security screening purposes. For example, the systems and methods can be used for screening at airports and seaports. DEI techniques as described herein can be used for screening for plastic and low absorption contrast objects, such as plastic knives, composite guns difficult to detect with conventional X-ray, and plastic explosives. For imaging larger objects, such is for airport baggage inspection, the distance between the X-ray tube and detector can be increased to allow beam divergence. A larger analyzer crystal would be necessary to accommodate a larger fan beam.

The device described provides a mechanism that can be translated into a computed tomography imaging system, or DEI-CT. A DEI-CT system, resembling a third generation conventional computed tomography system, would use the same apparatus but modified for rotation around a central point. Alternatively, the system could remain stationary and the object, sample, or patient could be rotated in the beam. A DEI-CT system of this design would produce images representing X-ray absorption, refraction, and ultra-small angle scatter rejection (extinction), but they would be resolved in three dimensions.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for detecting an image of an object, the method comprising:
   (a) generating a first divergent X-ray beam from a non-synchrotron X-ray source, the first X-ray beam having a polychromatic energy distribution and characteristic lines Kα1 and Kα2 with X-ray energies above 40 keV;
   (b) positioning a single monochromator crystal in a predetermined position to directly intercept the first X-ray beam and select and produce a second divergent X-ray beam having a predetermined energy level, the second x-ray beam containing a narrow energy band including characteristic lines Kα1 and Kα2 with X-ray energies above 40 keV;
   (c) positioning an object in a path of the second X-ray beam for transmission of the second X-ray beam through the object and emitting from the object a transmitted X-ray beam;
   (d) directing the transmitted X-ray beam at an angle of incidence upon an analyzer crystal; and
   (e) detecting an image of the object from a beam diffracted from the analyzer crystal.

2. The method of claim 1 wherein generating the first X-ray beam includes generating the first X-ray beam by use of an X-ray tube.

3. The method of claim 2 wherein generating the first X-ray beam includes generating the first X-ray beam from a rotating anode of the X-ray tube.

4. The method of claim 2 wherein generating the first X-ray beam includes generating the first X-ray beam from a stationary anode of the X-ray tube.

5. The method of claim 2 wherein the X-ray tube includes a tungsten target.

6. The method of claim 2 wherein the X-ray tube is set to a power of at least 30 kW for generating the first X-ray beam.

7. The method of claim 1 wherein generating the first X-ray beam includes generating an X-ray beam having a characteristic x-ray energy ranging from 50 keV to 70 keV.

8. The method of claim 1 wherein generating the first X-ray beam includes generating a plurality of X-ray beams fanning out in different directions from an X-ray point source.

9. The method of claim 1 wherein positioning the monochromator crystal includes positioning a surface of the monochromator crystal at an angle of between 1 degrees and 40 degrees with respect to a path of the first X-ray beam incident upon the surface of the monochromator crystal.

10. The method of claim 1 wherein the monochromator crystal is matched in orientation and lattice planes to the analyzer crystal.

11. The method of claim 1 wherein the monochromator crystal is a symmetric crystal.

12. The method of claim 11 wherein the monochromator crystal is a silicon crystal.

13. The method of claim 12 wherein the silicon crystal is positioned for [333] reflection.

14. The method of claim 1 wherein the analyzer crystal is a Bragg type analyzer.

15. The method of claim 1 wherein the object is a soft tissue object.

16. The method of claim 15 wherein the soft tissue object is breast tissue.

17. The method of claim 1 wherein the second X-ray beam applies a radiation dosage of less than or equal to 0.5 mrad to the object.

18. The method of claim 1 wherein detecting the image of the object includes receiving the diffracted beam at a detector.

19. The method of claim 18 wherein the detector is configured to produce a digitized image of the object.

20. The method of claim 18 wherein the detector is a radiographic film.

21. The method of claim 18 wherein the detector is an image plate.

22. The method of claim 1 wherein detecting the image of the object includes detecting the image of the object from the beam diffracted from the analyzer crystal one of at and near a peak of a rocking curve of the analyzer crystal.

23. The method of claim 22 comprising deriving at least one of a diffraction enhanced image, an absorption image, a refraction image, a scatter image, and a mass density image of the object from the detected image.

24. The method of claim 22 wherein the one of at and near the peaks occurs within approximately one-half of a Darwin width of the rocking curve.

25. The method of claim 1 wherein detecting the image of the object includes:
   (a) detecting a first angle image of the object from a first diffracted beam emitted from the analyzer crystal positioned at a first angular position;
   (b) detecting a second angle image of the object from a second diffracted beam emitted from the analyzer crystal positioned at a second angular position;
   (c) combining the first and second angle images to derive a refraction and apparent absorption image; and
   (d) deriving a mass density image of the object from the refraction image.

26. The method of claim 25 wherein detecting the first angle image includes detecting the first angle image of the object from the analyzer crystal at a low rocking curve angle setting of the analyzer crystal, and wherein detecting the second angle image includes detecting the second angle image of the object from the analyzer crystal at a high rocking curve angle setting of the analyzer crystal.

27. The method of claim 1 comprising blocking a portion of the second X-ray beam prior to transmission of the second X-ray beam through the object such that a predetermined characteristic line of the second X-ray beam is blocked.

28. The method of claim 27 wherein blocking the portion of the second X-ray beam includes positioning a collimator between the monochromator crystal and the object such that the predetermined characteristic line of the second X-ray beam is blocked.

29. The method of claim 27 wherein the predetermined characteristic emission line is characteristic emission line Kα1.

30. The method of claim 1 comprising blocking a portion of the first X-ray beam that falls outside of an angular acceptance window of the monochromator crystal prior to interception of the first X-ray beam by the monochromator crystal.

31. The method of claim 30 wherein blocking the portion of the first X-ray beam includes positioning a collimator in a path of the first X-ray beam.

32. The method of claim 1 wherein the monochromator crystal is a first monochromator crystal, and wherein the method comprises positioning a second monochromator crystal to intercept the second X-ray beam and to direct the second X-ray beam towards the analyzer crystal.

33. The method of claim 32 wherein positioning the second monochromator crystal includes positioning the second monochromator crystal such that the second X-ray beam is directed along a path parallel to a path of the first X-ray beam.

34. The method of claim 32 wherein the first and second monochromator crystals are mismatched.

35. The method of claim 32 wherein the first and second monochromator crystals are selected for rejecting a predetermined portion of the first X-ray beam.

36. The method of claim 32 wherein the first and second monochromator crystals are one of germanium and silicon monochromator crystals.

37. The method of claim 32 wherein the first and second monochromator crystals are one of germanium [333] and silicon [333] monochromator crystals.

38. The method of claim 32 wherein at least one of the first and second monochromator crystals is positioned for [111] reflection.

39. The method of claim 32 wherein at least one of the first and second monochromator crystals is a silicon crystal.

40. The method of claim 1 comprising adjusting a radiation dose applied by the second X-ray beam to the object.

41. The method of claim 1 wherein the monochromator crystal is positioned for [111] reflection.

42. The method of claim 1 wherein the analyzer crystal is positioned for [333] reflection.

43. The method of claim 1 wherein the analyzer crystal is positioned for [111] reflection.

44. The method of claim 1 wherein the object is selected from the group consisting of an infant, bone, and cartilage.

45. The method of claim 1 wherein positioning an object in the path of the second X-ray beam comprises moving the object through a first arcuate path; and wherein detecting an image of the object comprises receiving the beam diffracted from the analyzer crystal at a detector by moving the detector through a second arcuate path where an angular speed at which the detector is moved through the second arcuate path is substantially the same as an angular speed at which the object is moved through the first arcuate path.

46. A system for detecting an image of an object, the system comprising:

(a) a non-synchrotron X-ray source configured to generate a first divergent X-ray beam having a polychromatic energy distribution and characteristic lines $K\alpha 1$ and $K\alpha 2$ with X-ray energies above 40 keV;

(b) a single monochromator crystal positioned in a predetermined position to directly intercept the first X-ray beam to select and produce a second divergent X-ray beam having a predetermined energy level for transmission through an object, the second x-ray beam containing a narrow energy band including characteristic lines $K\alpha 1$ and $K\alpha 2$ with X-ray energies above 40 keV;

(c) an analyzer crystal positioned to intercept a transmitted X-ray beam at an angle of incidence of the analyzer crystal; and (d) an image detector configured to detect an image of an object from a beam diffracted from the analyzer crystal.

47. The system of claim 46 wherein the X-ray source is an X-ray tube.

48. The system of claim 47 wherein the X-ray tube includes a rotating anode.

49. The system of claim 47 wherein the X-ray tube includes a stationary anode.

50. The system of claim 47 wherein the X-ray tube includes a tungsten target.

51. The system of claim 47 wherein the X-ray tube is set to a power of at least 30 kW for generating the first X-ray beam.

52. The system of claim 46 wherein the X-ray source is configured to generate an X-ray beam having a characteristic x-ray energy ranging from 50 keV to 70 keV.

53. The system of claim 46 wherein the X-ray source is configured to generate a plurality of X-ray beams fanning out in different directions from an X-ray point source.

54. The system of claim 46 wherein a surface of the monochromator crystal is positioned at an angle of between 1 degrees and 40 degrees with respect to a path of the first X-ray beam incident upon the surface of the monochromator crystal.

55. The system of claim 46 wherein the monochromator crystal is matched in orientation and lattice planes to the analyzer crystal.

56. The system of claim 46 wherein the monochromator crystal is a symmetric crystal.

57. The system of claim 56 wherein the monochromator crystal is a silicon crystal.

58. The system of claim 57 wherein the silicon crystal is positioned for [333] reflection.

59. The system of claim 46 wherein the analyzer crystal is a Bragg type analyzer.

60. The system of claim 46 wherein the object is a soft tissue object.

61. The system of claim 60 wherein the soft tissue object is breast tissue.

62. The system of claim 46 wherein the second X-ray beam applies a radiation dosage of less than or equal to 0.5 mrad to the object.

63. The system of claim 46 comprising wherein the detector is configured to receive the diffracted beam.

64. The system of claim 46 wherein the detector is configured to produce a digitized image of the object.

65. The system of claim 46 wherein the detector is a radiographic film.

66. The system of claim 46 wherein the detector is an image plate.

67. The system of claim 46 wherein the detector is configured to detect the image of the object from the beam diffracted from the analyzer crystal one of at and near a peak of a rocking curve of the analyzer crystal.

68. The system of claim 67 comprising a computer configured to derive at least one of a diffraction enhanced image, an absorption image, a refraction image, a scatter image, and a mass density image of the object from the detected image.

69. The system of claim 67 wherein the one of at and near the peaks occurs within approximately one-half of a Darwin width of the rocking curve.

70. The system of claim 46 wherein the detector is configured to detect a first angle image of the object from a first diffracted beam emitted from the analyzer crystal positioned at a first angular position and configured to detect a second angle image of the object from a second diffracted beam emitted from the analyzer crystal positioned at a second angular position; and the system comprises a computer configured to combine the first and second angle images to derive a refraction image and apparent absorption image, and configured to derive a mass density image of the object from the refraction image.

71. The system of claim 70 wherein the detector is configured to detect the first angle image of the object from the analyzer crystal at a low rocking curve angle setting of the analyzer crystal and configured to detect the second angle image includes detecting the second angle image of the object from the analyzer crystal at a high rocking curve angle setting of the analyzer crystal.

72. The system of claim 46 comprising a collimator positioned to block a portion of the second X-ray beam prior to transmission of the second X-ray beam through the object such that a predetermined characteristic line of the second X-ray beam is blocked.

73. The system of claim 72 wherein the predetermined characteristic emission line is characteristic emission line Kα1.

74. The system of claim 46 comprising a collimator positioned to block a portion of the first X-ray beam that falls outside of an angular acceptance window of the monochromator crystal prior to interception of the first X-ray beam by the monochromator crystal.

75. The system of claim 46 wherein the monochromator crystal is a first monochromator crystal, and wherein the system comprises a second monochromator crystal positioned to intercept the second X-ray beam and to direct the second X-ray beam towards the analyzer crystal.

76. The system of claim 75 wherein the second monochromator crystal is positioned such that the second X-ray beam is directed along a path parallel to a path of the first X-ray beam.

77. The system of claim 75 wherein the first and second monochromator crystals are mismatched.

78. The system of claim 75 wherein the first and second monochromator crystals are selected for rejecting a predetermined portion of the first X-ray beam.

79. The system of claim 75 wherein the first and second monochromator crystals are one of germanium and silicon monochromator crystals.

80. The system of claim 75 wherein the first and second monochromator crystals are one of germanium [333] and silicon [333] monochromator crystals.

81. The system of claim 75 wherein at least one of the first and second monochromator crystals is positioned for [111] reflection.

82. The method of claim 75 wherein at least one of the first and second monochromator crystals is a silicon crystal.

83. The system of claim 46 wherein the monochromator crystal is positioned for [111] reflection.

84. The system of claim 46 wherein the analyzer crystal is positioned for [333] reflection.

85. The system of claim 46 wherein the analyzer crystal is positioned for [111] reflection.

86. The system of claim 46 wherein the object is selected from the group consisting of an infant, bone, and cartilage.

87. The system of claim 46 comprising a scanning stage upon which the object to be imaged is positioned, the scanning stage being movable to move the object through a first arcuate path; and
wherein the image detector is movable through a second arcuate path such that an angular speed at which the detector is moved through the second arcuate path is substantially the same as an angular speed at which the object is moved through the first arcuate path.

88. A method for detecting an image of an object, the method comprising:
(a) generating a first divergent X-ray beam having a polychromatic energy distribution and characteristic lines Kα1 and Kα2 with X-ray energies above 40 keV by generating a plurality of X-ray beams fanning out in different directions from a non-synchrotron X-ray point source;
(b) positioning a monochromator crystal in a predetermined position to intercept the first X-ray beam and select and produce a second divergent X-ray beam having a predetermined energy level, the second x-ray beam containing a narrow energy band including characteristic lines Kα1 and Kα2 with X-ray enemies above 40 keV;
(c) positioning an object in a path of the second X-ray beam for transmission of the second X-ray beam through the object and emitting from the object a transmitted X-ray beam;
(d) directing the transmitted X-ray beam at an angle of incidence upon an analyzer crystal; and
(e) detecting an image of the object from a beam diffracted from the analyzer crystal.

89. The method of claim 88 wherein generating the first X-ray beam includes generating the first X-ray beam by use of an X-ray tube.

90. The method of claim 89 wherein generating the first X-ray beam includes generating the first X-ray beam from a rotating anode of the X-ray tube.

91. The method of claim 89 wherein generating the first X-ray beam includes generating the first X-ray beam from a stationary anode of the X-ray tube.

92. The method of claim 89 wherein the X-ray tube includes a tungsten target.

93. The method of claim 89 wherein the X-ray tube is set to a power of at least 30 kW for generating the first X-ray beam.

94. The method of claim 89 wherein generating the first X-ray beam includes generating an X-ray beam having a characteristic x-ray energy ranging from 50 keV to 70 keV.

95. The method of claim 88 wherein the object is selected from the group consisting of an infant, bone, and cartilage.

96. The method of claim 88 wherein positioning an object in the path of the second X-ray beam comprises moving the object through a first arcuate path; and
wherein detecting an image of the object comprises receiving the beam diffracted from the analyzer crystal at a detector by moving the detector through a second arcuate path at an angular speed that is substantially the same as an angular speed at which the object is moved through the first arcuate path.

97. A system for detecting an image of an object, the system comprising:
(a) an X-ray tube configured to generate a first divergent X-ray beam having a polychromatic energy distribution and characteristic lines Kα1 and Kα2 with X-ray energies above 40 keV by generating a plurality of X-ray beams fanning out in different directions from an X-ray point source of the X-ray tube;
(b) a monochromator crystal positioned in a predetermined position to intercept the first X-ray beam and select and produce a second divergent X-ray beam having a predetermined energy level for transmission through an object, the second x-ray beam containing a narrow energy band including characteristic lines Kα1 and Kα2 with X-ray energies above 40 keV;
(c) an analyzer crystal positioned to intercept a transmitted X-ray beam at an angle of incidence of the analyzer crystal; and
(d) an image detector configured to detect an image of an object from a beam diffracted from the analyzer crystal.

98. The system of claim 97 wherein the X-ray tube includes a rotating anode.

99. The system of claim 97 wherein the X-ray tube includes a stationary anode.

100. The system of claim 97 wherein the X-ray tube includes a tungsten target.

101. The system of claim 97 wherein the X-ray tube is set to a power of at least 30 kW for generating the first X-ray beam.

102. The system of claim 97 wherein the X-ray tube is configured to generate an X-ray beam having a characteristic x-ray energy ranging from 50 keV to 70 keV.

103. The system of claim 97 wherein the object is selected from the group consisting of an infant, bone, and cartilage.

104. The system of claim 97 comprising a scanning stage upon which the object to be imaged is positioned, the scanning stage being movable to move the object through a first arcuate path; and wherein the image detector is movable through a second arcuate path such that an angular speed at which the detector is moved through the second arcuate path is substantially the same as an angular speed at which the object is moved through the first arcuate path.

105. A method for detecting an image of an object, the method comprising:
(a) generating a first divergent X-ray beam from a non-synchrotron X-ray source, the first X-ray beam having first and second characteristic emission lines $K\alpha1$ and $K\alpha2$ with X-ray energies above 40 keV;
(b) positioning a monochromator crystal in a predetermined position to intercept the first X-ray beam and select and produce a second divergent X-ray beam having the first and second characteristic emission lines;
(c) selectively blocking one of the first and second characteristic emission lines of the second X-ray beam and allowing an unblocked one of the first and second characteristic emission lines of the second X-ray beam to pass;
(d) positioning an object in a path of the unblocked one of the first and second characteristic emission lines of the second X-ray beam for transmission of the unblocked characteristic line of the second X-ray beam through the object and emitting from the object a transmitted X-ray beam;
(e) directing the transmitted X-ray beam at an angle of incidence upon an analyzer crystal; and
(f) detecting an image of the object from a beam diffracted from the analyzer crystal.

106. The method of claim 105 wherein generating the first X-ray beam includes generating the first X-ray beam by use of an X-ray tube.

107. The method of claim 106 wherein generating the first X-ray beam includes generating the first X-ray beam from a rotating anode of the X-ray tube.

108. The method of claim 106 wherein generating the first X-ray beam includes generating the first X-ray beam from a stationary anode of the X-ray tube.

109. The method of claim 106 wherein the X-ray tube includes a tungsten target.

110. The method of claim 106 wherein the X-ray tube is set to a power of at least 30 kW for generating the first X-ray beam.

111. The method of claim 105 wherein generating the first X-ray beam includes generating an X-ray beam having a characteristic x-ray energy ranging from 50 keV to 70 keV.

112. The method of claim 105 wherein the object is selected from the group consisting of an infant, bone, and cartilage.

113. The method of claim 105 wherein positioning an object in the path of the unblocked one of the first and second characteristic emission lines of the second X-ray beam comprises moving the object through a first arcuate path; and wherein detecting an image of the object comprises receiving the beam diffracted from the analyzer crystal at a detector by moving the detector through a second arcuate path at an angular speed that is substantially the same as an angular speed at which the object is moved through the first arcuate path.

114. A system for detecting an image of an object, the system comprising:
(a) a non-synchrotron X-ray source configured to generate a first divergent X-ray beam having first and second characteristic emission lines $K\alpha1$ and $K\alpha2$ with X-ray energies above 40 keV;
(b) a monochromator crystal positioned in a predetermined position to intercept the first X-ray beam such that a second divergent X-ray beam having the first and second characteristic emission lines is selected and produced;
(c) a collimator having a slit adjustable for selectively blocking one of the first and second characteristic emission lines of the second X-ray beam and allowing an unblocked one of the first and second characteristic emission lines of the second X-ray beam to pass for transmission through an object;
(d) an analyzer crystal positioned to intercept a transmitted X-ray beam at an angle of incidence of the analyzer crystal; and
(e) an image detector configured to detect an image of an object from a beam diffracted from the analyzer crystal.

115. The system of claim 114 wherein the X-ray source is an X-ray tube.

116. The system of claim 115 wherein the X-ray tube includes a rotating anode.

117. The system of claim 115 wherein the X-ray tube includes a stationary anode.

118. The system of claim 115 wherein the X-ray tube includes a tungsten target.

119. The system of claim 115 wherein the X-ray tube is set to a power of at least 30 kW for generating the first X-ray beam.

120. The system of claim 114 wherein the X-ray source is configured to generate an X-ray beam having a characteristic x-ray energy ranging from 50 keV to 70 keV.

121. The system of claim 114 wherein the object is selected from the group consisting of an infant, bone, and cartilage.

122. The system of claim 114 comprising a scanning stage upon which the object to be imaged is positioned, the scanning stage being movable to move the object through a first arcuate path; and wherein the image detector is movable through a second arcuate path such that an angular speed at which the detector is moved through the second arcuate path is substantially the same as an angular speed at which the object is moved through the first arcuate path.

123. A method for detecting an image of an object, the method comprising:
(a) generating a first divergent X-ray beam from a non-synchrotron X-ray source, the first X-ray beam having first and second characteristic emission lines $K\alpha1$ and $K\alpha2$ with X-ray energies above 40 keV;
(b) positioning a monochromator crystal in a predetermined position to intercept the first X-ray beam and select and produce a second divergent X-ray beam having the first and second characteristic emission lines;
(c) positioning an object in a path of the first and second characteristic emission lines of the second X-ray beam for transmission of the first and second characteristic emission lines of the second X-ray beam through the object and emitting from the object a transmitted X-ray beam;
(d) directing the transmitted X-ray beam at an angle of incidence upon an analyzer crystal; and
(e) detecting an image of the object from a beam diffracted from the analyzer crystal.

124. The method of claim 123 wherein generating the first X-ray beam includes generating the first X-ray beam by use of an X-ray tube.

125. The method of claim 124 wherein generating the first X-ray beam includes generating the first X-ray beam from a rotating anode of the X-ray tube.

126. The method of claim 124 wherein generating the first X-ray beam includes generating the first X-ray beam from a stationary anode of the X-ray tube.

127. The method of claim 124 wherein the X-ray tube includes a tungsten target.

128. The method of claim 124 wherein the X-ray tube is set to a power of at least 30 kW for generating the first X-ray beam.

129. The method of claim 123 wherein generating the first X-ray beam includes generating an X-ray beam having a characteristic x-ray energy ranging from 50 keV to 70 keV.

130. The method of claim 123 wherein the object is selected from the group consisting of an infant, bone, and cartilage.

131. The method of claim 123 wherein positioning an object in the path of the first and second characteristic emission lines of the second X-ray beam comprises moving the object through a first arcuate path; and wherein detecting an image of the object comprises receiving the beam diffracted from the analyzer crystal at a detector by moving the detector through a second arcuate path at an angular speed that is substantially the same as an angular speed at which the object is moved through the first arcuate path.

132. A system for detecting an image of an object, the system comprising:

(a) a non-synchrotron X-ray source configured to generate a first divergent X-ray beam having first and second characteristic emission lines $K\alpha 1$ and $K\alpha 2$ with X-ray energies above 40 keV;

(b) a monochromator crystal positioned in a predetermined position to intercept the first X-ray beam such that a second divergent X-ray beam having the first and second characteristic emission lines is selected and produced for transmission through an object;

(c) an analyzer crystal positioned to intercept a transmitted X-ray beam at an angle of incidence of the analyzer crystal; and (d) an image detector configured to detect an image of an object from a beam diffracted from the analyzer crystal.

133. The system of claim 132 wherein the X-ray source is an X-ray tube.

134. The system of claim 133 wherein the X-ray tube includes a rotating anode.

135. The system of claim 133 wherein the X-ray tube includes a stationary anode.

136. The system of claim 133 wherein the X-ray tube includes a tungsten target.

137. The system of claim 133 wherein the X-ray tube is set to a power of at least 30 kW for generating the first X-ray beam.

138. The system of claim 132 wherein the X-ray source is configured to generate an X-ray beam having a characteristic x-ray energy ranging from 50 keV to 70 keV.

139. The system of claim 132 wherein the object is selected from the group consisting of an infant, bone, and cartilage.

140. The system of claim 132 comprising a scanning stage upon which the object to be imaged is positioned, the scanning stage being movable to move the object through a first arcuate path; and wherein the image detector is movable through a second arcuate path such that an angular speed at which the detector is moved through the second arcuate path is substantially the same as an angular speed at which the object is moved through the first arcuate path.

* * * * *